US012605436B2

(12) United States Patent (10) Patent No.: US 12,605,436 B2
Reinisch et al. (45) Date of Patent: *Apr. 21, 2026

(54) CHIKUNGUNYA VACCINE FORMULATIONS

(71) Applicant: Valneva SE, Nantes (FR)

(72) Inventors: Christoph Reinisch, Siegenfeld (AT);
Robert Schlegl, Siegenfeld (AT);
Jürgen Heindl-Wruss, Vienna (AT)

(73) Assignee: Valneva SE, Nantes (FR)

( * ) Notice: Subject to any disclaimer, the term of this
patent is extended or adjusted under 35
U.S.C. 154(b) by 1076 days.

This patent is subject to a terminal dis-
claimer.

(21) Appl. No.: 17/632,943

(22) PCT Filed: Aug. 10, 2020

(86) PCT No.: PCT/EP2020/072435
§ 371 (c)(1),
(2) Date: Feb. 4, 2022

(87) PCT Pub. No.: WO2021/028406
PCT Pub. Date: Feb. 18, 2021

(65) Prior Publication Data
US 2022/0288185 A1 Sep. 15, 2022

(30) Foreign Application Priority Data

Aug. 9, 2019 (EP) ..................................... 19190999

(51) Int. Cl.
*A61K 39/12* (2006.01)
*A61K 47/02* (2006.01)
*A61K 47/18* (2017.01)
*A61K 47/26* (2006.01)
*A61K 47/42* (2017.01)
*A61K 39/00* (2006.01)

(52) U.S. Cl.
CPC .............. *A61K 39/12* (2013.01); *A61K 47/02*
(2013.01); *A61K 47/183* (2013.01); *A61K*
*47/26* (2013.01); *A61K 47/42* (2013.01); *A61K*
*2039/5254* (2013.01)

(58) Field of Classification Search
None
See application file for complete search history.

(56) References Cited

U.S. PATENT DOCUMENTS

2017/0014502 A1 1/2017 Sumathy et al.
2022/0313810 A1 10/2022 Wressnigg et al.

FOREIGN PATENT DOCUMENTS

WO WO 1998/013065 A1 4/1998
WO WO 2017/109223 A1 6/2017
WO WO 2017/109224 A1 6/2017
WO WO 2017/172643 A1 10/2017
WO WO 2019/057793 A1 3/2019

OTHER PUBLICATIONS

[No Author Listed], Structural polyprotein. Chikungunya virus
(Chikv). UNIPROT Accession No. D2KBQ0. Feb. 9, 2010. Acces-
sible at https://www.uniprot.org/uniprotkb/D2KBQ0/entry. 3 pages.
Hallengärd et al., Novel attenuated Chikungunya vaccine candidates
elicit protective immunity in C57BL/6 mice. J Virol. Mar.
2014;88(5):2858-66. doi: 10.1128/JVI.03453-13. Epub Dec. 26,
2013.
Milligan et al., Defining a correlate of protection for chikungunya
virus vaccines. Vaccine. Nov. 28, 2019;37(50):7427-7436. doi:
10.1016/j.vaccine.2018.10.033. Epub Nov. 15, 2018.
Roques et al., Effectiveness of CHIKV vaccine VLA1553 demon-
strated by passive transfer of human sera. JCI Insight. Jul. 22,
2022;7(14):e160173. doi: 10.1172/jci.insight.160173. 16 pages.
Zheng et al., Genetic analysis of chikungunya viruses imported to
mainland China in 2008. Virol J. Jan. 18, 2010;7:8. doi: 10.1186/
1743-422X-7-8. 6 pages.
[No Author Listed], Declaration of Helsinki. Bulletin of the World
Health Organization. 2001;79(4):373-4.
[No Author Listed], International Conference on Harmonisation
(ICH) of Technical Requirements for Registration of Pharmaceuti-
cals for Human Use / Guideline for Good Clinical Practice. 1996.
59 pages.
[No Author Listed], Number of reported cases of chikungunya fever
in the Americas by country or territory. World Health Organization.
2013-2016. Accessible at http://www.paho.org/hq/index.php?option=
com_topics. 1 page.
[No Author Listed], Valneva Reports Positive 24-Month Antibody
Persistence Data for its Single-Shot Chikungunya Vaccine IXCHIQ®.
Valneva Se. Dec. 4, 2023. 5 pages.
Ahola et al., Therapeutics and vaccines against chikungunya virus.
Vector Borne Zoonotic Dis. Apr. 2015;15(4):250-7. doi: 10.1089/
vbz.2014.1681. Erratum in: Vector Borne Zoonotic Dis. Nov.
2015;15(11):712. Couderc, Therese [Corrected to Couderc, Therese].
Bandeira et al., Prolonged shedding of Chikungunya virus in semen
and urine: A new perspective for diagnosis and implications for
transmission. IDCases. Nov. 4, 2016;6:100-103. doi: 10.1016/j.idcr.
2016.10.007.
Broeckel et al., Therapeutic administration of a recombinant human
monoclonal antibody reduces the severity of chikungunya virus
disease in rhesus macaques. PLoS Negl Trop Dis. Jun. 19,
2017;11(6):e0005637. doi: 10.1371/journal.pntd.0005637.
Chang et al., Effect of sorbitol and residual moisture on the stability
of lyophilized antibodies: Implications for the mechanism of protein
stabilization in the solid state. J Pharm Sci. Jul. 2005;94(7):1445-55.
doi: 10.1002/jps.20363.
Chu et al., Deciphering the protective role of adaptive immunity to
CHIKV/IRES a novel candidate vaccine against Chikungunya in the
A129 mouse model. Vaccine. Jul. 18, 2013;31(33):3353-60. doi:
10.1016/j.vaccine.2013.05.059. Epub May 29, 2013. Author Manu-
script. 19 pages.
Couderc et al., Prophylaxis and therapy for Chikungunya virus
infection. J Infect Dis. Aug. 15, 2009;200(4):516-23. doi: 10.1086/
600381.

(Continued)

*Primary Examiner* — Stacy B Chen
(74) *Attorney, Agent, or Firm* — Wolf, Greenfield &
Sacks, P.C.

(57) ABSTRACT

The present invention is related to novel liquid and lyo-
philized formulations of Chikungunya virus useful as vac-
cines and methods for their preparation.

20 Claims, 26 Drawing Sheets

Specification includes a Sequence Listing.

(56) References Cited

OTHER PUBLICATIONS

Galatas et al., Long-Lasting Immune Protection and Other Epidemiological Findings after Chikungunya Emergence in a Cambodian Rural Community, Apr. 2012. PLoS Negl Trop Dis. Jan. 11, 2016;10(1):e0004281. doi: 10.1371/journal.pntd.0004281.

Gérardin et al., Chikungunya virus-associated encephalitis: A cohort study on La Réunion Island, 2005-2009. Neurology. Jan. 5, 2016;86(1):94-102. doi: 10.1212/WNL.0000000000002234. Epub Nov. 25, 2015.

Kam et al., Early neutralizing IgG response to Chikungunya virus in infected patients targets a dominant linear epitope on the E2 glycoprotein. EMBO Mol Med. Apr. 2012;4(4):330-43. doi: 10.1002/emmm.201200213. Epub Mar. 5, 2012.

Linn et al., Alphavirus-specific cytotoxic T lymphocytes recognize a cross-reactive epitope from the capsid protein and can eliminate virus from persistently infected macrophages. J Virol. Jun. 1998;72(6):5146-53. doi: 10.1128/JVI.72.6.5146-5153.1998.

Lum et al., An essential role of antibodies in the control of Chikungunya virus infection. J Immunol. Jun. 15, 2013;190(12):6295-302. doi: 10.4049/jimmunol.1300304. Epub May 13, 2013.

Musso et al., Detection of chikungunya virus in saliva and urine. Virol J. Jun. 16, 2016;13:102. doi: 10.1186/s12985-016-0556-9. Erratum in: Virol J. 2016;13(1):120.

Muturi-Kioi et al., Neutropenia as an Adverse Event following Vaccination: Results from Randomized Clinical Trials in Healthy Adults and Systematic Review. PLoS One. Aug. 4, 2016;11(8):e0157385. doi: 10.1371/journal.pone.0157385.

Nitatpattana et al., Long-term persistence of Chikungunya virus neutralizing antibodies in human populations of North Eastern Thailand. Virol J. Oct. 21, 2014;11:183. doi: 10.1186/1743-422X-11-183.

Pal et al., Development of a highly protective combination monoclonal antibody therapy against Chikungunya virus. PLoS Pathog. 2013;9(4):e1003312. doi: 10.1371/journal.ppat.1003312. Epub Apr. 18, 2013. 16 pages.

Panning et al., Chikungunya fever in travelers returning to Europe from the Indian Ocean region, 2006. Emerg Infect Dis. Mar. 2008;14(3):416-22. doi: 10.3201/eid1403.070906.

Pastorino et al., Development of a TaqMan RT-PCR assay without RNA extraction step for the detection and quantification of African Chikungunya viruses. J Virol Methods. Mar. 2005;124(1-2):65-71. doi: 10.1016/j.jviromet.2004.11.002. Epub Dec. 15, 2004.

Reed et al., A simple method of estimating fifty percent endpoints. Am J Hygiene. 1938;27:493-497.

Reisinger et al., Immunogenicity, safety, and tolerability of the measles-vectored chikungunya virus vaccine MV-CHIK: a double-blind, randomised, placebo-controlled and active-controlled phase 2 trial. Lancet. Dec. 22, 2019;392(10165):2718-2727. doi: 10.1016/S0140-6736(18)32488-7. Epub Nov. 5, 2018.

Roques et al., Attenuated and vectored vaccines protect nonhuman primates against Chikungunya virus. JCI Insight. Mar. 23, 2017;2(6):e83527. doi: 10.1172/jci.insight.83527.

Schwartz et al., Formulation and Stability of a Chikungunya Virus-Like Particle (ChikV VLP) Based Vaccine. From Vaccine Technology IV. University College London, UK. Wyeth Vaccine Research Eds, ECI Symposium Series. Accessible at http://dc.engconfintl.org/vaccine_jv/17. 2012. 22 pages.

Vega-Rúa et al., Chikungunya virus transmission potential by local Aedes mosquitoes in the Americas and Europe. PLoS Negl Trop Dis. May 20, 2015;9(5):e0003780. doi: 10.1371/journal.pntd.0003780. 18 pages.

Weaver, Arrival of chikungunya virus in the new world: prospects for spread and impact on public health. PLoS Negl Trop Dis. Jun. 26, 2014;8(6):e2921. doi: 10.1371/journal.pntd.0002921. 4 pages.

Wressnigg et al., Single-shot live-attenuated chikungunya vaccine in healthy adults: a phase 1, randomised controlled trial. Lancet Infect Dis. Oct. 2020;20(10):1193-1203. doi: 10.1016/S1473-3099(20)30238-3. Epub Jun. 1, 2020.

Xie et al., Mechanism of the stabilization of ribonuclease A by sorbitol: preferential hydration is greater for the denatured then for the native protein. Protein Sci. Jan. 1997;6(1):211-21. doi: 10.1002/pro.5560060123.

Yoon et al., High rate of subclinical chikungunya virus infection and association of neutralizing antibody with protection in a prospective cohort in the Philippines. PLoS Negl Trop Dis. May 7, 2015;9(5):e0003764. doi: 10.1371/journal.pntd.0003764. 14 pages.

187 individuals screened for eligibility 67 ineligible 120 enrolled 120 randomised 59 assigned to High Dose Group H

Figure 15B:
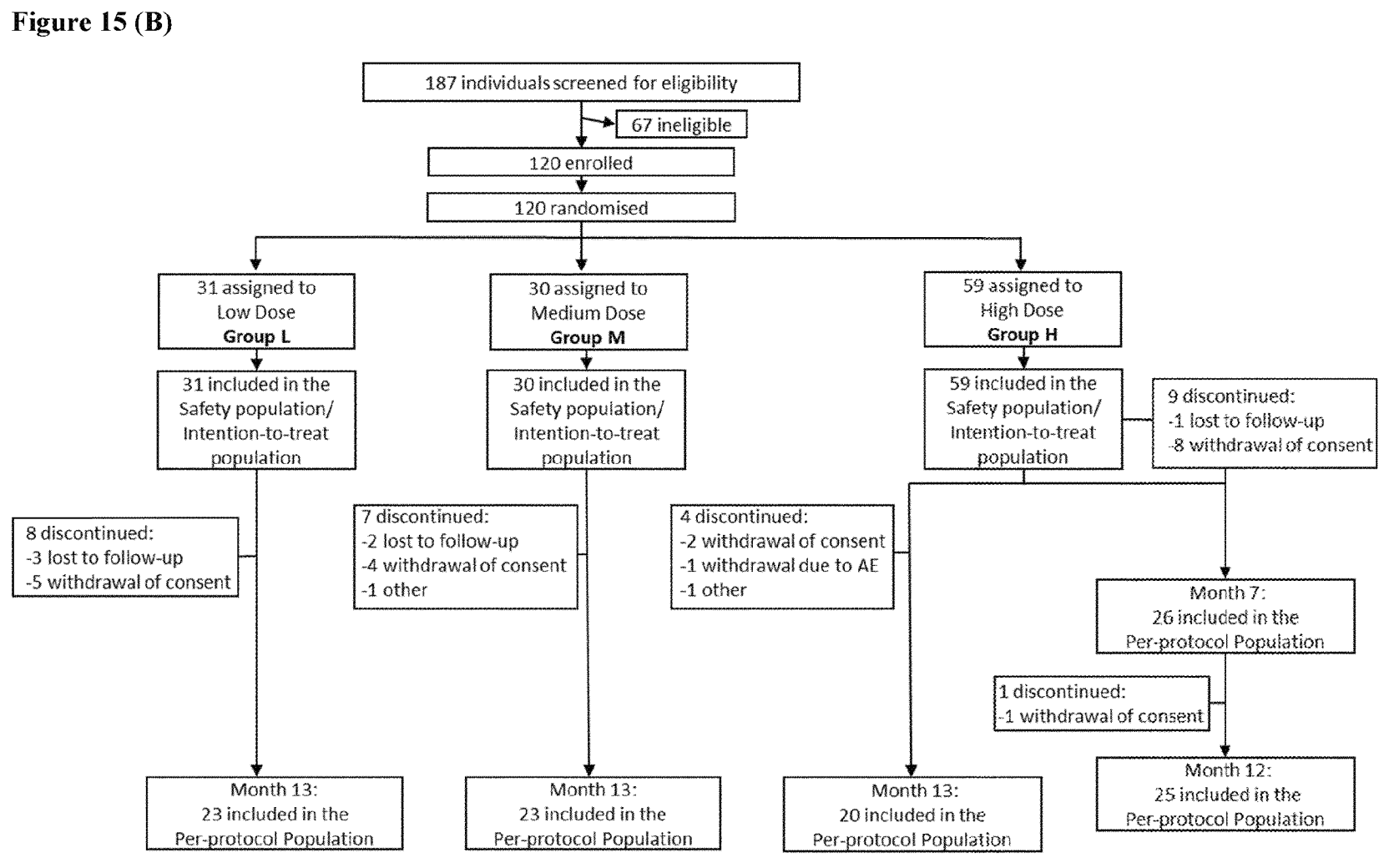

59 included in the Safety population/ Intention-to-treat population 9 discontinued:
-1 lost to follow-up
-8 withdrawal of consent Month 7:
26 included in the Per-protocol Population 1 discontinued:
-1 withdrawal of consent Month 12:
25 included in the Per-protocol Population 4 discontinued:
-2 withdrawal of consent
-1 withdrawal due to AE
-1 other Month 13:
20 included in the Per-protocol Population 30 assigned to Medium Dose Group M

30 included in the Safety population/ Intention-to-treat population 7 discontinued:
-2 lost to follow-up
-4 withdrawal of consent
-1 other Month 13:
23 included in the Per-protocol Population 31 assigned to Low Dose Group L

31 included in the Safety population/ Intention-to-treat population 8 discontinued:
-3 lost to follow-up
-5 withdrawal of consent Month 13:
23 included in the Per-protocol Population

(A) 1:40

(B) 1:80

(C) 1:160

(A)

(B)

SEQUENCE LISTING

<160> NUMBER OF SEQ ID NOS: 7

<210> SEQ ID NO 1
<211> LENGTH: 11674
<212> TYPE: DNA
<213> ORGANISM: Chikungunya virus

<400> SEQUENCE: 1

```
gatggctgcg tgagacacac gtagcctacc agtttcttac tgctctactc tgcaaagcaa        60
gagattaata acccatcatg gatcctgtgt acgtggacat agacgctgac agcgcctttt       120
tgaaggccct gcaacgtgcg taccccatgt ttgaggtgga accaaggcag gtcacaccga       180
```

```
atgaccatgc taatgctaga gcgttctcgc atctagctat aaaactaata gagcaggaaa    240
ttgaccccga ctcaaccatc ctggatatcg gcagtgcgcc agcaaggagg atgatgtcgg    300
acaggaagta ccactgcgtc tgcccgatgc gcagtgcgga agatcccgag agactcgcca    360
attatgcgag aaagctagca tctgccgcag gaaaagtcct ggacagaaac atctctggaa    420
agatcgggga cttacaagca gtaatggccg tgccagacac ggagacgcca acattctgct    480
tacacacaga cgtctcatgt agacagagag cagacgtcgc tatataccaa gacgtctatg    540
ctgtacacgc acccacgtcg ctataccacc aggcgattaa aggggtccga gtggcgtact    600
gggttgggtt cgacacaacc ccgttcatgt acaatgccat ggcgggtgcc tacccctcat    660
actcgacaaa ctgggcagat gagcaggtac tgaaggctaa gaacatagga ttatgttcaa    720
cagacctgac ggaaggtaga cgaggcaagt tgtctattat gagagggaaa aagctaaaac    780
cgtgcgaccg tgtgctgttc tcagtagggt caacgctcta cccggaaagc cgcaagctac    840
ttaagagctg gcacctgcca tcggtgttcc atttaaaggg caaactcagc ttcacatgcc    900
gctgtgatac agtggtttcg tgtgagggct acgtcgttaa gagaataacg atgagcccag    960
gcctttatgg aaaaaccaca gggtatgcgg taacccacca cgcagacgga ttcctgatgt   1020
gcaagactac cgacacggtt gacggcgaaa gaatgtcatt ctcggtgtgc acatacgtgc   1080
cggcgaccat ttgtgatcaa atgaccggca tccttgctac agaagtcacg ccggaggatg   1140
cacagaagct gttggtgggg ctgaaccaga gaatagtggt taacggcaga acgcaacgga   1200
atacgaacac catgaaaaat tatctgcttc ccgtggtcgc ccaagccttc agtaagtggg   1260
caaaggagtg ccggaaagac atggaagatg aaaaactcct gggggtcaga gaaagaacac   1320
tgacctgctg ctgtctatgg gcattcaaga agcagaaaac acacacggtc tacaagaggc   1380
ctgatcccca gtcaattcag aaggttcagg ccgagtttga cagctttgtg gtaccgagtc   1440
tgtggtcgtc cgggttgtca atccctttga ggactagaat caaatggttg ttaagcaagg   1500
tgccaaaaac cgacctgatc ccatacagcg gagacgcccg agaagcccgg gacgcagaaa   1560
aagaagcaga ggaagaacga gaagcagaac tgactcgcga agccctacca cctctacagg   1620
cagcacagga agatgttcag gtcgaaatcg acgtggaaca gcttgaggac agagcgggcg   1680
caggaataat agagactccg agaggagcta tcaaagttac tgcccaacca acagaccacg   1740
tcgtgggaga gtacctggta ctctcccccgc agaccgtact acgtagccag aagctcagtc   1800
tgattcacgc tttggcggag caagtgaaga cgtgcacgca caacggacga gcagggaggt   1860
atgcggtcga agcgtacgac ggccgagtcc tagtgccctc aggctatgca atctcgcctg   1920
aagacttcca gagtctaagc gaaagcgcaa cgatggtgta aacgaaaga gagttcgtaa    1980 acagaaagct acaccatatt gcgatgcacg accagccct gaacaccgac gaagagtcgt   2040
atgagctggt gagggcagag aggacagaac acgagtacgt ctacgacgtg atcagagaa    2100 gatgctgtaa gaaggaagaa gccgcaggac tggtactggt gggcgacttg actaatccgc   2160
cctaccacga attcgcatat gaagggctaa aaatccgccc tgcctgccca tacaaaattg   2220
cagtcatagg agtcttcgga gtaccgggat ctggcaagtc agctattatc aagaacctag   2280
ttaccaggca ggacctggtg actagcggaa agaaagaaaa ctgccaagaa atcaccaccg   2340
acgtgatgag acagagaggt ctagagatat ctgcacgtac ggttgactcg ctgctcttga   2400
atggatgcaa cagaccagtc gacgtgttgt acgtagacga ggcgtttgcg tgccactctg   2460
gaacgctact tgctttgatc gccttggtga gaccaaggca gaaagttgta ctttgtggtg   2520
acccgaagca gtgcggcttc ttcaatatga tgcagatgaa agtcaactat aatcacaaca   2580
```

-continued

```
tctgcaccca agtgtaccac aaaagtatct ccaggcggtg tacactgcct gtgaccgcca      2640
ttgtgtcatc gttgcattac gaaggcaaaa tgcgcactac gaatgagtac aacaagccga      2700
ttgtagtgga cactacaggc tcaacaaaac ctgaccctgg agacctcgtg ttaacgtgct      2760
tcagagggtg ggttaaacaa ctgcaaattg actatcgtgg atacgaggtc atgacagcag      2820
ccgcatccca agggttaacc agaaaaggag tttacgcagt tagacaaaaa gttaatgaaa      2880
acccgctcta tgcatcaacg tcagagcacg tcaacgtact cctaacgcgt acggaaggta      2940
aactggtatg gaagacactt tccggcgacc cgtggataaa gacgctgcag aacccaccga      3000
aaggaaactt caaagcaact attaaggagt gggaggtgga gcatgcatca ataatggcgg      3060
gcatctgcag tcaccaaatg accttcgata cattccaaaa taaagccaac gtttgttggg      3120
ctaagagctt ggtccctatc ctcgaaacag cggggataaa actaaatgat aggcagtggt      3180
ctcagataat tcaagccttc aaagaagaca aagcatactc acctgaagta gccctgaatg      3240
aaatatgtac gcgcatgtat ggggtggatc tagacagcgg gctattttct aaaccgttgg      3300
tgtctgtgta ttacgcggat aaccactggg ataataggcc tggagggaaa atgttcggat      3360
ttaaccccga ggcagcatcc attctagaaa gaaagtatcc attcacaaaa gggaagtgga      3420
acatcaacaa gcagatctgc gtgactacca ggaggataga agactttaac cctaccacca      3480
acatcatacc ggccaacagg agactaccac actcattagt ggccgaacac cgcccagtaa      3540
aaggggaaag aatggaatgg ctggttaaca agataaacgg ccaccacgtg ctcctggtca      3600
gtggctataa ccttgcactg cctactaaga gagtcacttg ggtagcgccg ttaggtgtcc      3660
gcggagcgga ctacacatac aacctagagt tgggtctgcc agcaacgctt ggtaggtatg      3720
acctagtggt cataaacatc cacacacctt ttcgcataca ccattaccaa cagtgcgtcg      3780
accacgcaat gaaactgcaa atgctcgggg gtgactcatt gagactgctc aaaccgggcg      3840
gctctctatt gatcagagca tatggttacg cagatagaac cagtgaacga gtcatctgcg      3900
tattgggacg caagtttaga tcgtctagag cgttgaaacc accatgtgtc accagcaaca      3960
ctgagatgtt tttcctattc agcaactttg acaatggcag aaggaatttc acaactcatg      4020
tcatgaacaa tcaactgaat gcagccttcg taggacaggt cacccgagca ggatgtgcac      4080
cgtcgtaccg ggtaaaacgc atggacatcg cgaagaacga tgaagagtgc gtagtcaacg      4140
ccgctaaccc tcgcgggtta ccgggtggcg gtgtttgcaa ggcagtatac aaaaaatggc      4200
cggagtcctt taagaacagt gcaacaccag tgggaaccgc aaaaacagtt atgtgcggta      4260
cgtatccagt aatccacgct gttggaccaa acttctctaa ttattcggag tctgaagggg      4320
accgggaatt ggcagctgcc tatcgagaag tcgcaaagga agtaactagg ctgggagtaa      4380
atagtgtagc tatacctctc ctctccacag gtgtatactc aggagggaaa gacaggctga      4440
cccagtcact gaaccacctc tttacagcca tggactcgac ggatgcagac gtggtcatct      4500
actgccgcga caaagaatgg gagaagaaaa tatctgaggc catacagatg cggacccaag      4560
tagagctgct ggatgagcac atctccatag actgcgatat tgttcgcgtg caccctgaca      4620
gcagcttggc aggcagaaaa ggatacagca ccacggaagg cgcactgtac tcatatctag      4680
aagggacccg tttttcatcag acggctgtgg atatggcgga gatacatact atgtggccaa      4740
agcaaacaga ggccaatgag caagtctgcc tatatgccct gggggaaagt attgaatcga      4800
tcaggcagaa atgcccggtg gatgatgcag acgcatcatc tcccccaaa actgtcccgt      4860 gcctttgccg ttacgctatg actccagaac gcgtcacccg gcttcgcatg aaccacgtca      4920
```

-continued

```
caagcataat tgtgtgttct tcgtttcccc tcccaaagta caaaatagaa ggagtgcaaa    4980
aagtcaaatg ctctaaggta atgctatttg accacaacgt gccatcgcgc gtaagtccaa    5040
gggcttatag aggtgccgct gccggtaacc ttgcggccgt gtctgattgg gtaatgagca    5100
ccgtacctgt cgcgccgccc agaagaaggc gagggagaaa cctgactgtg acatgtgacg    5160
agagagaagg gaatataaca cccatggcta gcgtccgatt ctttagggca gagctgtgtc    5220
cggtcgtaca agaaacagcg gagacgcgtg acacagcaat gtctcttcag gcaccaccga    5280
gtaccgccac ggaaccgaat catccgccga tctccttcgg agcatcaagc gagacgttcc    5340
ccattacatt tggggacttc aacgaaggag aaatcgaaag cttgtcttct gagctactaa    5400
ctttcggaga cttcttacca ggagaagtgg atgacttgac agacagcgac tggtccacgt    5460
gctcagacac ggacgacgag ttaagactag acagggcagg tgggtatata ttctcgtcgg    5520
acaccggtcc aggtcattta caacagaagt cagtacgcca gtcagtgctg ccggtgaaca    5580
ccctggagga agtccacgag gagaagtgtt acccacctaa gctggatgaa gcaaaggagc    5640
aactattact taagaaactc caggagagtg catccatggc caacagaagc aggtatcagt    5700
cgcgcaaagt agaaaacatg aaagcagcaa tcatccagag actaaagaga ggctgtagac    5760
tatacttaat gtcagagacc ccaaaagtcc ctacttaccg gactacatat ccggcgcctg    5820
tgtactcgcc tccgatcaac gtccgattgt ccaatcccga gtccgcagtg gcagcatgca    5880
atgagttctt agctagaaac tatccaactg tctcatcata ccaaattacc gacgagtatg    5940
atgcatatct agacatggtg gacgggtcgg agagttgcct ggaccgagcg acattcaatc    6000
cgtcaaaact caggagctac ccgaaacagc acgcttacca cgcgccctcc atcagaagcg    6060
ctgtaccgtc cccattccag aacacactac agaatgtact ggcagcagcc acgaaaagaa    6120
actgcaacgt cacacagatg agggaattac ccactttgga ctcagcagta ttcaacgtgg    6180
agtgtttcaa aaaattcgca tgcaaccaag aatactggga agaatttgct gccagcccta    6240
ttaggataac aactgagaat ttagcaacct atgttactaa actaaaaggg ccaaaagcag    6300
cagcgctatt cgcaaaaacc cataatctac tgccactaca ggaagtacca atggataggt    6360
tcacagtaga tatgaaaagg gacgtaaagg tgactcctgg tacaaagcat acagaggaaa    6420
gacctaaggt gcaggttata caggcggctg aacccttggc gacagcatac ctatgtggga    6480
ttcacagaga gctggttagg aggctgaacg ccgtcctcct acccaatgta catacactat    6540
ttgacatgtc tgccgaggat ttcgatgcca tcatagccgc acactttaag ccaggagaca    6600
ctgttttgga aacggacata gcctcctttg ataagagcca agatgattca cttgcgctta    6660
ctgctttgat gctgttagag gatttagggg tggatcactc cctgctggac ttgatagagg    6720
ctgctttcgg agagatttcc agctgtcacc taccgacagg tacgcgcttc aagttcggcg    6780
ccatgatgaa atcaggtatg ttcctaactc tgttcgtcaa cacattgtta aacatcacca    6840
tcgccagccg agtgctggaa gatcgtctga caaaatccgc gtgcgcggcc ttcatcggcg    6900
acgacaacat aatacatgga gtcgtctccg atgaattgat ggcagccaga tgtgccactt    6960
ggatgaacat ggaagtgaag atcatagatg cagttgtatc cttgaaagcc ccttactttt    7020 gtggaggggtt tatactgcac gatactgtga caggaacagc ttgcagagtg gcagacccgc    7080
taaaaaggct ttttaaactg ggcaaaccgc tagcggcagg tgacgaacaa gatgaagata    7140
gaagacgagc gctggctgac gaagtgatca gatggcaacg aacagggcta attgatgagc    7200
tggagaaagc ggtatactct aggtacgaag tgcagggtat atcagttgtg gtaatgtcca    7260
tggccacctt tgcaagctcc agatccaact tcgagaagct cagaggaccc gtcataactt    7320
```

-continued

```
tgtacggcgg tcctaaatag gtacgcacta cagctaccta ttttgcagaa gccgacagca    7380
agtatctaaa cactaatcag ctacaatgga gttcatccca acccaaactt tttacaatag    7440
gaggtaccag cctcgaccct ggactccgcg ccctactatc caagtcatca ggcccagacc    7500
gcgccctcag aggcaagctg ggcaacttgc ccagctgatc tcagcagtta ataaactgac    7560
aatgcgcgcg gtaccacaac agaagccacg caggaatcgg aagaataaga agcaaaagca    7620 aaacaacag gcgccacaaa acaacacaaa tcaaaagaag cagccaccta aaaagaaacc    7680
ggctcaaaag aaaaagaagc cgggccgcag agagaggatg tgcatgaaaa tcgaaaatga    7740
ttgtattttc gaagtcaagc acgaaggtaa ggtaacaggt tacgcgtgcc tggtggggga    7800
caaagtaatg aaaccagcac acgtaaaggg gaccatcgat aacgcggacc tggccaaact    7860
ggcctttaag cggtcatcta agtatgacct tgaatgcgcg cagataccg tgcacatgaa    7920 gtccgacgct tcgaagttca cccatgagaa accggagggg tactacaact ggcaccacgg    7980
agcagtacag tactcaggag gccggttcac catccctaca ggtgctggca aaccagggga    8040
cagcggcaga ccgatcttcg acaacaaggg acgcgtggtg gccatagtct taggaggagc    8100
taatgaagga gcccgtacag ccctctcggt ggtgacctgg aataaagaca ttgtcactaa    8160
aatcaccccc gagggggccg aagagtggag tcttgccatc ccagttatgt gcctgttggc    8220
aaacaccacg ttcccctgct cccagccccc ttgcacgccc tgctgctacg aaaaggaacc    8280
ggaggaaacc ctacgcatgc ttgaggacaa cgtcatgaga cctgggtact atcagctgct    8340
acaagcatcc ttaacatgtt ctccccaccg ccagcgacgc agcaccaagg acaacttcaa    8400
tgtctataaa gccacaagac catacttagc tcactgtccc gactgtggag aagggcactc    8460
gtgccatagt cccgtagcac tagaacgcat cagaaatgaa gcgacagacg ggacgctgaa    8520
aatccaggtc tccttgcaaa tcggaataaa gacggatgac agccacgatt ggaccaagct    8580
gcgttatatg gacaaccaca tgccagcaga cgcagagagg gcgggctat ttgtaagaac    8640 atcagcaccg tgtacgatta ctggaacaat gggacacttc atcctggccc gatgtccaaa    8700
aggggaaact ctgacggtgg gattcactga cagtaggaag attagtcact catgtacgca    8760
cccatttcac cacgaccctc ctgtgatagg tcgggaaaaa ttccattccc gaccgcagca    8820
cggtaaagag ctaccttgca gcacgtacgt gcagagcacc gccgcaacta ccgaggagat    8880
agaggtacac atgcccccag acaccctga tcgcacatta atgtcacaac agtccggcaa    8940
cgtaaagatc acagtcaatg gccagacggt gcggtacaag tgtaattgcg gtggctcaaa    9000
tgaaggacta acaactacag acaaagtgat taataactgc aaggttgatc aatgtcatgc    9060
cgcggtcacc aatcacaaaa agtggcagta taactcccct ctggtccgc gtaatgctga    9120 acttggggac cgaaaggaa aaattcacat cccgtttccg ctggcaaatg taacatgcag    9180
ggtgcctaaa gcaaggaacc ccaccgtgac gtacgggaaa aaccaagtca tcatgctact    9240
gtatcctgac cacccaacac tcctgtccta ccggaatatg ggagaagaac caaactatca    9300
agaagagtgg gtgatgcata agaaggaagt cgtgctaacc gtgccgactg aagggctcga    9360
ggtcacgtgg ggcaacaacg agccgtataa gtattggccg cagttatcta caaacggtac    9420
agcccatggc caccgcatg agataattct gtattattat gagctgtacc ccactatgac    9480
tgtagtagtt gtgtcagtgg ccacgttcat actcctgtcg atggtgggta tggcagcggg    9540
gatgtgcatg tgtgcacgac gcagatgcat cacaccgtat gaactgacac caggagctac    9600
cgtccctttc ctgcttagcc taatatgctg catcagaaca gctaaagcgg ccacatacca    9660
```

-continued

```
agaggctgcg atatacctgt ggaacgagca gcaacctttg ttttggctac aagcccttat    9720
tccgctggca gccctgattg ttctatgcaa ctgtctgaga ctcttaccat gctgctgtaa    9780
aacgttggct tttttagccg taatgagcgt cggtgcccac actgtgagcg cgtacgaaca    9840
cgtaacagtg atcccgaaca cggtgggagt accgtataag actctagtca atagacctgg    9900
ctacagcccc atggtattgg agatggaact actgtcagtc actttggagc caacactatc    9960
gcttgattac atcacgtgcg agtacaaaac cgtcatcccg tctccgtacg tgaagtgctg    10020
cggtacagca gagtgcaagg acaaaaacct acctgactac agctgtaagg tcttcaccgg    10080
cgtctaccca tttatgtggg gcggcgccta ctgcttctgc gacgctgaaa acacgcagtt    10140
gagcgaagca cacgtggaga agtccgaatc atgcaaaaca gaatttgcat cagcatacag    10200
ggctcatacc gcatctgcat cagctaagct ccgcgtcctt taccaaggaa ataacatcac    10260
tgtaactgcc tatgcaaacg gcgaccatgc cgtcacagtt aaggacgcca aattcattgt    10320
ggggccaatg tcttcagcct ggacaccttt cgacaacaaa attgtggtgt acaaaggtga    10380
cgtctataac atggactacc gcccctttgg cgcaggaaga ccaggacaat ttggcgatat    10440
ccaaagtcgc acacctgaga gtaaagacgt ctatgctaat acacaactgg tactgcagag    10500
accggctgtg ggtacggtac acgtgccata ctctcaggca ccatctggct ttaagtattg    10560
gctaaaagaa cgcggggcgt cgctgcagca cacagcacca tttggctgcc aaatagcaac    10620
aaacccggta gagcggtga actgcgccgt agggaacatg cccatctcca tcgacatacc    10680
ggaagcggcc ttcactaggg tcgtcgacgc gccctcttta acggacatgt cgtgcgaggt    10740
accagcctgc acccattcct cagactttgg gggcgtcgcc attattaaat atgcagccag    10800
caagaaaggc aagtgtgcgg tgcattcgat gactaacgcc gtcactattc gggaagctga    10860
gatagaagtt gaagggaatt ctcagctgca aatctctttc tcgacggcct tagccagcgc    10920
cgaattccgc gtacaagtct gttctacaca gtacactgt gcagccgagt gccacccccc    10980
gaaggaccac atagtcaact acccggcgtc acataccacc ctcggggtcc aggacatctc    11040
cgctacggcg atgtcatggg tgcagaagat cacgggaggt gtgggactgg ttgttgctgt    11100
tgccgcactg attctaatcg tggtgctatg cgtgtcgttc agcaggcact aacttgacaa    11160
ttaagtatga aggtatatgt gtcccctaag agacacactg tacatagcaa ataatctata    11220
gatcaaaggg ctacgcaacc cctgaatagt aacaaaatac aaaatcacta aaaattataa    11280
aaacagaaaa atacataaat aggtatacgt gtcccctaag agacacattg tatgtaggtg    11340
ataagtatag atcaaagggc cgaataaccc ctgaatagta acaaaatatg aaaatcaata    11400
aaaatcataa aatagaaaaa ccataaacag aagtagttca aagggctata aaacccctga    11460
atagtaacaa aacataaaat taataaaaat caaatgaata ccataattgg caaacggaag    11520
agatgtaggt acttaagctt cctaaaagca gccgaactca ctttgagaag taggcatagc    11580
ataccgaact cttccacgat tctccgaacc cacaggacg taggagatgt tattttgttt    11640
ttaatatttc aaaaaaaaaa aaaaaaaaaa aaaa                                11674
```

<210> SEQ ID NO 2
<211> LENGTH: 423
<212> TYPE: PRT
<213> ORGANISM: Chikungunya virus

<400> SEQUENCE: 2

```
Ser Thr Lys Asp Asn Phe Asn Val Tyr Lys Ala Thr Arg Pro Tyr Leu
1               5                   10                  15
```

```
Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Asp Ser His Asp Trp
        50                  55                  60

Thr Lys Leu Arg Tyr Met Asp Asn His Met Pro Ala Asp Ala Glu Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
                100                 105                 110

Val Gly Phe Thr Asp Ser Arg Lys Ile Ser His Ser Cys Thr His Pro
            115                 120                 125

Phe His His Asp Pro Pro Val Ile Gly Arg Glu Lys Phe His Ser Arg
        130                 135                 140

Pro Gln His Gly Lys Glu Leu Pro Cys Ser Thr Tyr Val Gln Ser Thr
145                 150                 155                 160

Ala Ala Thr Thr Glu Glu Ile Glu Val His Met Pro Pro Asp Thr Pro
                165                 170                 175

Asp His Thr Leu Met Ser Gln Gln Ser Gly Asn Val Lys Ile Thr Val
                180                 185                 190

Asn Gly Gln Thr Val Arg Tyr Lys Cys Asn Cys Gly Gly Ser Asn Glu
            195                 200                 205

Gly Leu Thr Thr Thr Asp Lys Val Ile Asn Asn Cys Lys Val Asp Gln
        210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
                260                 265                 270

Asn Pro Thr Val Thr Tyr Gly Lys Asn Gln Val Ile Met Leu Leu Tyr
            275                 280                 285

Pro Asp His Pro Thr Leu Leu Ser Tyr Arg Asn Met Gly Glu Glu Pro
        290                 295                 300

Asn Tyr Gln Glu Glu Trp Val Met His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
            340                 345                 350

His Glu Ile Ile Leu Tyr Tyr Tyr Glu Leu Tyr Pro Thr Met Thr Val
            355                 360                 365

Val Val Val Ser Val Ala Thr Phe Ile Leu Leu Ser Met Val Gly Met
        370                 375                 380

Ala Ala Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala
                420
```

-continued

```
<210> SEQ ID NO 3
<211> LENGTH: 423
<212> TYPE: PRT
<213> ORGANISM: Artificial Sequence
<220> FEATURE:
<223> OTHER INFORMATION: mutation arising from Vero passaging

<400> SEQUENCE: 3

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Lys Thr Asp Asp Ser His Asp Trp
    50                  55                  60

Thr Lys Leu Arg Tyr Met Asp Asn His Met Pro Ala Asp Ala Glu Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
        115                 120                 125

Phe His His Asp Pro Pro Val Ile Gly Arg Glu Lys Phe His Ser Arg
        130                 135                 140

Pro Gln His Gly Lys Glu Leu Pro Cys Ser Thr Tyr Val Gln Ser Thr
145                 150                 155                 160

Ala Ala Thr Thr Glu Glu Ile Lys Val His Met Pro Pro Asp Thr Pro
                165                 170                 175

Asp His Thr Leu Met Ser Gln Gln Ser Gly Asn Val Lys Ile Thr Val
            180                 185                 190

Asn Gly Gln Thr Val Arg Tyr Lys Cys Asn Cys Gly Gly Ser Asn Glu
        195                 200                 205

Gly Leu Thr Thr Thr Asp Lys Val Ile Asn Asn Cys Lys Val Asp Gln
        210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Ile Met Leu Leu Tyr
            275                 280                 285

Pro Asp His Pro Thr Leu Leu Ser Tyr Arg Asn Met Gly Glu Glu Pro
        290                 295                 300

Asn Tyr Gln Glu Glu Trp Val Met His Lys Lys Glu Val Val Leu Thr
305                 310                 315                 320

Val Pro Thr Glu Gly Leu Glu Val Thr Trp Gly Asn Asn Glu Pro Tyr
                325                 330                 335

Lys Tyr Trp Pro Gln Leu Ser Thr Asn Gly Thr Ala His Gly His Pro
            340                 345                 350

His Glu Ile Ile Leu Tyr Tyr Tyr Glu Leu Tyr Pro Thr Met Thr Val
        355                 360                 365

Val Val Val Ser Val Ala Thr Phe Ile Leu Leu Ser Met Val Gly Met
```

-continued

```
        370                375                380
Ala Ala Gly Met Cys Met Cys Ala Arg Arg Arg Cys Ile Thr Pro Tyr
385                390                395                400

Glu Leu Thr Pro Gly Ala Thr Val Pro Phe Leu Leu Ser Leu Ile Cys
                405                410                415

Cys Ile Arg Thr Ala Lys Ala
            420

<210> SEQ ID NO 4
<211> LENGTH: 423
<212> TYPE: PRT
<213> ORGANISM: Artificial Sequence
<220> FEATURE:
<223> OTHER INFORMATION: mutation arising from Vero passaging

<400> SEQUENCE: 4

Ser Thr Lys Asp Asn Phe Asn Val Tyr Lys Ala Thr Arg Pro Tyr Leu
1                5                10                15

Ala His Cys Pro Asp Cys Gly Glu Gly His Ser Cys His Ser Pro Val
                20                25                30

Ala Leu Glu Arg Ile Arg Asn Glu Ala Thr Asp Gly Thr Leu Lys Ile
            35                40                45

Gln Val Ser Leu Gln Ile Arg Ile Lys Thr Asp Asp Ser His Asp Trp
        50                55                60

Thr Lys Leu Arg Tyr Met Asp Asn His Met Pro Ala Asp Ala Glu Arg
65                70                75                80

Ala Gly Leu Phe Val Arg Thr Ser Ala Pro Cys Thr Ile Thr Gly Thr
                85                90                95

Met Gly His Phe Ile Leu Ala Arg Cys Pro Lys Gly Glu Thr Leu Thr
                100                105                110

Val Gly Phe Thr Asp Ser Arg Lys Ile Ser His Ser Cys Thr His Pro
            115                120                125

Phe His His Asp Pro Pro Val Ile Gly Arg Glu Lys Phe His Ser Arg
        130                135                140

Pro Gln His Gly Lys Glu Leu Pro Cys Ser Thr Tyr Val Gln Ser Thr
145                150                155                160

Ala Ala Thr Thr Glu Glu Ile Glu Val His Met Pro Pro Asp Thr Pro
                165                170                175

Asp His Thr Leu Met Ser Gln Gln Ser Gly Asn Val Lys Ile Thr Val
                180                185                190

Asn Gly Gln Thr Val Arg Tyr Lys Cys Asn Cys Gly Gly Ser Asn Glu
            195                200                205

Gly Leu Thr Thr Thr Asp Lys Val Ile Asn Asn Cys Lys Val Asp Gln
        210                215                220

Cys His Ala Ala Val Thr Asn His Lys Lys Trp Gln Tyr Asn Ser Pro
225                230                235                240

Leu Val Pro Arg Asn Ala Glu Leu Gly Asp Arg Lys Gly Lys Ile His
                245                250                255

Ile Pro Phe Pro Leu Ala Asn Val Thr Cys Arg Val Pro Lys Ala Arg
                260                265                270

Asn Pro Thr Val Thr Tyr Gly Lys Asn Gln Val Ile Met Leu Leu Tyr
            275                280                285

Pro Asp His Pro Thr Leu Leu Ser Tyr Arg Asn Met Gly Glu Glu Pro
        290                295                300

Asn Tyr Gln Glu Glu Trp Val Met His Lys Lys Glu Val Val Leu Thr
```

-continued

```
305                310                315                320

Val Pro Thr Glu Gly Leu Glu Val Thr Trp Gly Asn Asn Glu Pro Tyr
                325                330                335

Lys Tyr Trp Pro Gln Leu Ser Thr Asn Gly Thr Ala His Gly His Pro
                340                345                350

His Glu Ile Ile Leu Tyr Tyr Tyr Glu Leu Tyr Pro Thr Met Thr Val
                355                360                365

Val Val Val Ser Val Ala Thr Phe Ile Leu Leu Ser Met Val Gly Met
                370                375                380

Ala Ala Gly Met Cys Met Cys Ala Arg Arg Arg Cys Ile Thr Pro Tyr
385                390                395                400

Glu Leu Thr Pro Gly Ala Thr Val Pro Phe Leu Leu Ser Leu Ile Cys
                405                410                415

Cys Ile Arg Thr Ala Lys Ala
                420
```

```
<210> SEQ ID NO 5
<211> LENGTH: 423
<212> TYPE: PRT
<213> ORGANISM: Artificial Sequence
<220> FEATURE:
<223> OTHER INFORMATION: mutation arising from Vero passaging

<400> SEQUENCE: 5

Ser Thr Lys Asp Asn Phe Asn Val Tyr Lys Ala Thr Arg Pro Tyr Leu
1                5                10                15

Ala His Cys Pro Asp Cys Gly Glu Gly His Ser Cys His Ser Pro Val
                20                25                30

Ala Leu Glu Arg Ile Arg Asn Glu Ala Thr Asp Gly Thr Leu Lys Ile
                35                40                45

Gln Val Ser Leu Gln Ile Gly Ile Lys Thr Asp Asp Ser His Asp Trp
                50                55                60

Thr Lys Leu Arg Tyr Met Asp Asn His Met Pro Ala Asp Ala Glu Arg
65                70                75                80

Ala Gly Leu Phe Val Arg Thr Ser Ala Pro Cys Thr Ile Thr Gly Thr
                85                90                95

Met Gly His Phe Ile Leu Ala Arg Cys Pro Lys Gly Glu Thr Leu Thr
                100                105                110

Val Gly Phe Thr Asp Ser Arg Lys Ile Ser His Ser Cys Thr His Pro
                115                120                125

Phe His His Asp Pro Pro Val Ile Gly Arg Glu Lys Phe His Ser Arg
                130                135                140

Pro Gln His Gly Lys Glu Leu Pro Cys Ser Thr Tyr Val Gln Ser Thr
145                150                155                160

Ala Ala Thr Thr Glu Glu Ile Glu Val His Met Pro Pro Asp Thr Pro
                165                170                175

Asp His Thr Leu Met Ser Gln Gln Ser Gly Asn Val Lys Ile Thr Val
                180                185                190

Asn Gly Gln Thr Val Arg Tyr Lys Cys Asn Cys Gly Gly Ser Asn Glu
                195                200                205

Gly Leu Thr Thr Thr Asp Lys Val Ile Asn Asn Cys Lys Val Asp Gln
                210                215                220

Cys His Ala Ala Val Thr Asn His Lys Lys Trp Gln Tyr Asn Ser Pro
225                230                235                240

Leu Val Pro Arg Asn Ala Lys Leu Gly Asp Arg Lys Gly Lys Ile His
```

```
                    245                 250                 255

Ile Pro Phe Pro Leu Ala Asn Val Thr Cys Arg Val Pro Lys Ala Arg
            260                 265                 270

Asn Pro Thr Val Thr Tyr Gly Lys Asn Gln Val Ile Met Leu Leu Tyr
            275                 280                 285

Pro Asp His Pro Thr Leu Leu Ser Tyr Arg Asn Met Gly Glu Glu Pro
            290                 295                 300

Asn Tyr Gln Glu Glu Trp Val Met His Lys Lys Glu Val Val Leu Thr
305                 310                 315                 320

Val Pro Thr Glu Gly Leu Glu Val Thr Trp Gly Asn Asn Glu Pro Tyr
                    325                 330                 335

Lys Tyr Trp Pro Gln Leu Ser Thr Asn Gly Thr Ala His Gly His Pro
                    340                 345                 350

His Glu Ile Ile Leu Tyr Tyr Tyr Glu Leu Tyr Pro Thr Met Thr Val
            355                 360                 365

Val Val Val Ser Val Ala Thr Phe Ile Leu Leu Ser Met Val Gly Met
            370                 375                 380

Ala Ala Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                    405                 410                 415

Cys Ile Arg Thr Ala Lys Ala
            420
```

```
<210> SEQ ID NO 6
<211> LENGTH: 423
<212> TYPE: PRT
<213> ORGANISM: Artificial Sequence
<220> FEATURE:
<223> OTHER INFORMATION: mutation arising from Vero passaging

<400> SEQUENCE: 6

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
            35                  40                  45

Gln Val Ser Leu Gln Ile Gly Ile Lys Thr Asp Asp Ser His Asp Trp
        50                  55                  60

Thr Lys Leu Arg Tyr Met Asp Asn His Met Pro Ala Asp Ala Glu Arg
65                  70                  75                  80

Ala Arg Leu Phe Val Arg Thr Ser Ala Pro Cys Thr Ile Thr Gly Thr
                    85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
            115                 120                 125

Phe His His Asp Pro Pro Val Ile Gly Arg Glu Lys Phe His Ser Arg
            130                 135                 140

Pro Gln His Gly Lys Glu Leu Pro Cys Ser Thr Tyr Val Gln Ser Thr
145                 150                 155                 160

Ala Ala Thr Thr Glu Glu Ile Glu Val His Met Pro Pro Asp Thr Pro
                    165                 170                 175

Asp His Thr Leu Met Ser Gln Gln Ser Gly Asn Val Lys Ile Thr Val
```

-continued

```
                180             185             190
Asn Gly Gln Thr Val Arg Tyr Lys Cys Asn Cys Gly Gly Ser Asn Glu
        195             200             205
Gly Leu Thr Thr Thr Asp Lys Val Ile Asn Asn Cys Lys Val Asp Gln
    210             215             220
Cys His Ala Ala Val Thr Asn His Lys Lys Trp Gln Tyr Asn Ser Pro
225             230             235             240
Leu Val Pro Arg Asn Ala Glu Leu Gly Asp Arg Lys Gly Lys Ile His
            245             250             255
Ile Pro Phe Pro Leu Ala Asn Val Thr Cys Arg Val Pro Lys Ala Arg
            260             265             270
Asn Pro Thr Val Thr Tyr Gly Lys Asn Gln Val Ile Met Leu Leu Tyr
        275             280             285
Pro Asp His Pro Thr Leu Leu Ser Tyr Arg Asn Met Gly Glu Glu Pro
        290             295             300
Asn Tyr Gln Glu Glu Trp Val Met His Lys Lys Glu Val Val Leu Thr
305             310             315             320
Val Pro Thr Glu Gly Leu Glu Val Thr Trp Gly Asn Asn Glu Pro Tyr
            325             330             335
Lys Tyr Trp Pro Gln Leu Ser Thr Asn Gly Thr Ala His Gly His Pro
            340             345             350
His Glu Ile Ile Leu Tyr Tyr Tyr Glu Leu Tyr Pro Thr Met Thr Val
        355             360             365
Val Val Val Ser Val Ala Thr Phe Ile Leu Leu Ser Met Val Gly Met
    370             375             380
Ala Ala Gly Met Cys Met Cys Ala Arg Arg Arg Cys Ile Thr Pro Tyr
385             390             395             400
Glu Leu Thr Pro Gly Ala Thr Val Pro Phe Leu Leu Ser Leu Ile Cys
            405             410             415
Cys Ile Arg Thr Ala Lys Ala
            420
```

```
<210> SEQ ID NO 7
<211> LENGTH: 423
<212> TYPE: PRT
<213> ORGANISM: Artificial Sequence
<220> FEATURE:
<223> OTHER INFORMATION: mutation arising from Vero passaging

<400> SEQUENCE: 7

Ser Thr Lys Asp Asn Phe Asn Val Tyr Lys Ala Thr Arg Pro Tyr Leu
1               5               10              15
Ala His Cys Pro Asp Cys Gly Glu Gly His Ser Cys His Ser Pro Val
            20              25              30
Ala Leu Glu Arg Ile Arg Asn Glu Ala Thr Asp Gly Thr Leu Lys Ile
        35              40              45
Gln Val Ser Leu Gln Ile Gly Ile Lys Thr Asp Asp Ser His Asp Trp
    50              55              60
Thr Lys Leu Arg Tyr Met Asp Asn His Met Pro Ala Asp Ala Glu Arg
65              70              75              80
Ala Gly Leu Phe Val Arg Thr Ser Ala Pro Cys Thr Ile Thr Gly Thr
            85              90              95
Met Gly His Phe Ile Leu Ala Arg Cys Pro Lys Gly Glu Thr Leu Thr
            100             105             110
Val Gly Phe Thr Asp Ser Arg Lys Ile Ser His Ser Cys Thr His Pro
```

-continued

```
        115             120             125

Phe His His Asp Pro Pro Val Ile Gly Arg Glu Lys Phe His Ser Arg
    130             135             140

Pro Gln His Gly Lys Glu Leu Pro Cys Ser Thr Tyr Val Gln Ser Thr
145             150             155             160

Ala Ala Thr Thr Glu Glu Ile Glu Val His Met Pro Pro Asp Thr Pro
                165             170             175

Asp His Thr Leu Met Ser Gln Gln Ser Gly Asn Val Lys Ile Thr Val
            180             185             190

Asn Gly Gln Thr Val Arg Tyr Lys Cys Asn Cys Gly Gly Ser Asn Glu
            195             200             205

Gly Leu Thr Thr Thr Asp Lys Val Ile Asn Asn Cys Lys Val Asp Gln
    210             215             220

Cys His Ala Ala Val Thr Asn Tyr Lys Lys Trp Gln Tyr Asn Ser Pro
225             230             235             240

Leu Val Pro Arg Asn Ala Glu Leu Gly Asp Arg Lys Gly Lys Ile His
            245             250             255

Ile Pro Phe Pro Leu Ala Asn Val Thr Cys Arg Val Pro Lys Ala Arg
            260             265             270

Asn Pro Thr Val Thr Tyr Gly Lys Asn Gln Val Ile Met Leu Leu Tyr
            275             280             285

Pro Asp His Pro Thr Leu Leu Ser Tyr Arg Asn Met Gly Glu Glu Pro
    290             295             300

Asn Tyr Gln Glu Glu Trp Val Met His Lys Lys Glu Val Val Leu Thr
305             310             315             320

Val Pro Thr Glu Gly Leu Glu Val Thr Trp Gly Asn Asn Glu Pro Tyr
            325             330             335

Lys Tyr Trp Pro Gln Leu Ser Thr Asn Gly Thr Ala His Gly His Pro
            340             345             350

His Glu Ile Ile Leu Tyr Tyr Tyr Glu Leu Tyr Pro Thr Met Thr Val
            355             360             365

Val Val Val Ser Val Ala Thr Phe Ile Leu Leu Ser Met Val Gly Met
    370             375             380

Ala Ala Gly Met Cys Met Cys Ala Arg Arg Arg Cys Ile Thr Pro Tyr
385             390             395             400

Glu Leu Thr Pro Gly Ala Thr Val Pro Phe Leu Leu Ser Leu Ile Cys
            405             410             415

Cys Ile Arg Thr Ala Lys Ala
            420
```

CHIKUNGUNYA VACCINE FORMULATIONS

RELATED APPLICATION

This Application is a national stage filing under 35 U.S.C. 371 of International Patent Application Serial No. PCT/EP2020/072435, filed Aug. 10, 2020, the content of which is incorporated by reference herein in its entirety.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jan. 17, 2022, is named I0422.70141US00-SEQ-JRV, and is 37,942 bytes in size.

FIELD OF THE INVENTION

The present invention is related to novel liquid and lyophilized formulations of Chikungunya virus useful as vaccines and methods for their preparation.

BACKGROUND OF THE INVENTION

The Chikungunya virus (CHIKV) is currently regarded as one of the most-likely viruses to spread globally or at least regionally, and morbidity due to this virus is considered a serious threat to global and regional public health, raising an urgent demand for efficient prophylaxis. Eminently, due to climate change, the threat posed by Chikungunya could be amplified increasing the size of the human population at risk of infection. However, at present there is no treatment or vaccine available against this CHIKV-induced debilitating disease and its various symptoms. CHIKV has been reported in over 100 countries with more than 2.2 million suspected cases in the Americas alone (World Health Organization. Number of reported cases of chikungunya fever in the Americas by country or territory 2013-2016: paho.org/hq/index.php?option=com_topics).

CHIKV is a small spherical RNA virus and a member of the Alphavirus genus in the family Togaviridae. The arthropod-borne virus is closely related to other viruses in Africa, South America and Australia that cause similar symptoms such as Ross River Virus, Mayaro-virus or O'nyong-nyong-virus. The virus is vectored by the daytime-biting *Aedes aegypti* mosquito, which also transmits yellow fever, Zika and dengue viruses. CHIKV can also be transmitted by *Aedes albopictus* mosquitoes, a more cold-tolerant mosquito that could easily facilitate the spread of Chikungunya to more temperate areas of the world. An infection with CHIKV results in chronic and incapacitating arthralgia affecting all gender and age groups accompanied by an acute febrile disease with headache, muscle pain, and skin rashes. The severe, often debilitating joint pain in infected patients can persist for years, especially in adults. Individuals who are at higher risk of more serious complications include infants, the elderly and individuals with chronic medical conditions. Since neither a specific antiviral treatment nor a vaccine is available to prevent CHIKV infection, prevention against CHIKV infection is therefore limited to non-treatment interventions such as the employment of insecticides, wearing long sleeves and pants, and other means to restrict exposure to vector mosquitoes.

Recently, a live-attenuated Chikungunya virus vaccine candidate designed for active immunization for the prevention of disease caused by CHIKV has been developed (Hallengärd et al., Novel Attenuated Chikungunya Vaccine Candidates Elicit Protective Immunity in C57BL/6 mice, Journal of Virology, 2014, Vol. 88(5) p. 2858-2866). The candidate vaccine was further developed with the aim to prevent CHIKV disease in the general population living in endemic regions, as well as to serve as a prophylactic measure for travelers to epidemic areas or areas at risk for an upcoming outbreak (see also WO2019057793, WO2017109223, WO2017109224). The replicating CHIKV vaccine comprises a large deletion of 60 amino acids in the nsP3 gene encoding the non-structural replicase complex protein nsP3 leading to attenuation of the virus in vivo. The candidate vaccine is based on the La Reunion strain of the East Central South African genotype and is produced in Vero cells and purified by centrifugation, ultrafiltration, batch-chromatography and sucrose gradient centrifugation. In C57BL/6 mice, the vaccine elicited high titers of binding and neutralizing antibodies after a single immunization and mice were subsequently protected from a high dose CHIKV challenge (Hallengard D, Kakoulidou M, Lulla A, Kummerer B M, Johansson D X, Mutso M, et al. Novel Attenuated Chikungunya Vaccine Candidates Elicit Protective Immunity in C57BL/6 mice. 2014 J Virol 88:2858-66. doi:10.1128/JVL03453-1311). Essentially, a single immunization in non-human primates protected against a wild-type CHIKV infection (Roques P, Ljungberg K, Kümmerer B M, Gosse L, Dereuddre-Bosquet N, Tchitchek N, et al. Attenuated and vectored vaccines protect nonhuman primates against Chikungunya virus. 2017 JCI Insight 2:e83527. doi:10.1172/jci.insight.83527). The novel vaccine is designed to protect against all circulating genotypes of CHIKV throughout the world.

For worldwide distribution of CHIKV vaccines, it is necessary to formulate vaccines such that they are stable under a variety of environmental conditions and over an extended period of time. Components used to stabilize vaccines are known. However, particular formulations of components useful to stabilize CHIKV vaccines must be determined and might not be achieve suitable stability of the vaccine, e.g. of the attenuated vaccine candidate described above. Unfortunately, the live-attenuated forms of CHIKV proposed for vaccine use may be rather unstable in various environments. Thus, one object of the present invention is to provide formulations which stabilize CHIKV vaccines, and in particular which stabilize the CHIKV vaccine at a particular dose.

SUMMARY OF THE INVENTION

The present invention provides novel formulations of CHIKV useful as vaccines and methods for their preparation.

BRIEF DESCRIPTION OF THE DRAWINGS

The accompanying drawings are not intended to be drawn to scale. The Figures are illustrative only and are not required for enablement of the disclosure. For purposes of clarity, not every component may be labeled in every drawing. In the drawings:

FIG. 1 Schematic illustration of the CHIKV-Δ5nsP3 genome structure. The Chikungunya virus genome encodes two polyproteins: non-structural proteins 1-4 (nsP1-4) and structural proteins (C, E3, E2, 6K, E1). Compared with the wild-type genomic sequence, the CHIKV-Δ5nsP3 sequence contains a 183-bp deletion in the 3' part of the sequence encoding nsP3 (amino acids 1656 to 1717 in the nsP1-4 polyprotein), which results in a 60 amino acid deletion in the nsP3 replicase protein (indicated by Δ60aa). SP, subgenomic promoter; UTR, untranslated region. (Figure adapted from Hallengärd D, et al., 2014, supra.)

FIG. 15 Clinical trial design (A) and profile (B).

DETAILED DESCRIPTION OF THE INVENTION

Figure 2:
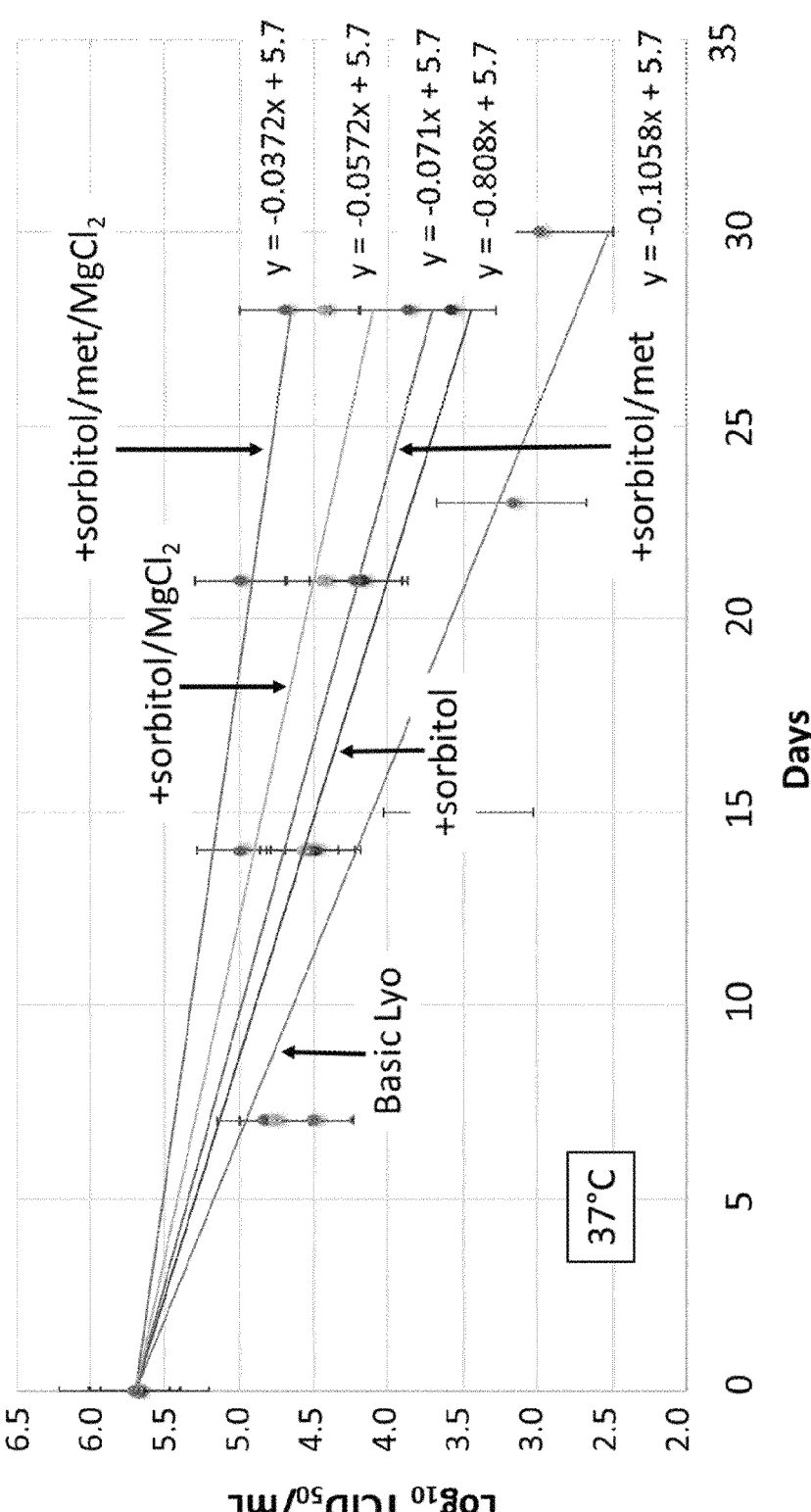
FIG. 2 Effects of sorbitol, magnesium chloride and L-methionine on the stability of freeze-dried CHIKV at 37° C. $TCID_{50}$ assay (error bars of ±0.3 log) performed directly after reconstitution of the lyophilized pellet in WFI FIG. 3 Effects of sorbitol, magnesium chloride and L-methionine on the stability of freeze-dried CHIKV at room temperature. $TCID_{50}$ assay (error bars of ±0.3 log) performed directly after reconstitution of the lyophilized pellet in WFI FIG. 4 Effects of sorbitol, magnesium chloride and L-methionine on the stability of freeze-dried CHIKV at 2-8° C. $TCID_{50}$ assay (error bars of ±0.3 log) performed directly after reconstitution of the lyophilized pellet in WFI.

The present invention provides novel formulations of CHIKV useful as vaccines and methods for their preparation. More particularly, the invention relates to stabilizing formulations for liquid and lyophilized CHIKV vaccines, Due to the worldwide distribution of vaccines, the wide variety of ambient temperatures and the requirement to produce vaccine at an affordable price, it is necessary to formulate vaccines such that they are stable under a variety of environmental conditions, incur reasonable costs and can be produced swiftly in accordance to the demand which may fluctuate substantially, e.g. during an outbreak. A variety of stabilization methods and approaches in this regard have been used. These include the following:

a) Low temperatures (−10° C. to −70° C.). Most vaccines are stable during storage at extremely low temperatures. However, low temperature storage facilities are costly and are not always available, particularly in developing countries; this limits the utility and practicality of this approach.

b) Lyophilization. Freeze-dried vaccines are reasonably stable and can be stored at 2-8° C. for a predefined length of time. Lyophilization may, however, result in a loss of viral titer during drying thereby reducing the yield of the manufacturing process or might alter sub-population of the virus in a heterogeneous virus population. A lyophilized virus vaccine is typically more stable than a liquid formulation; however, during long-term storage, the lyophilized vaccine may still deteriorate, sometimes to the point where it contains an insufficient titer to confer immunization. Furthermore, since a lyophilized vaccine requires reconstitution prior to use, a liquid reconstituted preparation may lose potency while standing at room temperature before use. This loss of titer during reconstitution may also result in insufficient titer to confer immunity.

c) Stabilizers. These are specific chemical compounds that interact with and stabilize biological molecules and/or general pharmaceutical excipients that are added to the vaccine and used in conjunction with either lower temperature storage or lyophilization methods. However their use and effectiveness is not known for a new virus and might be restricted.

These formulations can be prepared by either (1) dilution of bulk vaccine into the stabilizer. (2) dialysis/diafiltration into the stabilizer, or (3) concentration of bulk vaccine and dilution or diafiltration into the stabilizer, followed by lyophilization.

The amounts and concentrations of the components of the formulations described herein will be understood by those skilled in the art to refer to the weight/volume percentage when referring to lyophilized or liquid formulations. For example, a 10% concentration in a liquid formulation is 10 grams per 100 milliliters and a 10% concentration of a lyophilized formulation refers to 10 grams per 100 milliliters in the liquid form before lyophilization. The lyophilized formulations are reconstituted in WFI or another acceptable diluent to approximately the same volume as before lyophilisation, i.e., the concentrations in the lyophilized formulations as used herein generally refer to concentrations both before lyophilisation and after reconstitution. Other measures, such as the molarity of a compound, refer to a liquid formulation or to a lyophilized formulation both before lyophilization and after reconstitution.

The compositions of the present invention contain the respective ingredients in about the amounts indicated. For convenience, the amounts are stated in round numbers. However, one skilled in the art will recognize that amounts within 10 or 20 percent of the stated values can also be expected to be appropriate, i.e., where 20% is stated, a range of from 16-18% to 22-24%, e.g., a range of about 16-24% is implicit and can be appropriate.

In the course of the current invention, it was found that certain buffer systems, such as e.g. histidine, under certain conditions, induced aggregation of CHIKV vaccine candidates, e.g, those described herein, A low (e.g. ~5 mM) phosphate-citrate buffer system, which was shown to be amenable to lyophilisation and promoted the stability and desired size of CHIKV particles, also containing other stabilizing components, was developed for the lyophilized CHIKV vaccine formulation. A similar formulation was developed for the liquid (frozen) CHIKV vaccine.

For Liquid CHIKV Formulations:

Sucrose: 1-50% (w/v)

Sodium or potassium phosphate: 1-20 mM

Sodium succinate or sodium citrate: 1-50 mM

Human Serum Albumin: 0.001 to 1%

Tissue culture medium, saline, or water: balance of remaining volume

For Lyophilized CHIKV Formulations:

Sucrose: 1-20% (w/v)

Sodium or potassium phosphate: 1-20 mM

Sodium succinate or sodium citrate: 1-50 mM

In addition, the following can also be present:

$MgCl_2$: 1-10 mM

D-sorbitol: 0.1-5% (w/v)

L-methionine: 1-20 mM

Buffering Agents in Vaccine Formulations

An important aspect of any vaccine formulation is maintenance of a steady pH value. A buffer for the composition of the CHIKV vaccines of the current invention must not only maintain pH during storage, but must also be compatible with the necessary processing steps of the CHIKV vaccine. For example, the CHIKV vaccine must be sterile filtered after formulation; therefore, the buffering system (and other components) must not promote the formation of virus aggregates which are too large to filter. The buffer must effectively maintain the pH under a broad range of temperatures during lyophilisation. In this regard, the use of phosphate at generally used concentrations, such as 10 mM or above, may be problematic due to its concentration during freezing and subsequent possible precipitation leading to significant pH shifts, especially at higher phosphate concentrations. For this reason, alternative buffering agents were investigated, but did not result in improved stability or cake structure (data not shown). In a preferred embodiment, it was found that phosphate could be reduced to 1 to 5 mM, preferably to about 5 mM in the lyo formulation. Alternatively, HEPES buffer at a concentration of about 20 mM is also acceptable. It is preferred to use an additional buffering agent along with phosphate, preferably the additional buffering agent is a carboxylate, selected from the group consisting of succinate, citrate, fumarate, tartarate, maleate and lactate, preferably citrate. These particular carboxylates help to inhibit aggregation.

The following compounds can be used in place of sucrose, and at comparable osmolality: sucrose, mannitol, dextran, lactose, sorbitol, dextrose, fucose, and trehalose. In a preferred embodiment, sucrose and/or trehalose is used, most preferably sucrose Sucrose at 5% has been shown to protect CHIKV during freeze/thaw stress. Trehalose has the advantage of enabling the use of higher temperatures during the lyophilisation process.

The concentration of sugar relates to the viscosity of the formulation. In instances where reduced viscosity is desired, it is known in the art to be preferable to use lower concentrations of sugar, e.g., sucrose. It will also be appreciated by persons in the art that the upper limit for the concentration of sugar can be dictated by the ability of a formulation to undergo required filtration or processing steps.

Amino acids can be employed in the lyophilized formulations taught herein. It has been found that amino acids can improve the stability of a vaccine prepared in the lyophilized formulations. Preferred amino acids are L-methionine, arginine and glutamine. A concentration of about 1-20 mM is appropriate. A concentration of about 10 mM is preferred in lyophilized formulations. A combination of amino acids can be used but the overall concentration of the combined amino acids should be no more than 20 mM.

Another excipient useful in the lyophilized formulations is D-sorbitol which addition in small quantities can result in retention of protein native structure and improved stability as demonstrated for lyophilized antibodies (Chang et al. Liuquan (Lucy) Chang. Deanna Shepherd. Joanna Sun. Xiaolin (Charlie) Tang Michael J. Pikal; J. Pharm Sci. 2005 July; 94(7):1445-55. Effect of sorbitol and residual moisture on the stability of lyophilized antibodies: Implications for the mechanism of protein stabilization in the solid state) and for ribonuclease A (Xie Guifu and Timnasheff Serge. Protein Science 1997. 6. 211-221: Mechanism of the stabilization of ribonuclease A by sorbitol: Preferential hydration is greater for the denatured than for the native protein).

Another excipient useful in the lyophilized formulations is magnesium chloride which is assumed to stabilize RNA structure of CHIKV and exhibited a positive effect on infectivity after storage. A particularly useful concentration for this purpose of the invention is about 5 mM.

Another excipient useful in both liquid and lyophilized formulations of vaccines as taught herein is recombinant human serum albumin (rHSA). Recombinant human serum albumin is produced using gene expression systems and therefore is safer to use than albumin isolated from the serum of human beings. The concentration of the albumin is typically in the range of about 0.1 to about 2%, preferably about 1.0%. However, we found to be able to reduce the albumin to 0.01% which can reduce the costs considerably.

Tissue culture medium, saline or water, such as WFI or milliQ water, preferably WFI may be used as a diluent. The amount of diluent used to reconstitute the lyophilized cake may be from 0.25 to 2.5 times the volume of the formulation before lyophilisation, or 0.5 to 1.75 times, 0.75 to 1.25 times; however, there is a clear preference for reconstituting the lyophilized cake to about the same volume as before lyophilisation.

A preferred formulation of the liquid (frozen) CHIKV formulation of the present invention is as follows:

10 mM potassium phosphate
25 mM sodium citrate
5% sucrose
0.01% rHSA
pH 7.3±0.2
water In these preferred formulations, it can be appropriate to use saline or tissue culture medium in place of water.

A preferred formulation of the lyophilized formulation (concentrations refer to the formulation before lyophilisation as well as after lyophilisation and reconstitution) of the present invention is as follows:

5 mM potassium phosphate
25 mM sodium citrate
5% sucrose
0.5% D-sorbitol
10 mM L-Methionine
5 mM $MgCl_2$
0.01% rHSA
pH 7.3±0.2
water Any general method of lyophilization known in the art may be used. As a general example of a lyophilization process, freezing may be performed at −40° C., followed by primary drying in 2 steps (e.g., −35° C. for 3 hours, followed by −25° C. for 30 hours, both at 100 bar measured by Pirani). Secondary drying may be performed at 20° C. followed by a second step at 25° C. (both at 70 bar vacuum), Particularly preferred is a lyophilisation method providing an adequate cake structure, i.e., a cake without cracks and with minimal shrinkage.

The dilution factor of DS to DP bulk depends on the viral concentration of DS (determined by $TCID_{50}$ assay). Formulation buffer for DS and DP formulation are identical: 25 mM sodium citrate. 5 mM potassium phosphate. 5% sucrose. 0.01% rHSA. 10 mM L-methionine. 5 mM MgCl2. 0.5% sorbitol. pH 7.3. The target concentrations after dilution to DP are 5.8 $\log_{10}$ $TCID_{50}$/mL (=6.3×10$^5$ $TCID_{50}$/mL, DP high) and 4.8 $\log_{10}$ $TCID_{50}$/mL (=6.3×10$^4$ $TCID_{50}$/mL, DP low). This accounts for possible losses during filtration and fill/lyophilization of the vaccine at larger scale and should guarantee a final virus dose per vial of ~10$^5$ (~10$^4$) $TCID_{50}$ after freeze drying.

Figure 1:
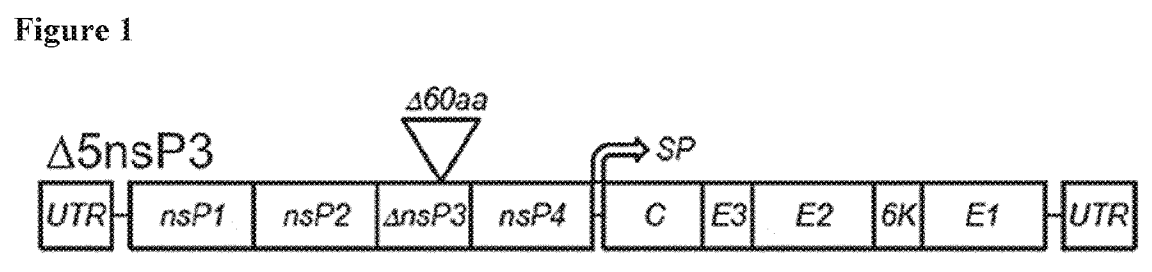

This invention involves formulations of CHIKV and in particular for attenuated live CHIKV, preferably "CHIKV-Δ5nsP3" which is the CHIKV "LR2006_OPY1" lacking a 60 amino acid stretch in the nsP3 region, also referred to herein as CHIKV-Δ5nsP3 (see Hallengärd, supra, FIG. 1 and SEQ ID NO: 1) or any functional variant of CHIKV-Δ5nsP3 with 95%, preferably 96%, 97%, 98%, 99%, most preferred 99% sequence identity, still including the deletion of said 60 aa stretch. Variants of CHIKV-Δ5nsP3 include variants in E2 of CHIKV-Δ5nsP3 with one or more mutation(s) in E168K (SEQ ID NO: 3), G55R (SEQ ID NO: 4), E247K (SEQ ID NO: 5), G82R (SEQ ID NO: 6) and/or H232Y (SEQ ID NO: 7). Variants may also include silent mutations. SEQ ID NO: 2 is the E2 wild type sequence of LR2006_OPY1. In a preferred embodiment, the mutations (e.g. the mutation E168K) in the E2 structural protein are present at a frequency of 70% or less, e.g., less than 70% of the total CHIKV-Δ5nsP3 particles comprise one or more mutations (or the mutation E168K) and 30% or more of the total CHIKV-Δ5nsP3 particles express a non-mutated E2 structural protein or an E2 structural protein that does not comprise the mutation E168K. A particularly preferred formulation comprises a population of two or more variants as described herein. An even more preferred formulation comprises a population of substantially two strains encoding for E2 amino acids sequences SEQ ID NO: 2 (wild type) and SEQ ID NO: 3 (with the E168K mutation) and wherein the E1 structural protein is unchanged, i.e. the wild type E1 protein as encoded in the genomic sequence provided by SEQ ID NO: 1. Said formulation is also referred to as a formulation comprising the "CHIKV-Δ5nsP3-inv" population, wherein the frequency is about 10% to 90% of SEQ ID NO: 2. In a more preferred embodiment, the frequency of said SEQ ID NO: 2 may be around 30 to 70%, more preferably about 50%.

Said CHIKV-Δ5nsP3 constructs, including CHIKV-Δ5nsP3-inv, that are alone or in combination suitable for use as vaccines are characterized by safety to humans and the ability to confer immune protection against CHIKV infection in humans. Interestingly, it was found that small changes to the RNA genomic sequence corresponding to the DNA sequence provided by SEQ ID NO: 1 might render certain formulations less useful for industrial use because of changes in charges that are exposed to the formulation solution.

In one embodiment, the pharmaceutical composition (herein also referred to simply as "formulation" or "vaccine", said terms can be used interchangeably in this invention) increases serum antibody titers in a vaccinated human subject by at least 1 log, relative to a control, within about 5 to 28 days. In a preferred embodiment, the pharmaceutical composition increases serum antibody titers in a vaccinated human subject by at least 1 log, relative to a control, within about 14 days. In a preferred embodiment, the pharmaceutical composition increases serum antibody titers in a vaccinated human subject by at least 1 log, relative to a control, within about 7 days. In one embodiment, said control is pre-immune sera from the same human subject; e.g., collected before vaccination. In one embodiment, said control is sera from a placebo-treated or non-vaccinated subject or subjects.

In one embodiment, the pharmaceutical composition of the invention stimulates seroconversion in at least 25%, at least 30%, at least 40%, at least 50%, at least 60%, at least 70%, at least 80%, at least 90%, at least 91%, 92%, 93%, 94%, 95%, 96%, 97%, 98%, 99%, up to 100% of vaccinated subjects within 14 days of a single vaccination. In one embodiment, the pharmaceutical composition of the invention stimulates seroconversion in at least 25%, at least 30%, at least 40%, at least 50%, at least 60%, at least 70%, at least 80%, at least 90%, at least 91%, 92%, 93%, 94%, 95%, 96%, 97%, 98%, 99%, up to 100% of vaccinated subjects within 7 days of a single vaccination. In one embodiment, seroconversion is defined as reaching a CHIKV-specific antibody titer, i.e., a neutralizing antibody titer, of at least 10. The neutralization of Chikungunya virus may be assessed in an in vitro assay, such as a $TCID_{50}$ assay and/or a neutralizing assay such as a PRNT, i.e. $PRNT_{50}$ or microtiter assay, i.e., $\mu NT_{50}$ wherein a range of serum dilutions are tested for neutralization of CHIKV growth and calculating the dilution that neutralizes 50% of growth compared with a negative control. As used herein, a PRNT50 assay gives a readout in countable plaques and a $\mu NT50$ assay gives a colorimetric readout which is proportional to cytopathic effect. The 50% reduction of CHIKV virus growth in a $TCID_{50}$ assay (or a $PRNT_{50}$ or $\mu NT_{50}$ assay) by a 1:10 or 1:20, preferably 1:20, or higher dilution of immune sera is defined herein as seroconversion. The value is reported as the reciprocal of the dilution factor, e.g., 50% CHIKV neutralization at a 1:10 immune serum dilution is referred to as a neutralizing titer of 10, or 50% CHIKV neutralization at a 1:20 immune serum dilution is referred to as a neutralizing titer of 20. As defined herein, neutralizing titer values of 10 or higher are all defined as seroconversion, with 10 being the minimum and 20 or higher being preferred.

In one embodiment, the pharmaceutical composition of the invention confers a protective immune response against CHIK virus disease, which protective immune response is long-lasting. In one embodiment, the pharmaceutical composition of the invention confers lifelong protection against CHIK virus disease. In one embodiment, the protective immune response is sustained from at least 6 months up to a lifetime, e.g., several decades, such as 10 to 70 years or beyond. In one embodiment, the protective immune response is sustained up to at least 50 years, at least 40 years, at least 30 years, at least 25 years, at least 20 years, at least 19, 18, 17, 16, 15, 14, 13, 12, 11, 10, 9, 8, 7, 6, 5, 4, 3, 2 years, at least 1 year. In a preferred embodiment, the protective immune response lasts at least 6 months, at least 12 months, at least 24 months. A protective immune response is an immune response in which neutralizing antibodies are produced which are sufficient for reducing or preventing signs or symptoms of Chikungunya virus disease.

In one embodiment, the pharmaceutical composition is suitable for use in a method of treating or preventing a Chikungunya virus infection but also include treating or preventing certain cancers. Particularly, the pharmaceutical composition is suitable for use in vaccinating a human subject and stimulating a protective immune response in said subject. In a preferred embodiment, the method of treating or preventing a Chikungunya virus infection according to the current invention comprises administering an effective amount of the pharmaceutical composition as defined herein to a subject in need thereof. A subject in need of vaccination against CHIKV according to the current disclosure can be any human subject in danger of exposure to the virus, such as a traveller to an endemic or outbreak country or an inhabitant of an endemic or outbreak country or a country in danger of an outbreak.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well known in the art. Generally, nomenclatures used in connection with, and techniques of biochemistry, enzymology, molecular and cellular biology, microbiology, virology, cell or tissue culture, genetics and protein and nucleic chemistry described herein are those well-known and commonly used in the art. The methods and techniques of the present disclosure are generally performed according to conventional methods well known in the art and as described in various general and more specific references that are cited and discussed throughout the present specification unless otherwise indicated. The formulations, such as e.g. vaccines, of this invention are particularly useful for the prevention and/or therapy of any Chikungunya infection (induced by any CHIKV strain) in humans or other susceptible animals. However, said formulations might also be useful in other indications such as e.g. cancer of any form (again in a preventative and/or therapeutic setting).

Method of Vaccination

Therefore preferred, also included in the invention is a method of vaccinating humans against human CHIKV infection with the novel CHIKV vaccine compositions of this invention. The formulations, i.e. vaccine compositions, including one or more of the attenuated live CHIKV and excipients described herein are administered, preferably by the intramuscular or subcutaneous route, in a suitable dose as determined also herein, preferably in a lyophilized (reconstituted) form to a subject.

In some embodiments, the preparations or compositions may be administered via conventional routes, such as parenterally. As used herein, "parenteral" administration includes, without limitation, subcutaneous, intracutaneous, intradermal, intravenous, intramuscular, intraarticular, intraperitoneal, intrathecal or by infusion.

The dosage for the intramuscular or subcutaneous route is proposed to be between $1\times10^3$ $TCID_{50}$/dose and $2\times10^4$ $TCID_{50}$/dose with a target such as $5.01\times10^3$ $TCID_{50}$/dose (dose, e.g. 1 ml in volume, then also $5.01\times10^3$/ml) of the attenuated CHIKV candidates herein disclosed (mixture of strains with E2 of SEQ ID NOs: 2 and E2 of SEQ ID NO: 3) and data presented herein support a one shot dosage administration for being fully protected possibly as soon as 7 days after primary vaccination, but clearly after 14 days after primary vaccination. CHIKV infection in humans has been observed to occur in various geographical regions including in the United States.

The following examples illustrate methods for preparation, usage and administration of the CHIKV vaccine formulations of the invention. These examples are illustrative only and do not limit the scope of the invention.

EXAMPLES

Example 1. CHIKV Freeze Dried (Lyo) Product Formulation Development

Definitions & Abbreviations

CHIKV Chikungunya virus
CHIKV-Δ5nsP3-inv an immunogenic mixture comprising CHIKV-Δ5nsP3 particles comprising the RNA genome corresponding to the DNA sequence provided by SEQ ID NO: 1 and CHIKV-Δ5nsP3 variants with an RNA genome at least 99% identical to the corresponding DNA sequence provided by SEQ ID NO:1, but encoding a viral polyprotein having at least one amino acid difference, preferably in the region encoding envelope protein E2 (also referred to herein as CHIKV-Δ5nsP3)
CTMA CTM Analytics & Development department
CMO Contract Manufacturing Organization
DLS Differential Light Scattering
DP Drug Product comprising CHIKV-Δ5nsP3-inv
DS Drug Substance comprising CHIKV-Δ5nsP3-inv
DSP Down Stream Process
mDSC Modulated Differential Scanning Calorimetry
GCE Genome copy equivalents
HEPES (4-(2-hydroxyethyl)-1-piperazineethanesulfonic acid)
PC Polycarbonate
PD Process Development Department
PETG Polyethylene terephthalate glycol-modified
PS Particle Size
rHSA Recombinant Human Serum Albumin
RT-qPCR Reverse Transcription—quantitative Polymerase Chain Reaction
SGP Sucrose gradient pool
$TCID_{50}$ Tissue culture infectious dose 50%
TRIS Tris(hydroxymethyl)-aminomethane
TTR Technical Transfer Run (non-GMP)
WFI Water for Injection

Materials and Methods

CHIKV Material
CHIKV-Δ5nsP3-inv with SEQ ID: 1 encoding for E2 (SEQ ID NO: 2) (including the other substantial variant CHIKV-Δ5nsP3 encoding for E2 (SEQ ID NO:3, with E1 and other expressed proteins unchanged) was produced in Vero cells and purified according to a processes described elsewhere (see WO2019057793, WO2017109223, WO2017109224). As used herein, CHIKV-Δ5nsP3-inv is also referred to herein as CHIKV-Δ5nsP3, CHIKV candidate.

Relevant experiments were conducted with representative virus material—produced in several lots—with regard to impurity profile and virus seed passage (P3).

TABLE 1

| Sucrose Gradient Pool (SGP) material. | | |
|---|---|---|
| lot # | Description | $\log_{10}$ $TCID_{50}$/mL |
| 1 | SGP | 9.0 |
| 2 | SGP | 8.8 |
| 3 | SGP | 8.0 |
| 4 | SGP | 8.4 |
| 5 | SGP | 10.0 |
| 6 | SGP | 9.8 |
| 7 | SGP | 10.0 |

$TCID_{50}$ Assay

Virus infectivity was determined by $TCID_{50}$ assay on vero cells. Virus titers were determined on Vero cells using the $TCID_{50}$ assay. Briefly, cells were seeded in microplates and infected with 10-fold serially diluted virus samples in EMEM supplemented with 0.5% FBS and 2 mM glutamine. After a one week incubation at 35° C./5% CO2, virus-induced cytopathic effects were monitored and viral titers were calculated according to the Reed and Muench method (Reed, L. J.; Muench, H. A simple method of estimating fifty percent endpoints (1938) The American Journal of Hygiene 27:493-497). Assay control samples were included in each analysis. The assay variability between individual runs was estimated as ±0.3 $\log_{10}$ $TCID_{50}$.

Dynamic Light Scattering (DLS)

Dynamic light scattering (DLS) is a technique that can be used to determine the size distribution profile of biopolymers including viral particles in solution at a size range from 1 nm to approx. 1000 nm. Since this method can be used with the native sample without any pre-treatment (e.g. no chromatography column that might filter out larger multimers/aggregates), a full picture of all particles in solution can be obtained. For DLS measurements a Malvern Zetasizer system was used. CHIKV-Δ5nsP3-inv sucrose gradient pools (~35% sucrose in Tris/NaCl) were analyzed without any pre-treatment (i.e. dilution) assuming a solution viscosity of 6.15 cP and refractive index 1.4. The virus particle refractive index was assumed as 1.45. For accurate measurement the particle concentration should not fall below a certain threshold which also depends on the size of the particles. For CHIKV-Δ5nsP3-inv the most accurate results are obtained for undiluted SGP. A comparison of representative SGP material (SGP pools in Table 1) showed a viral particle diameter of approximately 60 nm for all analyzed SGP samples (data not shown), which correlates to data referenced in literature.

Chemicals

TABLE 2

Chemicals and sources

| Chemical | Manufacturer | Order # | Quality |
|---|---|---|---|
| MgCl$_2$ * 6 H$_2$O | Merck | 105832 | Multi-compendial |
| L-Methionine | AppliChem | A1340,0100 | Ph. Eur., USP |
| K$_2$HPO$_4$ dibasic anhydrous | Sigma | RES20765-A7 | Ph. Eur. |
| | MERCK | 105101 | Ph Eur, BP, E 340 |
| KH$_2$PO$_4$ monobasic | Fluka | 04243 | Ph. Eur. |
| | MERCK | 104871 | Multi-compendial |
| Trisodium citrate dihydrate | Sigma | S1804 | Ph. Eur. |
| | Citrique belge | 04 12325 | Multi-compendial |
| | MERCK | 106432 | Eur, BP, JP, USP |
| Sucrose | J T Baker | 4005 | Ph. Eur. |
| | MERCK | 107653 | Multi-compendial |
| rHSA (20% stock solution) | Novozymes | n.a. | Ph. Eur. |
| Recombumin ® Alpha (RF20-005) | | | |
| D-Sorbitol | AppliChem | A2222,1000 | Ph. Eur., USP-NF |
| WFI | HALIX B.V. | n.a. | Ph. Eur. |

Preparation of Lyo Formulation Buffer

In short, for preparation of e.g. 5 liter formulation buffer the following procedure is applied:

Fill approximately 4.5 L of WFI into a tared glass bottle with a stirring bar

Add all buffer components under stirring:

36.8 g-Trisodium citrate dihydrate 3.13 g di-Potassium Hydrogen Phosphate 0.975 g Potassium di-Hydrogen Phosphate 250 g Sucrose 25 g Sorbitol 7.46 g L-Methionine 5.08 g Magnesium Chloride hexahydrate 2.5 mL recombinant human Albumin (20% solution)

Stir until a clear solution is obtained.

Fill up to the final volume of 5000 mL with WFI.

The density (p) of the final solution is 1.025 g/mL (20° C.). If 5000 mL are prepared the final resulting weight is 5125 g.

Freeze Dryers

Lab scale:

Lyophilization was performed on an AdVantage Pro bench top shelf tray dryer with Intellitronics Control from SP Scientific (USA):

Three shelves (total 2766 cm$^2$)

Shelf temperature: −60 to +60° C.

Lowest condenser temperature: −70° C.

Condenser capacity of 6 L

Stoppering: top-down pneumatic

Intermediate scale:

Lyophilization at an intermediate scale was performed with a Lyofast 7 freeze drier from IMA (Industria Macchine Automatiche S.p.A., Italy)

Six shelves (total 6.7 m$^2$)

Shelf temperature minimum: −55° C.

Lowest condenser temperature: −75° C.

Condenser Capacity: 148 Kg

Primary Packaging (Vials and Stoppers)

For phase I:

2R Type I plus® glass vials (Schott A G), FluroTec stoppers (West Pharmaceutical Services)

Intended primary packaging for further clinical phases (lyophilized DP):

2R Type I glass vials (Schott A G), bromobutyl stoppers (West Pharmaceutical Services)

Results

The liquid formulation buffer of Example 2 (herein, below) was chosen as a starting buffer composition for the further development of a lyophilized formulation which would ensure sterile filterability during DS and DP production:

10 mM potassium phosphate 25 mM sodium citrate

5% sucrose 0.01% rHSA pH 7.3

Most analytical data were generated by TCID$_{50}$ assay as this method not only indicates infectivity of the virus but is also used during release and stability testing. In addition, dynamic light scattering (DLS) for evaluation of the particle size and qPCR for total viral particle determination were used. Results shown in all of FIGS. 2-14 were generated using formulations of the high dose of the CHIKV vaccine.

Justification of Buffer Components

In general, the concentration of buffer ions used in freeze-dried and frozen systems must be low enough to prevent concentration effects during the freezing process, but still high enough to provide adequate buffering capacity at the desired pH. Phosphate ions are generally avoided for freeze drying purposes as concentration effects and precipitation during freezing can lead to significant pH shifts, especially at higher concentrations (Sek, D. Breaking old habits: moving away from commonly used buffers in pharmaceuticals 2012 European Pharmaceutical Review europeanpharmaceuticalreview.com/article/13699/breaking-old-habits-moving-away-from-commonly-used-buffers-in-pharmaceuticals/). Therefore Tris, HEPES and Histidine were tested alongside phosphate (4 mM, 5 mM and 10 mM) as alternative buffer components. The influence of these buffering agents on the stability of the lyophilized product in the presence of 10 mM L-methionine and 25 mM sodium citrate was assessed at 37° C., room temperature and 4° C. storage temperature. Overall, phosphate and HEPES buffer (20 mM) showed comparable stability profiles at all investigated temperatures and outperformed the other buffer compositions (data not shown). Therefore, additional experiments were performed for comparison of these two buffers: 5 mM phosphate buffer or 20 mM HEPES, both formulations including 4% Sucrose, 1% Trehalose, 10 mM L-Methionine, 2 mM EDTA), showing no significant differences in stability of the lyo CHIKV formulation over time (data not shown).

Based on the overall results it was decided to keep phosphate as buffering agent (as in the liquid frozen formulation, also together with a citrate buffer), but at the lower concentration of 5 mM to minimize buffer concentration effects and possible pH shifts during freezing.

Phosphate-Citrate Buffer: Liquid formulation buffer development for early clinical phases was aimed at 0.2 μm sterile filterability of CHIK virus during DS and DP manufacturing. A buffer system consisting of phosphate and citrate at pH 7.3 proved to stabilize the viral particle size of CHIKV and guarantees 0.2 μm filterability, which is crucial for aseptic manufacturing. To minimize possible ion concentration effects and to facilitate lyophilization, the final phosphate concentration in the lyo formulation was reduced to 5 mM.

Sucrose

During downstream processing, a sucrose gradient centrifugation is performed for final concentration and polishing of the CHIKV material, resulting in a sucrose concentration of approximately 35% in the sucrose gradient pool (SGP). As sucrose is a well-known stabilizer during freezing of biological material and also serves as a bulking material, it was kept in the formulation buffer for the freeze dried product. Sucrose at 5% has been shown to protect CHIKV during freeze/thaw stress. By subsequent dilution of SGP to DS (currently 1:60) and DP with formulation buffer a final sucrose concentration of 5% is obtained.

Recombinant Human Albumin

The concentration of rHSA was kept constant for the lyophilized product compared to the liquid formulation at a level of 0.01% (0.1 mg/mL). The incorporation of a minimal amount of rHSA is desired to prevent unspecific adsorption to surfaces of containers. Additionally rHSA at this concentration does not adversely affect the sterile filterability of the CHIKV nor the stability of the freeze dried product.

After these initial studies, the basic formulation of the lyophilized formulation ("basic lyo") was:

5 mM potassium phosphate
    25 mM sodium citrate
    5% sucrose
    0.01% rHSA
    pH 7.3

Additional excipients tested for improved stability of the lyo formulation:

D-Sorbitol

Figure 3:
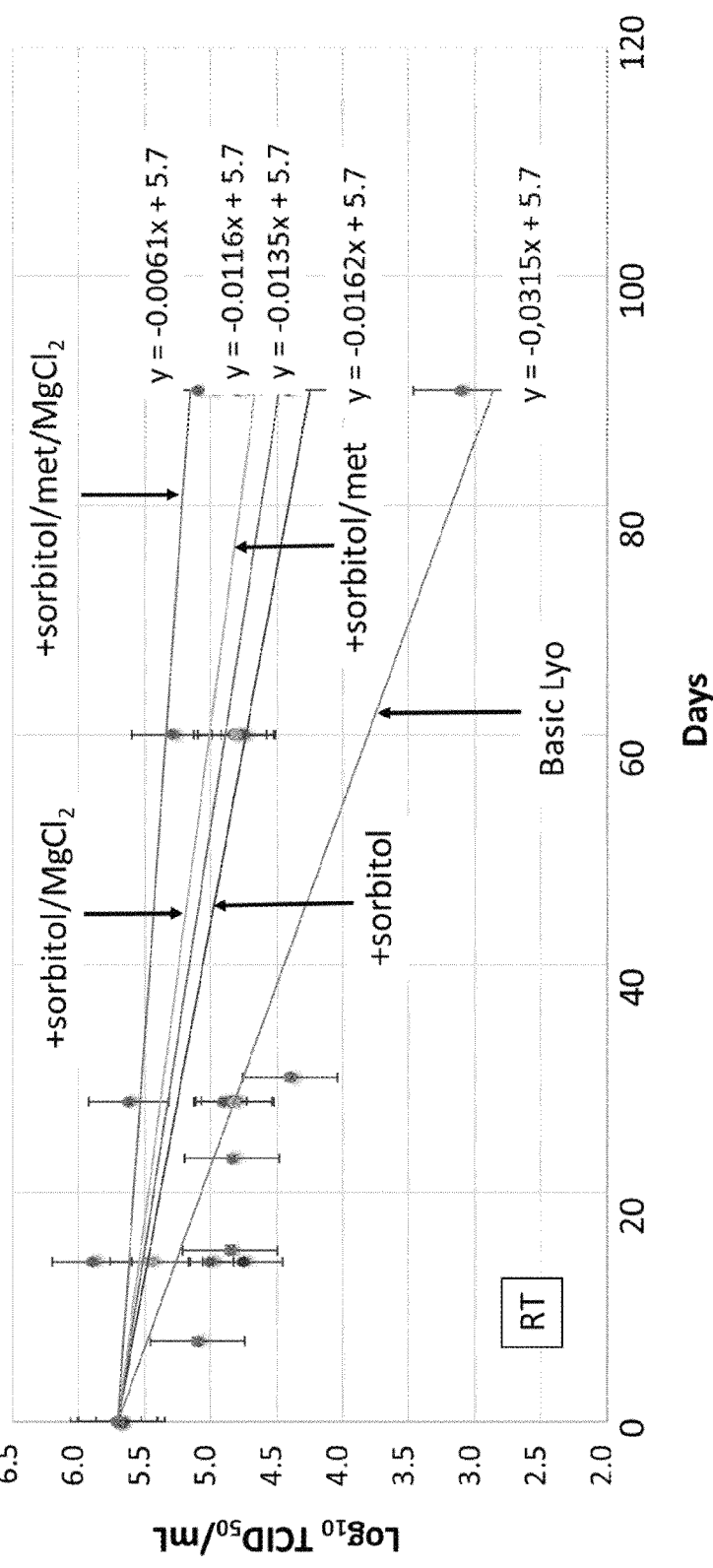
Figure 4:
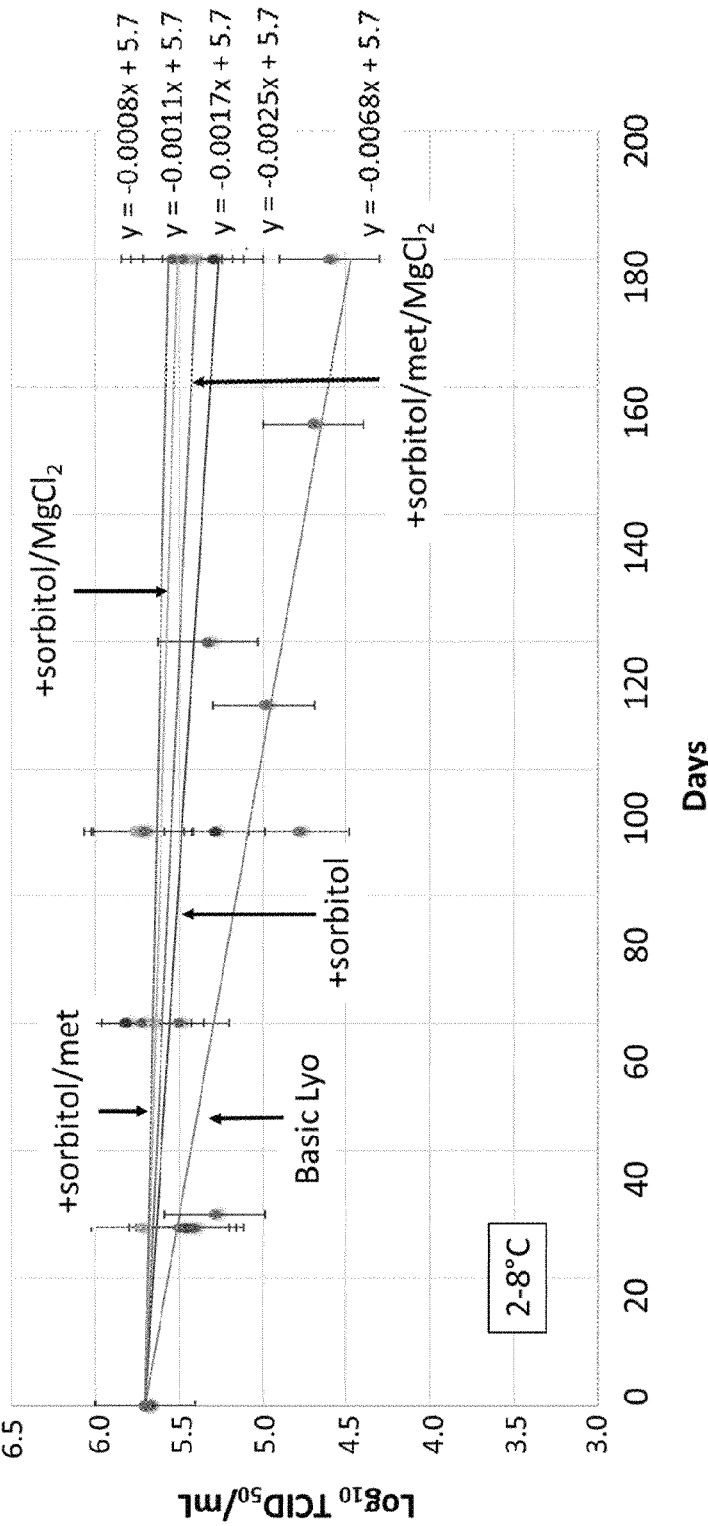

Lyophilization of CHIKV-Δ5nsP3-inv in the basic lyo buffer showed insufficient stability in the freeze dried state (see FIGS. 2-4). The addition of sorbitol alone exhibited a significant improvement of stability, especially under accelerated storage conditions (37° C., RT; FIGS. 2 and 3, respectively). A positive stabilizing effect of sorbitol on CHIKV was observed for all exploratory formulations tested during development. As sucrose alone already exhibits a rather low collapse temperature ($T_C$) of –32° C. during freeze drying, the concentration of sorbitol ($T_C$ –45° C.) was set to 0.5% to prevent an additional significant decrease of the overall $T_C$ but providing significant stabilization of the freeze dried product.

Magnesium Chloride

Magnesium chloride is assumed to stabilize the RNA structure of CHIKV and exhibited a positive effect on infectivity after storage (FIGS. 2-4). It is incorporated into the lyo formulation buffer at a concentration of 5 mM.

L-Methionine

L-Methionine is regarded as an oxidant scavenger applied in protein formulations. When added at a final concentration of 10 mM it increased stability during storage at 2-8° C. (FIG. 4) and more pronounced at accelerated temperatures (37° C., RT; FIGS. 2 and 3, respectively).

Effect of Excipients on CHIKV Stability in the Freeze Dried State

Positive effects the stability of freeze dried CHIKV-Δ5nsP3-inv of addition to the basic lyo formulation of sorbitol (0.5%), magnesium chloride (5 mM) and L-methionine (10 mM) and combinations thereof at various temperatures (37° C., RT and 2-8° C.) are summarized in FIGS. 2-4, respectively (as assessed by $TCID_{50}$ over days of storage). The one-by-one addition of the respective additives to this basic buffer is indicated in the graphs. As starting point the theoretical $TCID_{50}$ value after dilution to DP concentration (5.7 $\log_{10}$ $TCID_{50}$/mL) was assumed for all formulations.

Compared to lyophilization of CHIKV-Δ5nsP3-inv in basic lyo formulation buffer, a significant stabilization by addition of sorbitol alone and especially in combination with L-methionine and magnesium chloride was observed under accelerated conditions.

At 37° C., the loss of infectivity improved from approximately 3 $\log_{10}$ to 1 $\log_{10}$ per month and at room temperature from approximately 1 $\log_{10}$ to 0.2 $\log_{10}$ per month. When CHIKV-Δ5nsP3-inv was lyophilized in basic lyo formulation buffer without the addition of sorbitol, $MgCl_2$ or L-methionine and stored at 2-8° C. (FIG. 4), a significant difference could be observed (approximately 1 $\log_{10}$ loss after half a year) compared to the other formulations.

Subsequent testing of lyophilized CHIKV was performed in lyophilization buffer (also referred to herein as freeze drying formulation buffer and lyo buffer) as follows:

5 mM potassium phosphate
    25 mM sodium citrate
    5% sucrose
    0.01% rHSA
    5 mM $MgCl_2$
    0.5% D-sorbitol
    10 mM L-methionine
    pH 7.3

Comparison of CHIKV Before and After Freeze Drying

Dynamic Light Scattering (DLS)

Figure 5:
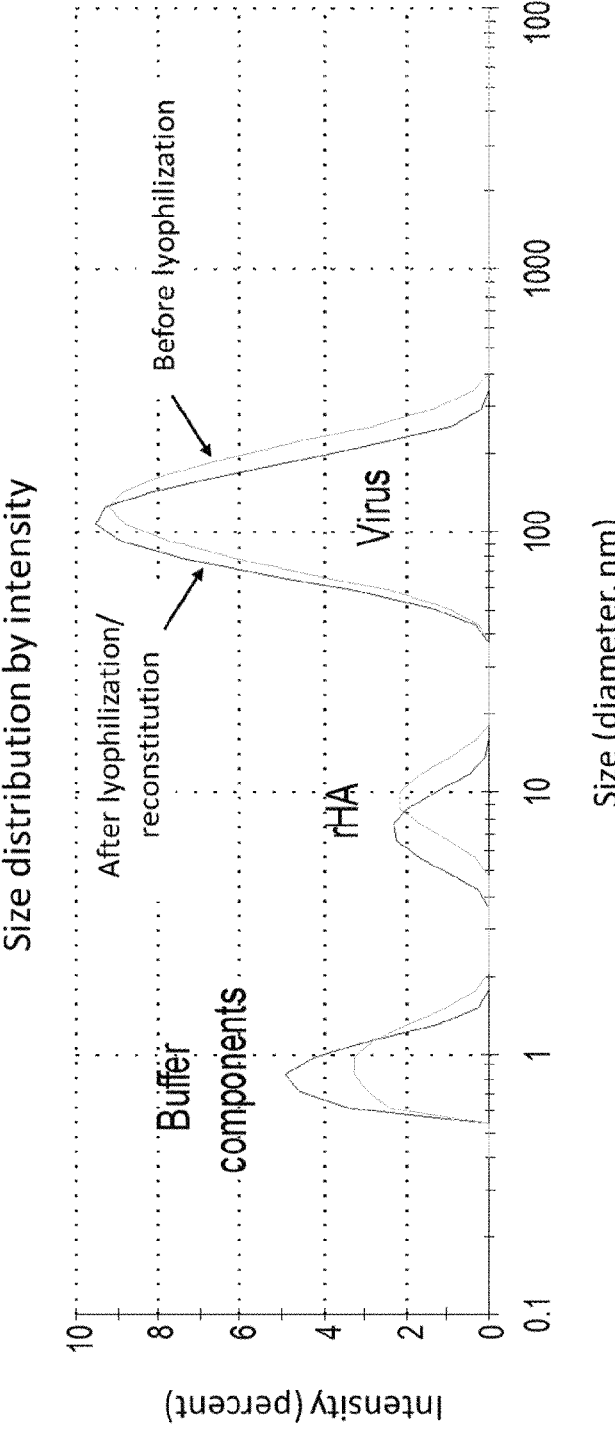
FIG. 5 Overlay of DLS signals obtained from High dose DS before lyophilization and after lyophilization/reconstitution.

The exact size of CHIKV can only be determined in concentrated samples (e.g. SGP) due to signal interference with buffer excipients (e.g. rHSA) at lower virus content. Comparative results are obtainable for samples diluted in lyo formulation buffer (containing rHSA) as long as the virus concentration is high enough. Therefore, Lot 1 SGP (9.0 $\log_{10}$ $TCID_{50}$/mL) was diluted 1:40 in freeze drying formulation buffer resulting in a virus concentration of approximately 7.4 $\log_{10}$ $TCID_{50}$/mL. This material was measured by DLS both before lyophilization and after lyophilization/reconstitution of the freeze dried virus (FIG. 5). The determined virus size before freeze drying (135 nm) and after reconstitution (118 nm) were comparable.

Plaque Assay/RT-qPCR

When propagated in host cells, CHIKV show minor genetic heterogeneities at defined positions in the RNA genomic sequence, resulting in different populations of virus in any given preparation. Some of these defined heterogeneities are characterized by reduced immunogenicity of the virus (e.g., an E168K point mutation in the CHIKV E2 protein). Therefore, it was important to identify any potential change of virus composition due to different stability profiles of the individual viral genetic populations during lyophilization.

Figure 6:
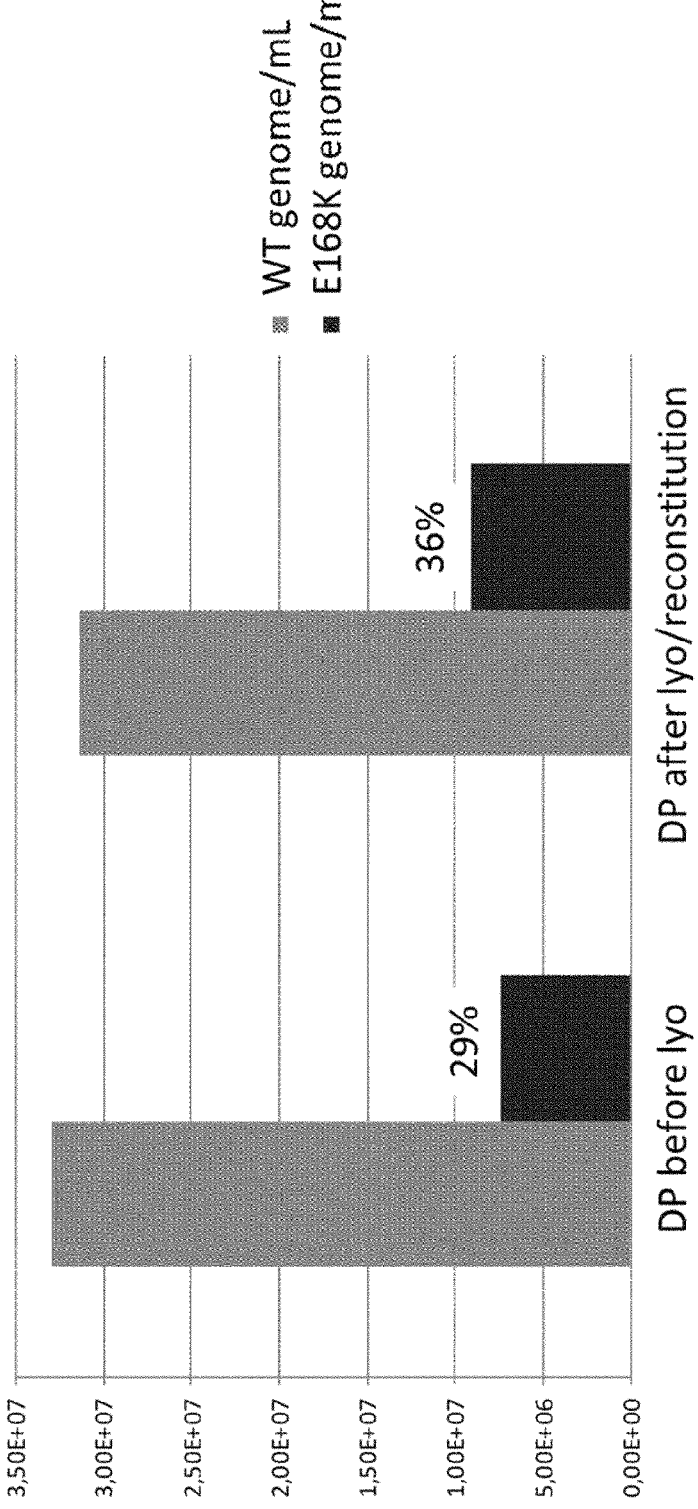
FIG. 6 RT-qPCR data of DP before lyophilization and after lyophilization/reconstitution in WFI. WT sequence in the respective region compared to E168K mutation.

DP with a nominal concentration of 5.7 $\log_{10}$ TCID$_{50}$/mL was prepared from Lot 3 SGP by dilution in lyophilization buffer and subsequent freeze drying. Samples were taken before (5.69 $\log_{10}$ TCID$_{50}$/mL) and after lyophilization (5.61 $\log_{10}$ TCID$_{50}$/mL) and analyzed in a plaque assay to determine plaque morphology (data not shown) and by RT-qPCR for quantification of E168K heterogeneity compared to the wild type sequence of the respective region (FIG. 6). Lyophilization and reconstitution had no substantial effect on the ratio of the two populations.

CHIKV Stability Lyophilized DP

CHIKV Material

Relevant experiments (n=4) summarized in this report were conducted with representative DP material. Table 3 below summarizes the investigated DP formulations and the CHIKV material used, which included both lab and intermediate scale (TTR) formulations.

TABLE 3

| Residual moisture content of lab and intermediate (technical transfer) scale lyophilized DP. | |
|---|---|
| Run | Residual Moisture % |
| Lab Scale Run F59B | 1.7 |
| Lab Scale Run F72 | 1.4 |
| TTR2 intermediate scale | 1.7 |
| TTR3 intermediate scale | 1.6 |

Figure 7:
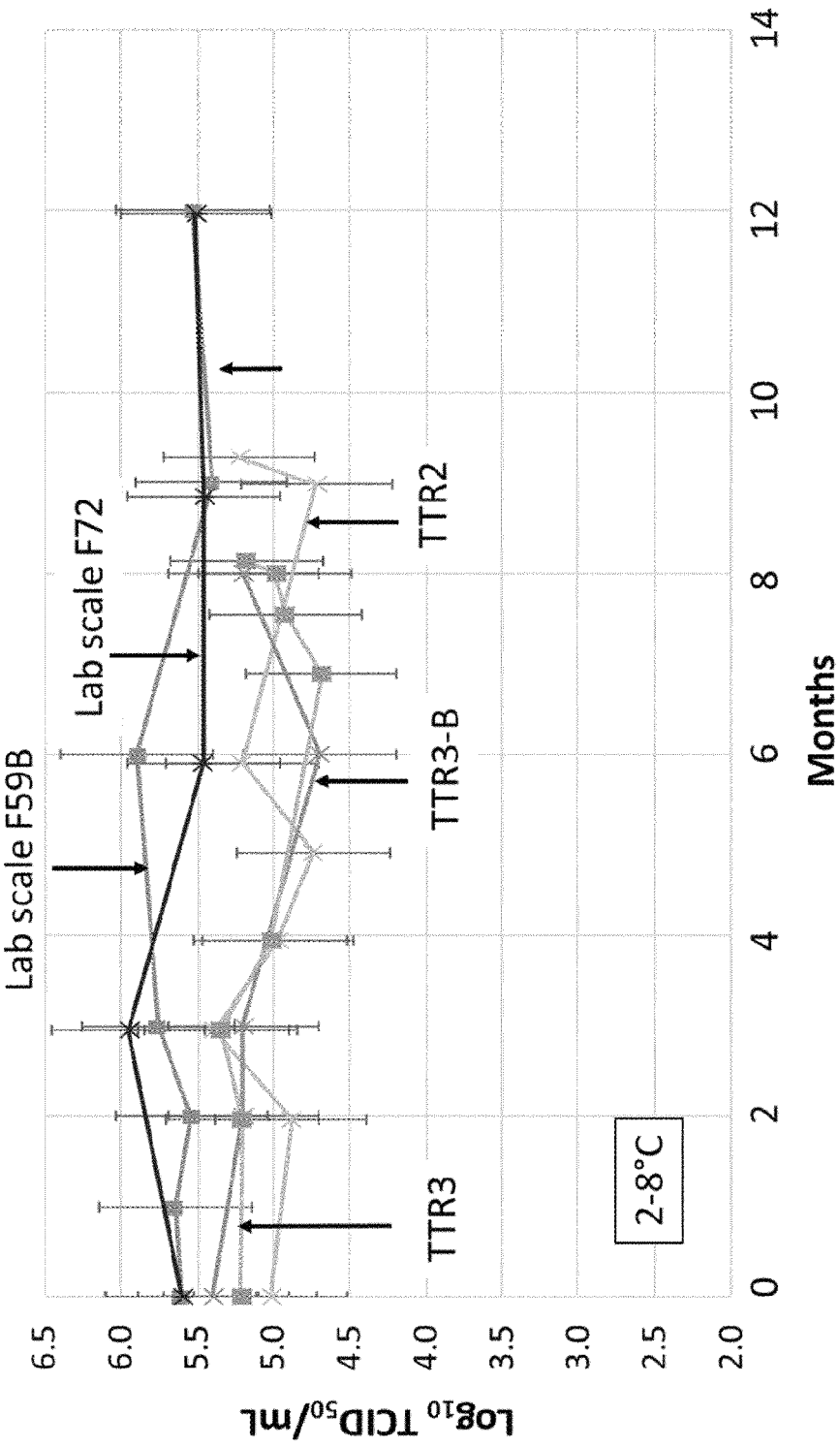
FIG. 7 Stability of lyophilized CHIKV DP formulations at lab and intermediate (tech transfer) scales at 2-8° C. Results of $TCID_{50}$ assay (error bars of ±0.5 log) performed directly after reconstitution in WFI.
Figure 24:
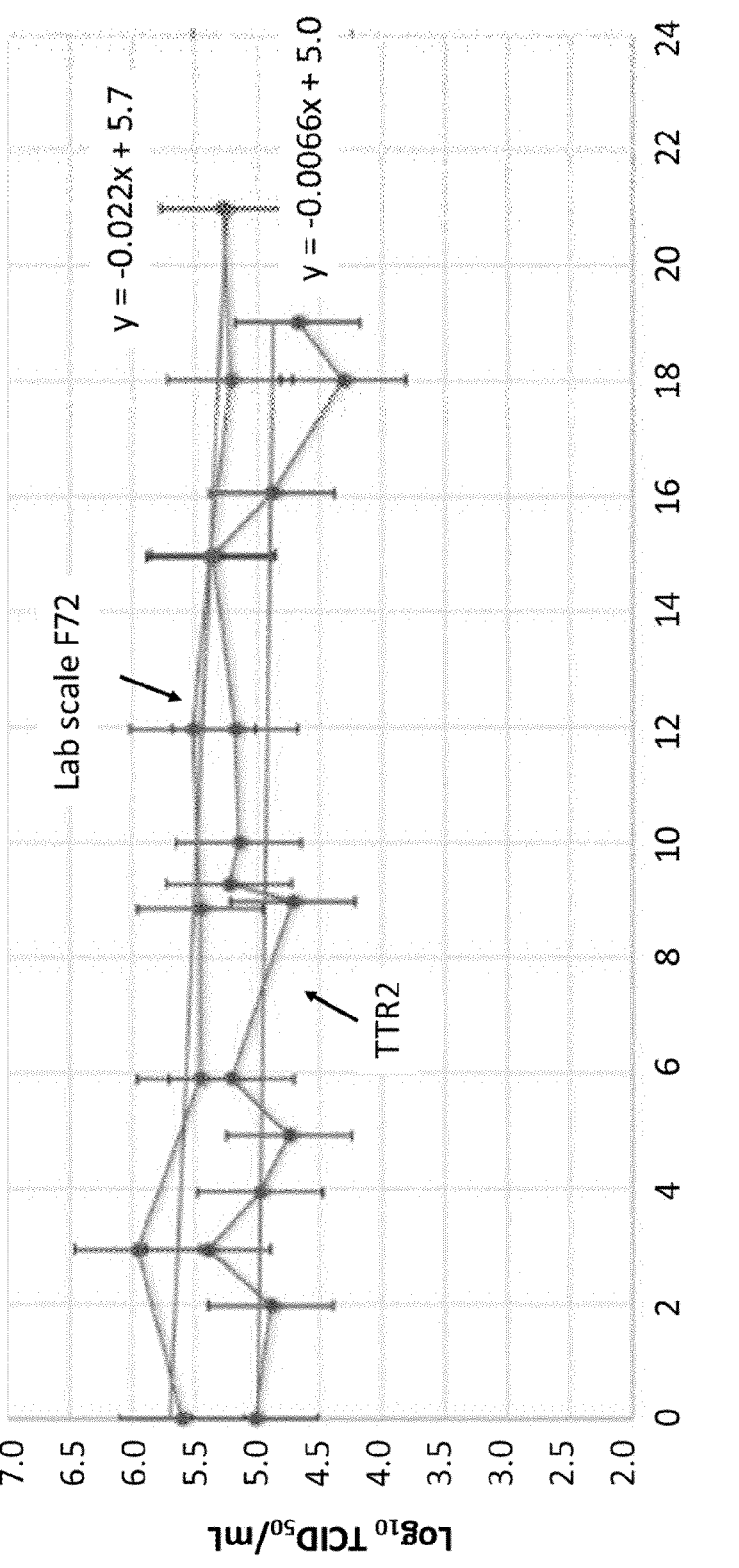
FIG. 24 Stability comparison of lyophilized DP produced at intermediate (technical transfer) and lab scales at 2-8° C. storage up to 19 and 21 months, respectively, as assessed by $TCID_{50}$ at each timepoint directly after reconstitution in WFI.

The standard storage condition of lyophilized CHIKV DP is 2-8° C. FIG. 7 shows stability data of different lots, i.e. TTR2, TTR3, F59B and F72, stored at 2-8° C. Data are shown as $\log_{10}$ TCID$_{50}$/mL values. Longer stability data are available for Lab sample F72 (21 months) and TTR2 (19 months) (see FIG. 24). As expected, the titer loss of the lyophilized formulation at refrigerated temperatures was minimal.

Figure 8:
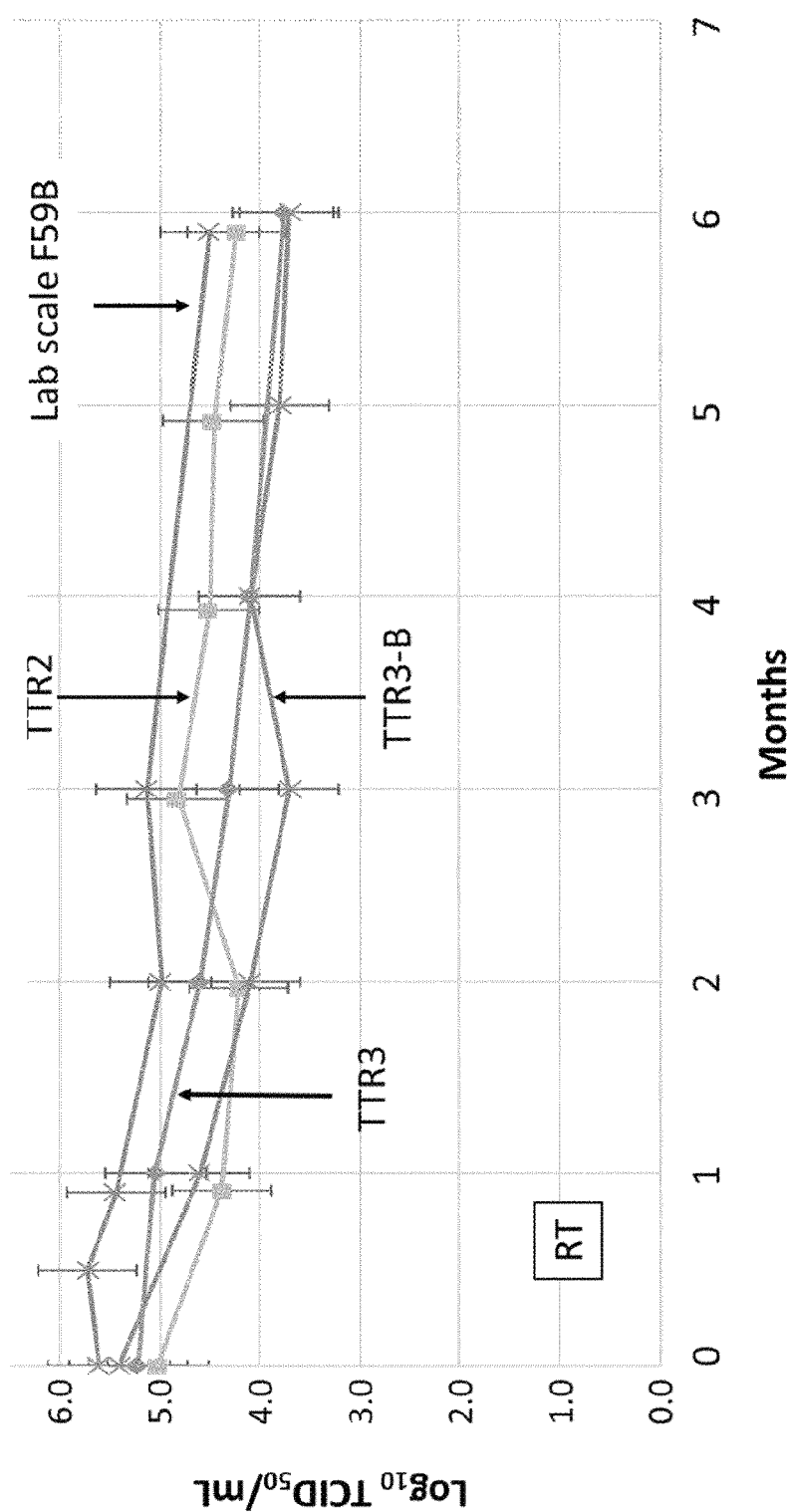
FIG. 8 Stability of lyophilized CHIKV DP formulations at lab and intermediate (tech transfer) scales at room temperature. $TCID_{50}$ assay (error bars of ±0.5 log) performed directly after reconstitution in WFI.
Figure 9:
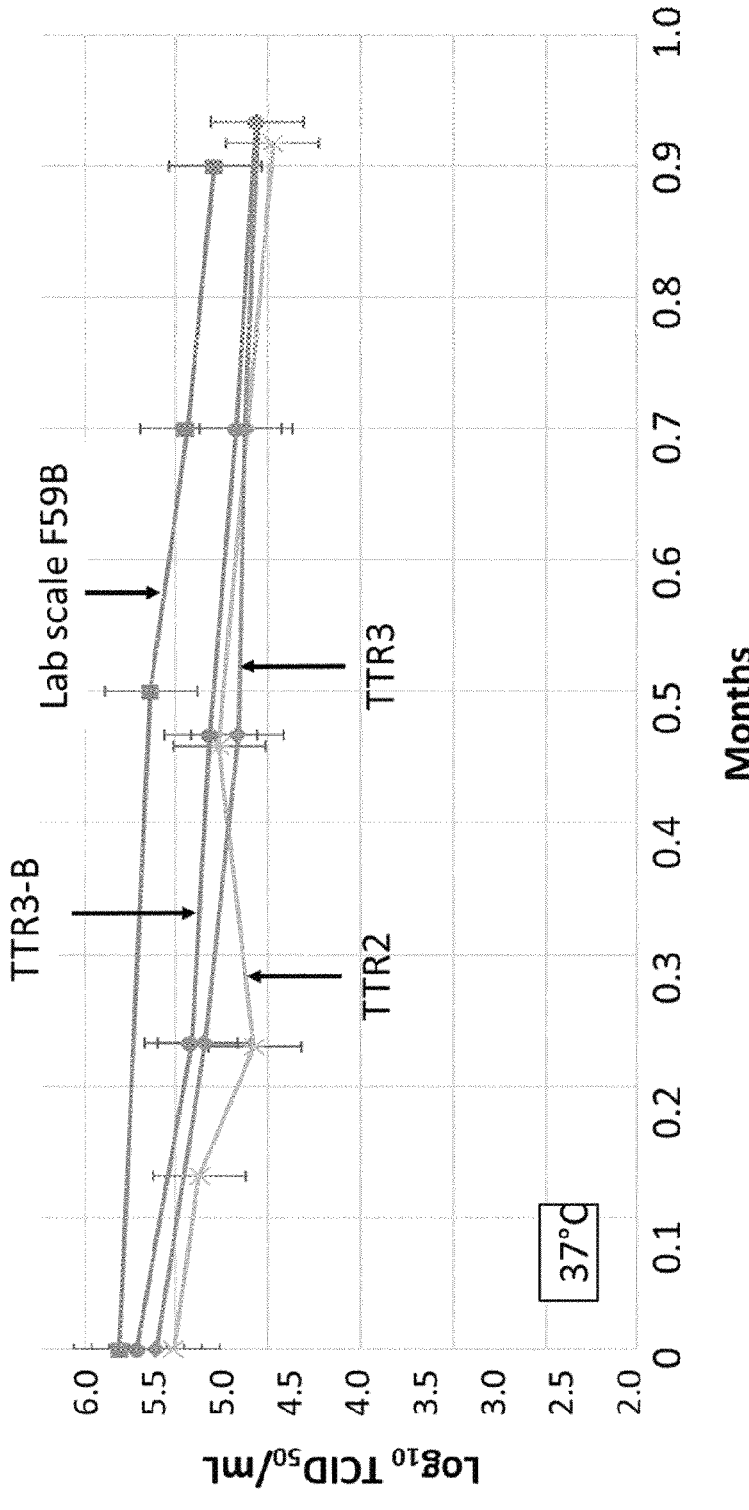
FIG. 9 Stability of lyophilized CHIKV DP formulations at lab and intermediate (tech transfer) scales at 37° C. $TCID_{50}$ assay (error bars of ±0.5 log) performed directly after reconstitution in WFI.

Accelerated stability studies conducted by the incubation of samples at elevated temperatures provides information with respect to stability differences within a shorter time frame. FIG. 8 shows stability data of TTR2, TTR3 and F59B stored at room temperature. The stability of TTR3 was also assess in parallel by a different internal department as a further control (TTR3-B). FIG. 9 depicts the stability data of the same formulations at 37° C. All data represent $\log_{10}$ TCID$_{50}$/mL values as assessed directly after reconstitution.

Figure 25:
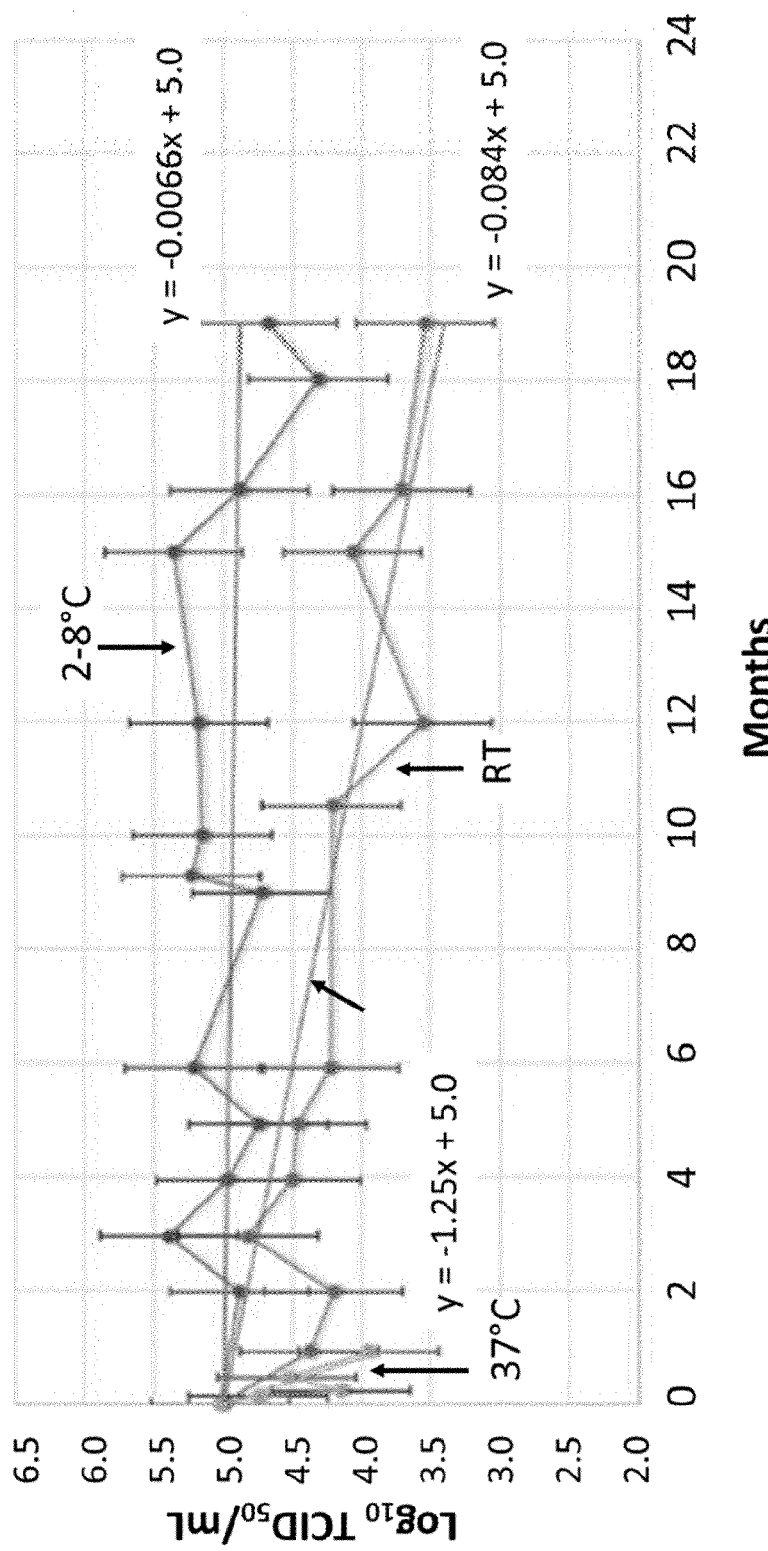
FIG. 25 Stability of lyophilized DP produced at intermediate scale (technical transfer; TTR2) at 2-8° C., room temperature (RT) and 37° C., as assessed by $TCID_{50}$ at each timepoint directly after reconstitution in WFI.

At both accelerated storage temperatures, no significant differences between lab and intermediate scale material were observed. At 37° C., the loss of infectivity was approximately 1 $\log_{10}$ per month and at room temperature approximately 1 $\log_{10}$ in 6 months. Results from a longer study with one of the intermediate scale samples (TTR2) comparing stability at all three temperatures indicated good stability at 2-8° C. up to 19 months (FIG. 25).

To illustrate the influence of TCID$_{50}$ assay variability on the predictability of long term stability at 2-8° C. a lab scale formulation is shown in Table 4.

CHIKV-Δ5nsP3-inv showed excellent stability at 2-8° C. and room temperature based on the currently available data for lab and intermediate scales. An acceptable loss of infectivity of approximately 1 $\log_{10}$ TCID$_{50}$/mL was observed when stored for 28 days at 37° C. Studies are currently ongoing to confirm long-term storage stability of CHIKV-Δ5nsP3-inv at 2-8° C. with an anticipated stability profile of less than 1 $\log_{10}$ TCID$_{50}$/mL loss after two years storage.

It should also be noted that slight variations of lyophilization parameters (e.g., temperature and duration during primary and secondary drying) did not significantly alter the stability profile of CHIKV-Δ5nsP3-inv after lyophilization at various storage temperatures (data not shown).

Overall conclusion on stability of the CHIKV lyo formulation: Loss of infectivity over time when batches were stored at 2-8° C. was minimal considering a potential TCID$_{50}$ assay variability of 0.3 $\log_{10}$. In other words, significant differences at 2-8° C. may be better assessed after long term storage. Extrapolation of stability up to two years based on the existing data estimates a loss in infectivity of up to 1 $\log_{10}$ TCID$_{50}$/mL at 2-8° C.

Stability data generated at accelerated temperatures provides information on stability differences between batches in a shorter time frame. In this regard, no significant differences between lyophilized DP derived from lab and intermediate scale were observed from studies carried out at 25° C. and 37° C. Based on the data obtained, the loss of infectivity at 37° C. is approximately 1 $\log_{10}$ TCID$_{50}$/mL per month and at 25° C. approximately 1 $\log_{10}$ TCID$_{50}$/mL in 6 months.

Example 2. CHIKV Liquid Frozen Formulation Development

During the development of the Chikungunya vaccine candidate CHIKV-Δ5nsP3-inv, the generation of specific mutations in the virus genome could be observed in response to the adaption required for growing on Vero cells (see also WO2019057793, which is incorporated herein by reference in its entirety). One of these mutations is located in the structural E2 protein at position 168, changing a glutamic acid residue to lysine (E168K). This mutation is the dominant phenotype in later passages on vero cells (P6 and higher) and correlated with a loss of immunogenicity of the attenuated CHIKV in the mouse model. To reduce the risk of producing non-immunogenic batches, a virus master bank was generated as P1 and a working bank as P2, resulting in production passage P3. Interestingly, it was found that different virus passages need different buffer compositions with regard to stability and degradation effects, apparently due to different surface charges introduced by mutations.

Most of the initial formulation development work was done using Passage 8 material. The following formulation was developed:

TABLE 4

Stability results (TCID$_{50}$) of lyophilized DP at 2-8° C., RT and 37° C.

| | Log$_{10}$ TCID$_{50}$/mL Days | | | | | | | | | | |
|---|---|---|---|---|---|---|---|---|---|---|---|
| | 0 | 14 | 21 | 28 | 60 | 90 | 120 | 150 | 180 | 270 | 365 |
| 2-8° C. | 5.7 | n.a. | n.a. | 5.5 | 5.5 | 5.7 | 5.3 | n.a. | 5.5 | 5.7 | 5.3 |
| RT (22° C.) | | 5.9 | n.a. | 5.6 | 5.3 | 5.1 | 4.8 | n.a. | n.a. | n.a. | n.a. |
| 37° C. | | 5.0 | 5.0 | 4.7 | n.a. | n.a. | n.a. | n.a. | n.a. | n.a. | n.a. |

20

The optimal pH range is 6.5 to 7.3 with higher stability at lower pH

Human Serum Albumin (rHSA) is required at concentrations of between 0.01-1%

Sucrose is needed to improve freeze/thaw stability (5% final concentration)

Histidine is best buffering compound (20 mM final concentration)

Composition of Initial Liquid Formulation Buffer:

20 mM Histidine pH 6.8, 5% sucrose, 0.1% rHSA

Additionally, during initial development, buffers were prepared with MilliQ water of high purity. However, when Passage 3 (P3) material was diluted using the same formulation buffer but prepared in water for injection (WFI), it was found that this virus passage was not compatible with the buffer any more. Upon dilution the virus size increased immediately (larger than 200 nm in diameter) most probably because of aggregation. This virus solution was therefore not sterile filterable (0.2 μm filter) which is a prerequisite for vaccine production. Phosphate-citrate buffering systems have been reported to be compatible with CHIKV VLPs (Richard Schwartz, Formulation and Stability of a Chikungunya Virus-Like Particle (ChikV VLP) Based Vaccine" in "Vaccine Technology IV", B. Buckland, University College London, UK; J. Aunins, Janis Biologics, LLC; P. Alves, ITQB/IBET; K. Jansen, Wyeth Vaccine Research Eds, ECI Symposium Series, (2013). dc.engconfintl.org/vaccine_iv/17).

Therefore, the following phosphate-citrate buffered formulation was developed, guided by extensive previous experience with the histidine-buffered CHIKV formulation, and evaluated for its suitability to formulate CHIKV and to ensure sterile filterability during DS and DP production:

10 mM potassium phosphate 25 mM sodium citrate

5% sucrose 0.01% rHSA pH 7.3

The useful concentration range of its components was investigated and is summarized in the following sections. As the final rHSA concentration was not fixed in most experiments 0.02% rHSA was chosen at the beginning to prevent unspecific adsorption at surfaces. Most analytical data were generated by DLS as this method provides a fast evaluation of the particle size, which is critical for filterability.

Influence of Phosphate Concentration

Figure 10:
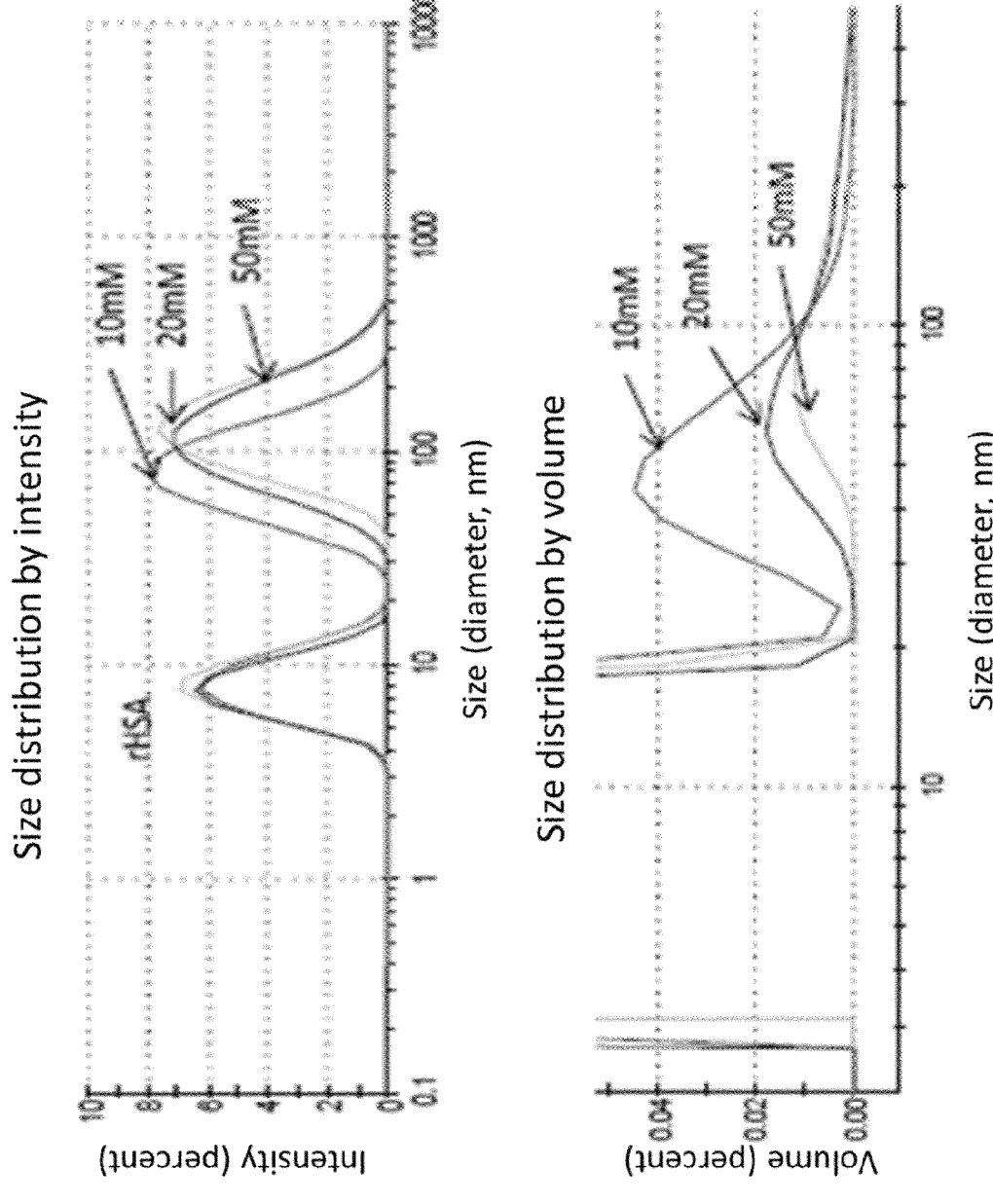
FIG. 10 Influence of increasing phosphate concentration on CHIKV size in the liquid frozen formulation as assessed by DLS.

The buffering component—potassium phosphate—was tested in the range of 10 to 50 mM. As shown in FIG. 10, the DLS data generated indicated that higher phosphate concentrations led to an increase in particle size of CHIKV-Δ5nsP3-inv (~90 nm at 10 mM to ~140 nm at 50 mM phosphate). A concentration of 10 mM was chosed for phosphate.

Influence of NaCl Concentration in Phosphate Buffered Solution

Figure 11:
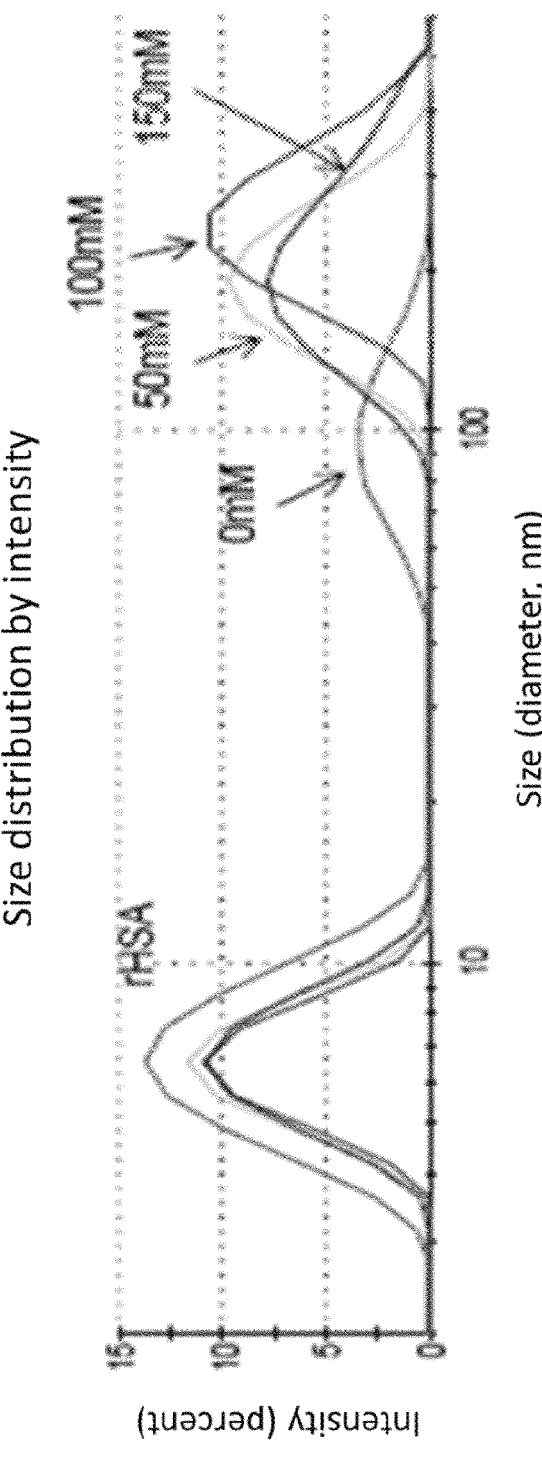
FIG. 11 Influence of increasing NaCl concentration on CHIKV size in the liquid (frozen) formulation as assessed by DLS.

In order to evaluate if sodium chloride exhibits a similar effect as citrate with regard to virus size, it was investigate between 0 and 150 mM (no citrate present). All measurements were done within 15 minutes after addition of SGP to the buffer. FIG. 11 clearly shows that NaCl in phosphate buffered solution significantly increases the virus size from approximately 100 nm (no NaCl) to ~200 nm at 150 mM NaCl. Therefore, NaCl was not further investigated and was excluded as an additional excipient.

Influence of Citrate Concentration

Figure 12:
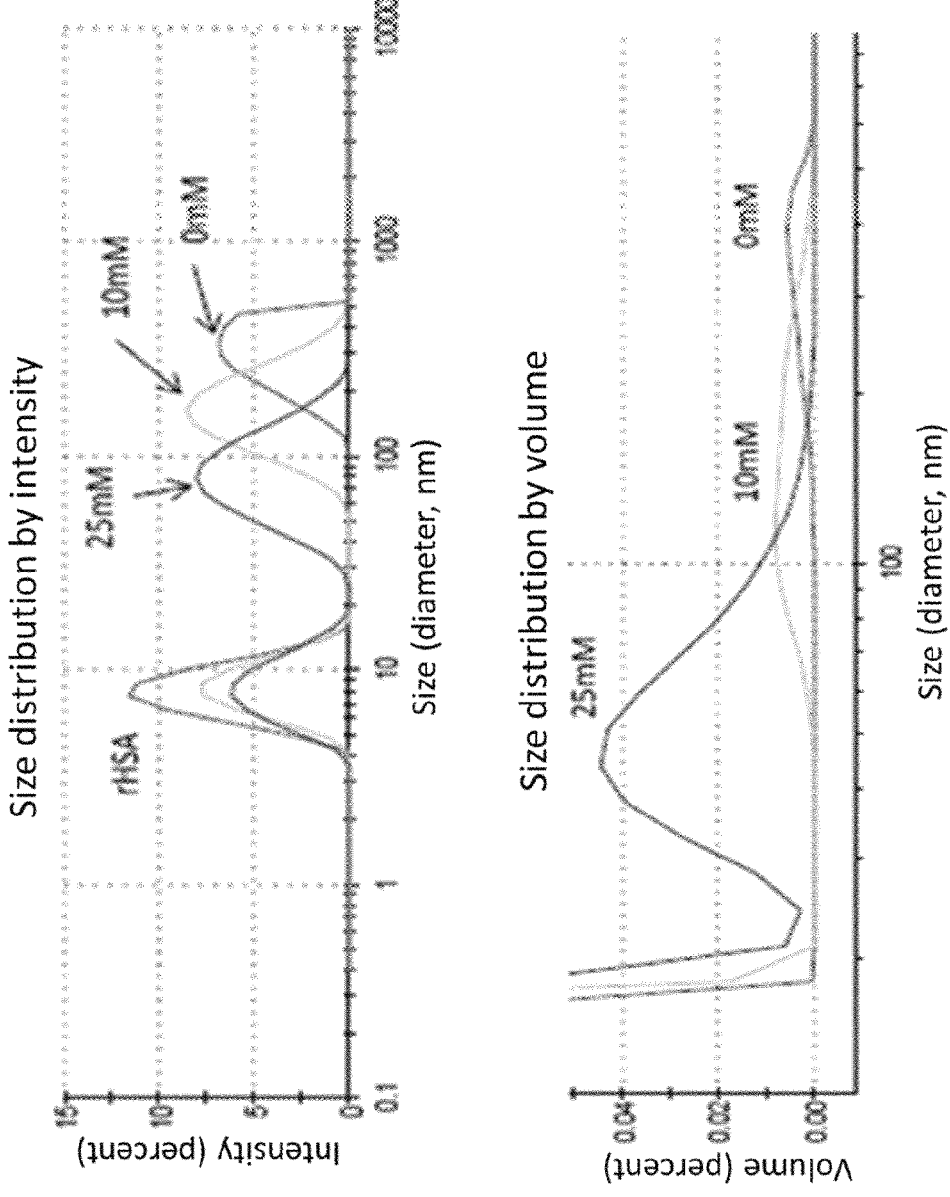
FIG. 12 Influence of increasing citrate concentration on CHIKV size in the liquid (frozen) formulation as assessed by DLS.

Citrate has been reported to inhibit aggregation of CHIKV VLPs (Kramer R M, et al. Development of a Stable Virus-Like Particle Vaccine Formulation against Chikungunya Virus and Investigation of the Effects of Polyanions. 2013 J Pharm Sci. 102(12): 4305-4314. doi:10.1002/jps.23749). Reasoning that whole CHIK virus particles may behave similarly in solution to CHIKV VLPs, different concentrations of citrate were tested to evaluate its influence on virus size. Indeed, a significant and dose-dependent reduction in particle size was observed by addition of citrate (FIG. 12). Virus in phosphate formulation buffer without citrate showed a size of ~300 nm compared to ~90 nm with 25 mM citrate. Therefore, the citrate concentration was fixed at 25 mM in the formulation buffer to keep the virus size as small as possible to facilitate 0.2 μm sterile filtration.

Influence of pH

Depending on the extent of mutations of viral proteins, the charges presented at the surface might change. With respect to this changed surface charge, also pH changes might significantly change the aggregation behavior of the virus. pH was investigated in the range of 7.0 to 7.6 (10 mM potassium phosphate, 25 mM sodium citrate, 5% sucrose, 0.02% rHSA). The influence of pH changes in this range seems not to be significant regarding the particle size with approximately 100 nm (data not shown).

Influence of Other Additives

Various additional buffer additives were investigated for potential stabilizing effects on CHIKV-Δ5nsP3-inv size:

10 mM $CaCl_2$)

10 mM $MgCl_2$ 5 mM EDTA 25 mM KCl 25 mM alanine 2.5% sorbitol

Components were added at the indicated concentrations to the formulation buffer (10 mM $PO_4$, 25 mM citrate, 5% sucrose, 0.02% rHSA, pH 7.3). DLS measurement was performed within 30 minutes after virus addition. No major influences on CHIKV diameter caused by the different buffer additives were observed compared to the original buffer (data not shown). As CHIKV diameter was already stable in the basic formulation buffer, no further advantages of the incorporation of these additional excipients could be determined. Apart from that, also no negative effect was determined. Therefore, the buffer additives tested represent an opportunity if further components are needed within the formulation buffer system for later CHIKV formulation optimization.

Influence of rHSA

In order to evaluate which effect rHSA exerts on CHIKV-Δ5nsP3-inv size, different amounts of rHSA (0-0.1%) were added to the formulation buffer (10 mM potassium phosphate, 25 mM sodium citrate, 5% sucrose, pH 7.3) and measured by DLS immediately after virus addition (SGP, 1:40 in respective buffer). Increasing rHSA concentrations caused CHIKV aggregation from 79 nm (without rHSA) to >250 nm in diameter (0.1% rHSA). The same result was observed when analyzing DLS data for size distribution by volume. Observed CHIKV diameters at the respective rHSA concentrations are listed in Table 5. The effect of rHSA on CHIKV diameters over time is shown in Table 6.

TABLE 5

Influence of rHSA on CHIKV-Δ5nsP3-inv diameter (size distribution by intensity).

| rHSA (%) | CHIKV Diameter (nm) |
|---|---|
| 0 | 79 |
| 0.01 | 141 |

TABLE 5-continued

Influence of rHSA on CHIKV-Δ5nsP3-inv
diameter (size distribution by intensity).

| rHSA (%) | CHIKV Diameter (nm) |
|----------|---------------------|
| 0.02 | 203 |
| 0.05 | 188 |
| 0.1 | 266 |

Based on these data, it was concluded that an rHSA concentration up to 0.01% is still suitable for 0.2 μm filtration, whereas rHSA concentrations ≥0.02% would lead to significant losses of virus during sterile filtration.

The incorporation of a minimal amount of rHSA is desired to prevent unspecific adsorption to surfaces of containers. Therefore, 0.01% rHSA in the formulation buffer is desirable and may be present without significantly reducing recovery during 0.2 μm sterile filtration of DS or DP as virus diameter is still below 200 nm.

TABLE 6

CHIKV-Δ5nsP3-inv diameter at different
rHSA concentrations over time.

| | CHIKV Diameter (nm) | | |
|---------|---------|-------------|------------|
| Time (h) | 0% rHSA | 0.01% rHSA | 0.1% rHSA |
| 0 | 79 | 141 | 266 |
| 2 | 87 | 149 | 434 |
| 3 | 99 | 153 | 499 |
| 22 | 94 | 175 | 459 |

Therefore, the rHSA concentration present in the formulation buffer was set to 0.01%, resulting in the following buffer composition for the liquid (frozen) formulation:
    10 mM potassium phosphate
    25 mM sodium citrate
    5% sucrose
    0.01% rHSA
    pH 7.3
Stability Studies of DS and DP
    Buffer: 10 mM potassium phosphate ($K_2HPO_4$ and $KH_2PO_4$), 25 mM sodium citrate ($Na_3C_6H_5O_7$), 5% sucrose, 0.01% rHSA, pH 7.3 (conductivity 6.0 mS/cm). Before usage, formulation buffer was 0.2 μm sterile filtered. SGP-lot was diluted 1:40 in this buffer (195 mL buffer+5 mL SGP lot) stirred for 3 minutes and left at RT for 15 minutes (to simulate later manufacturing process in larger scale). Thereafter, virus solution was 0.2 μm filtered (PALL Mini Kleenpak, sterilized by gamma irradiation) into a 250 mL PETG bottle. DS after filtration was aliquoted in 60 mL PETG bottles (25 mL filling volume) when stored frozen at −80° C. (stability study ongoing) or in 1.5 mL Eppendorf tubes when stored in liquid form (2-8° C., RT, 37° C.).

Figure 13:
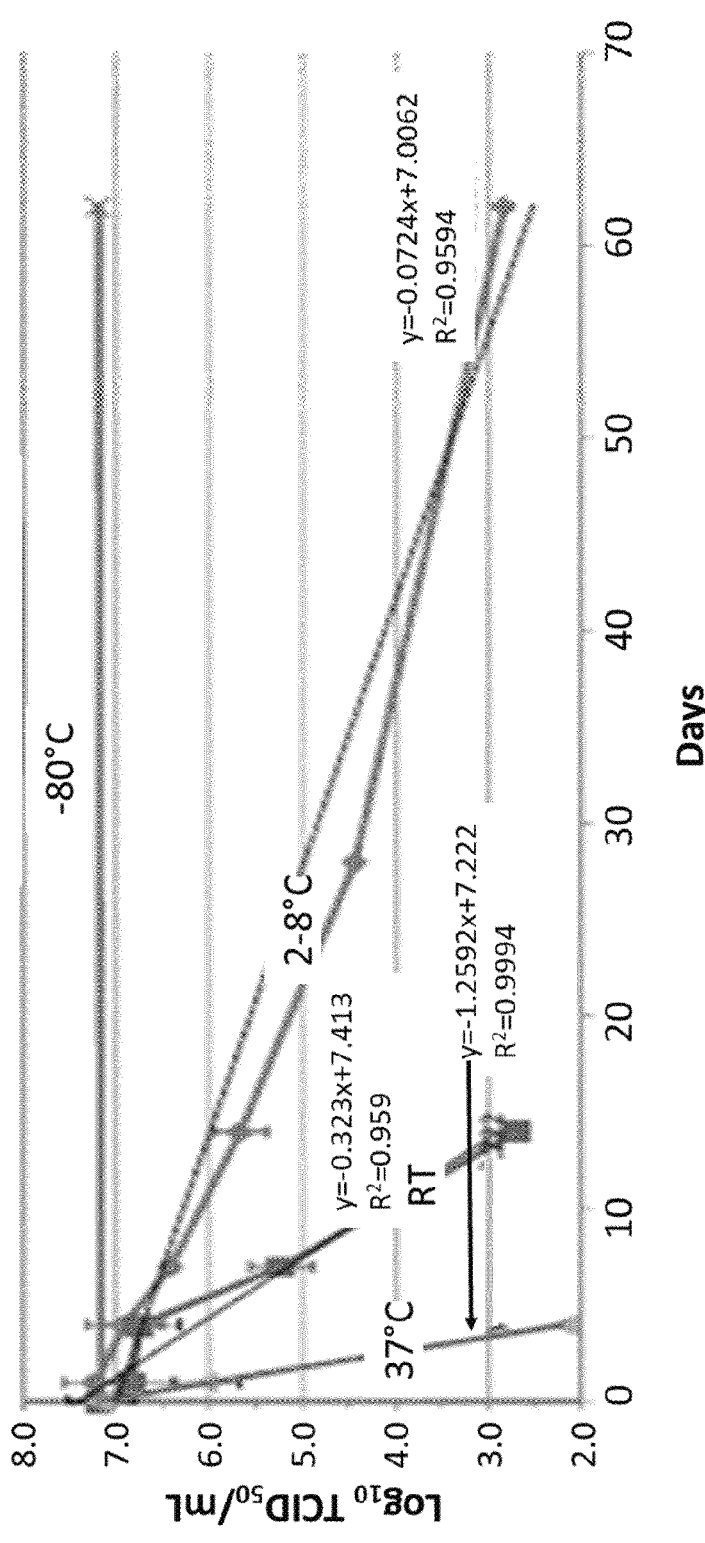
FIG. 13 Stability of CHIKV DS in the liquid (frozen) formulation at various temperatures.
Figure 14:
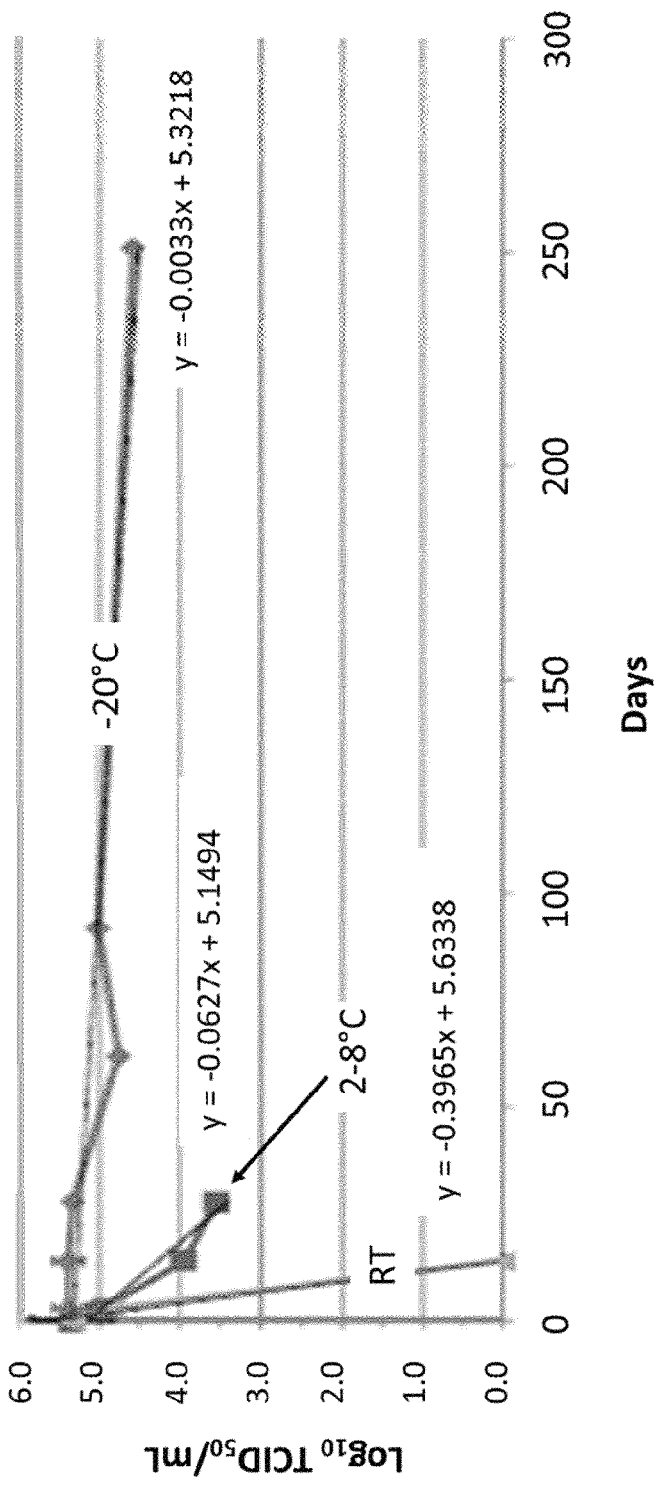
FIG. 14 Stability of CHIKV DP High dose in the liquid (frozen) formulation at various temperatures. Material stored in glass vials.

As expected, DS in the liquid (frozen) formulation stored at −80° C. remained stable at the day 60 timepoint (FIG. 13). When stored at 2-8° C. a decline of infectivity of approximately 0.5 log $TCID_{50}$/mL per week was observed. A complete loss of infectivity within a short time frame was observed when the material was stored at room temperature (after approx. two weeks) and at 37° C. (less than one week).

This DS was further processed to DP by a 1:50 dilution (196 mL formulation buffer+4 mL CHIKV DS). After mixing for 3 minutes and incubation for 15 minutes at room temperature, DP was filtered into a PETG bottle (Mini Kleenpak EKV membrane) and filled into glass vials (1 mL filling volume) closed with Flurotec stoppers. Stability studies were undertaken on vials stored at −20° C. (normal storage temperature) and under accelerated conditions (2-8° C. and RT). The results after approx. 8 months storage are shown in the FIG. 14.

As expected CHIKV-Δ5nsP3-inv presented in the liquid (frozen) formulation was unstable at 2-8° C. (~0.5 $\log_{10}$ loss per week) and especially if stored at room temperature (complete loss of infectivity within two weeks).

Example 3. Safety and Tolerability of the Attenuated CHIKV-Δ5nsP3 Vaccine

A randomized, observer-blinded, multicenter phase 1 trial to assess the safety, immunogenicity and antibody persistence of three escalating dosages of the live-attenuated Chikungunya virus vaccine candidate CHIKV-Δ5nsP3 (a.k.a. CHIKV-Δ5nsP3-inv; i.e., a mixture of CHIKV-Δ5nsP3 and variants) in healthy male and female volunteers was conducted. For the trial, the liquid frozen formulations as disclosed herein were used. Healthy volunteers aged 18 to 45 years were randomly assigned 1:1:2 to Low, Medium and High dose groups (L=3.2×$10^3$ $TCID_{50}$/0.1 ml dose, M=3.2× $10^4$ $TCID_{50}$/1 ml dose, H=3.2×$10^5$ $TCID_{50}$/1 ml dose) and each received a single-shot immunization on Day 0. Half of the individuals in Group H (Group H2) were challenged with the High dose at Month 6 and followed up 28 days post-challenge until Month 12. Individuals in Groups L, M and H1 were challenged with the High dose vaccine at Month 12 and followed up to 28 days post-challenge. (See FIGS. 15A and B.)

The study was conducted in compliance with the current International Conference on Harmonisation (ICH) of Technical Requirements for Registration of Pharmaceuticals for Human Use/Guideline for Good Clinical Practice and in accordance with the principles set forth in the Declaration of Helsinki. Throughout the study, an independent data safety monitoring board consisting of four external medical experts performed periodic reviews of accruing safety information. All enrolled subjects provided their written informed consent prior to any study-related procedure.

Healthy adults of both genders, aged 18 to 45 years, were eligible for inclusion in the trial. The baseline characteristics of the subjects are provided in Table 13. Female participants were eligible if they were of non-childbearing potential (i.e. surgically sterile or five years post-menopause). The main exclusion criteria included prior CHIKV infection, history of immune-mediated or chronic arthritis/arthralgia or immunization with an inactivated vaccine within 4 weeks or a live vaccine within 8 weeks prior to vaccination in the study. A full list of inclusion and exclusion criteria is provided in Table 2. One hundred and twenty participants were selected and randomly assigned to receive the single vaccination on Day 0 (FIG. 15B). Twenty-nine vaccinees terminated the study prior to Month 13, six were lost to follow-up and 20 withdrew their consent (none due to AEs). One subject was withdrawn from challenge due to an AE (syncope). Two other subjects were withdrawn due to unknown reasons. Baseline characteristics across all dosage groups were similar, with the exception that the majority of volunteers were male (Table 13). This gender disparity is reflected by the inclusion criterion allowing the enrollment of female subjects of non-childbearing potential only (Table 8).

TABLE 13

| Baseline Characteristics of Participants | | | | |
| --- | --- | --- | --- | --- |
| | Group L (N = 31) | Group M (N = 30) | Group H (N = 59) | All Participants N = 120 |
| Sex n (%) | | | | |
| Male | 28 (90.3) | 23 (76.7) | 55 (93.2) | 106 (88.3) |
| Female | 3 (9.7) | 7 (23.3) | 4 (6.8) | 14 (11.7) |
| Ethnic origin (%) | | | | |
| American Indian or Alaskan Native | 0 (0.0) | 0 (0.0) | 1 (1.7) | 1 (0.8) |
| Asian | 2 (6.5) | 1 (3.3) | 2 (3.4) | 5 (4.2) |
| African American | 6 (19.4) | 3 (10.0) | 8 (13.6) | 17 (14.2) |
| Native Hawaiian or Other Pacific Islander | 0 (0.0) | 0 (0.0) | 0 (0.0) | 0 (0.0) |
| Caucasian | 22 (71.0) | 26 (86.7) | 48 (81.4) | 96 (80.0) |
| Other | 1 (3.2) | 0 (0.0) | 0 (0.0) | 1 (0.8) |
| Age at screening [years] Mean | 32.8 | 32.3 | 32.5 | 32.5 |
| (Min/Max) | (21.0/43.0) | (21.0/45.0) | (19.0/45.0) | (19.0/45.0) |
| Height [cm] Mean | 179.3 | 174.8 | 179.1 | 178.1 |
| (Min/Max) | (157.5/195..6) | (152.4/190.5) | (160.0/200.7) | (152.4/200.7) |
| Weight [kg] Mean | 84.1 | 77.1 | 83.7 | 82.1 |
| (Min/Max) | (63.0/104.0) | (45.7/100.7) | (57.6/118 0) | (45.7/118.0) |
| BMI [kg/m$^2$] Mean | 26.2 | 25.1 | 26.0 | 25.8 |
| (Min/Max) | (20.8/29.4) | (19.0/29.9) | (20.1/29.8) | (19.0/29.7) |

TABLE 8

Inclusion and Exclusion Criteria for Participants

Inclusion Criteria
Subjects who meet ALL of the following criteria are eligible for this study:

1. Subject is 18 to 45 years of age on the Day of screening (Visit 0);
2. Subject has a BMI of ≥18.5 and <30 kg/m2 on the Day of screening (Visit 0);
3. Subject has an understanding of the study and its procedures, agrees to its provisions, and gives written informed consent prior to any study-related procedures;
4. Subject is generally healthy as determined by the Investigator's clinical judgement based on medical history, physical examination and screening laboratory tests;
5. If subject is of childbearing potential:
a) Subject has practiced an adequate method of contraception (see below) during the 30 days before screening (Visit 0);
b) Subject has a negative serum pregnancy test at screening (Visit 0);
c) Subject agrees to employ adequate birth control measures for the duration of the study. This includes one of the following measures:
Hormonal contraceptives (e.g. implants, birth control pills, patches);
Intrauterine device;
Barrier type of birth control measure (e.g. condoms, diaphragms, cervical caps);
Vasectomy in the male sex partner ≥3 months prior to first vaccination.
Exclusion Criteria
Subjects who meet ANY of the following criteria are NOT eligible for this study:

1. Subject has a history of known CHIKV infection;
2. Subject has plans to travel to areas with active CHIKV transmission during the course of the study or has travelled to an endemic CHIKV area within 4 weeks prior to study enrollment;
3. Subject has participated in a clinical study involving an investigational CHIKV vaccine;
4. Subject has received an inactivated vaccine within 4 weeks or live vaccine within 8 weeks prior to vaccination in this study;
5. Subject tests positive for human immunodeficiency virus (HIV), hepatitis B surface antigen (HBsAg) or hepatitis C virus (HCV);
6. Subject has at screening (Visit 0): (1) abnormal laboratory liver function values (≥grade 1), (2) any grade 1 abnormal lab values deemed clinically relevant by the Investigator, or (3) any ≥grade 2 abnormal lab values irrespective of clinical significance;
7. Subject has a clinically significant abnormal ECG at screening (Visit 0);
8. Subject currently has or has a history of significant cardiovascular, respiratory (including asthma), metabolic, neurological, hepatic, heumatic, autoimmune, hematological, gastrointestinal or renal disorder;
9. Subject has a history of immune-mediated or clinically significant arthritis/arthralgia;
10. Subject has a history of malignancy other than squamous cell or basal cell skin cancer, unless there has been surgical excision that is considered to have achieved a cure. A history of hematologic malignancy is a permanent exclusion. Subjects with a history of skin cancer must not be vaccinated at the previous tumor site;
11. Subject has a disease or is undergoing a form of treatment or was undergoing a form of treatment that can be expected to influence immune response. Such treatment includes, but is not limited to, systemic or high dose inhaled (>800 μg/day of beclomethasone dipropionate or equivalent) corticosteroids within 4 weeks prior to study entry, radiation therapy or immunosuppressive cytotoxic drugs/monoclonal antibodies in the previous 3 years;
12. Subject has a history of severe hypersensitivity reactions or anaphylaxis;
13. Subject has a history of any vaccine related contraindicating event (e.g., anaphylaxis, allergy to components of the candidate vaccine, other known contraindications);

TABLE 8-continued

Inclusion and Exclusion Criteria for Participants

14. Subject had acute febrile infections within two weeks prior to vaccination;
15. Subject has plans to become pregnant during the course of the study, or is pregnant (positive serum pregnancy test at screening) or lactating at the time of enrollment;
16. Subject has donated blood within 30 days or received blood-derived products (e.g. plasma) within 90 days prior to vaccination in this study or plans to donate blood or use blood products during the course of the study;
17. Subject has a rash, dermatological condition or tattoos that would, in the opinion of the Investigator, interfere with injection site reaction rating;
18. Subject has a known or suspected problem with alcohol or drug abuse as determined by the Investigator;
19. Subject has any condition that, in the opinion of the Investigator, may compromise the subjects well-being, might interfere with evaluation of study endpoints, or would limit the subject's ability to complete the study;
20. Subject is committed to an institution (by virtue of an order issued either by the judicial or the administrative authorities);
21. Subject has participated in another clinical study involving an investigational medicinal product (IMP) or device within 30 days prior to study enrollment or is scheduled to participate in another clinical study involving an IMP, or device during the course of this study;
22. Subject is a member of the team conducting the study or in a dependent relationship with one of the study team members. Dependent relationships include close relatives (i.e., children, partner/spouse, siblings, parents) as well as employees of the Investigator or site personnel conducting the study.

Figure 15A:
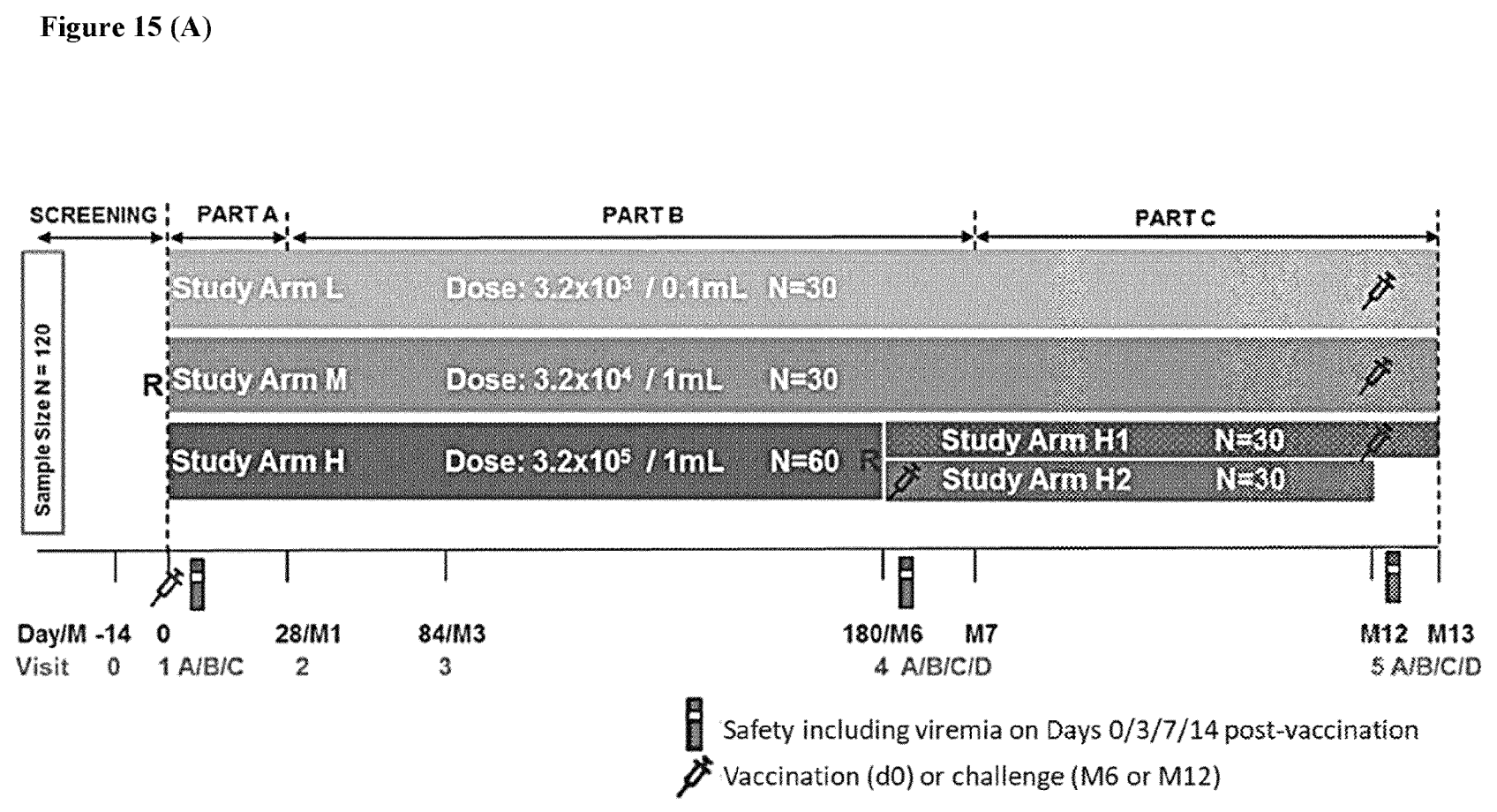

As shown in FIG. 15A, individuals were randomized 1:1:2 to Low dose (Group L) $3.2 \times 10^3$ $TCID_{50}$/0.1 ml dose, Medium dose (Group M) $3.2 \times 10^4$ $TCID_{50}$/ml dose or High dose (Group H) $3.2 \times 10^5$ $TCID_{50}$/ml dose to receive a single i.m. vaccination on Day 0. Dosing was adjusted by injection volume. Participants in dose Group H were re-randomized 1:1 at Month 6 to receive either a challenge with the High dose at Month 6 or Month 12. Participants in the Low and Medium dose groups were challenged with the High dose vaccine at Month 12 only. Participants and investigators were blinded to the assignment into dose groups. Randomization was performed via randomization envelopes in ascending order. The vaccine was prepared by unblinded study staff, unobserved by blinded staff members and the participant. Syringe content was masked prior to administration. For safety and immunogenicity evaluations, blood was drawn before the vaccinations (Day 0), at Days three, seven, 14, 28 and 180 post-vaccination, as well as at 84 days and 12 months after the single vaccination.

The primary objective was to assess safety and tolerability of the vaccine after a single vaccination. Participant diaries were used for the collection of daily oral body temperature, solicited injection and systemic reactions up to 14 days post-vaccination, which are assessed using FDA's toxicity grading scale. In addition, participants were monitored for symptoms suggesting an acute stage of CHIKV-associated events manifested by systemic symptoms presenting with sudden onset of fever, myalgia, headache, back pain and macular to maculopapular rash, sometimes with cutaneous pruritus (foot arch) and edema of the face and extremities, polyadenopathies, acute (poly)arthritis most frequently in the extremities (wrists, ankles and phalanges), tenosynovitis, neurological symptoms or cardiac symptoms.

For determination of viremia and shedding after vaccination and challenge, plasma and urine from subjects were analyzed for the presence of CHIKV genomic RNA by Reverse Transcriptase quantitative PCR (RT-qPCR) (Panning, M. et al., 2008, Chikungunya Fever in Travelers Returning to Europe from the Indian Ocean Region, 2006. Emerging Infectious Diseases 14(3):416-422; Pastorino B. et al., 2015, Development of a TaqMan RT-PCR assay without RNA extraction step for detection and quantification of African Chikungunya viruses, Journal of Virological Methods, 65-71). In brief, total RNA was extracted from individual specimens and subjected to RT-qPCR using a hydrolysis probe and primers specific to the CHIKV nsP1 gene. The read-out was quantitative and reported as the number of CHIKV genome copy equivalents (GCE) per 1 mL of initial subject specimen. The assay was qualified for precision and specificity. The limits of detection and quantification were defined as 1087 GCE/mL (10 GCE/reaction) and 3261 GCE/mL (30 GCE/reaction), respectively. Time points with no available results in the treatment group were plotted at 500.

Statistical analysis. The sample size of 120 participants allowed for the detection of AEs, which commonly have a close relationship to vaccination, and with a true underlying prevalence of 2.5% with a probability of 95%. The study was not powered to detect uncommon or rare AEs, thus a placebo group was not included. All participants who received a single vaccination at Day 0 were included in the safety dataset. The number and percentage of individuals with solicited injection site and systemic reactions up to 14 days after each vaccination, and with unsolicited AEs and SAEs were presented for each dose group overall and by body system/preferred term and were compared using Fisher's exact test for differences between groups; a significant overall test was amended by pair-wise tests between individual groups.

The primary outcome of the study was to assess the safety and tolerability of the vaccine. The live-attenuated CHIKV-Δ5nsP3 vaccine was generally safe and well-tolerated up to Month 12 after the single vaccination in the Low and Medium dosage groups and generally safe in all dosage groups. A summary of adverse events after the single vaccination is provided in Table 9. The Low and Medium dosages showed a superior reactogenicity profile compared to the High dosage group (p-value 0.0089; pairwise test M vs. H 0.0042). The vast majority of AEs across the dose groups were assessed as mild or moderate and the majority of AEs were reported after the single vaccination. No adverse event of special interest and no vaccine related serious adverse events were reported. Two unrelated serious adverse events occurred; one event of polytrauma following a car accident and one event of atrial ectopy 62 days following the 6 month re-vaccination (Table 9). Following any challenge, rates of AEs were substantially diminished, only six participants reported related AEs occurring within 28 days after any challenge, indicating that participants were protected from challenge-induced AEs (summary provided in Table 10).

TABLE 9

Summary of Adverse Events after Single Vaccination up to M12

| | Statistics | Group L (N = 31) | Group M (N = 30) | Group H (N = 59) | p-value (Overall) |
|---|---|---|---|---|---|
| Any AE | n (%) Obs | 21 (67.7) 57 | 19 (63.3) 69 | 48 (81.4) 209 | 0.1349 |
| | [95% CI] | [50.1, 81.4] | [45.5, 78.1] | [69.6, 89.3] | |
| Any related AE | n (%) Obs | 18 (58.1) 43 | 14 (46.7) 49 | 46 (78.0) 168 | 0.0089 |
| | [95% CI] | [40.8, 73.6] | [30.2, 63.9] | [65.9, 86.6] | |
| Pairwise test | vs. M | 0.4462 | . . . | . . . | |
| | vs. H | 0.0550 | 0.0042 | . . . | |
| Any severe AE | n (%) Obs | 4 (12.9) 4 | 3 (10.0) 3 | 7 (11.9) 8 | 1.0000 |
| | [95% CI] | [5.1, 28.9] | [3.5, 25.6] | [5.9, 22.5] | |
| Any related severe AE | n (%) Obs | 4 (12.9) 4 | 2 (6.7) 2 | 7 (11.9) 8 | 0.7998 |
| | [95% CI] | [5.1, 28.9] | [1.8, 21.3] | [5.9, 22.5] | |
| Any SAE | n (%) Obs | 0 (0.0) 0 | 1 (3.3) 1 | 0 (0.0) 0 | 0.2500 |
| | [95% CI] | [0.0, 11.0] | [0.6, 16.7] | [0.0, 6.1] | |
| Any related SAE | n (%) Obs | 0 (0.0) 0 | 0 (0.0) 0 | 0 (0.0) 0 | NC |
| | [95% CI] | [0.0, 11.0] | [0.0, 11.4] | [0.0, 6.1] | |
| Any medically attended AE | n (%) Obs | 2 (6.5) 4 | 5 (16.7) 5 | 10 (16.9) 15 | 0.3856 |
| | [95% CI] | [1.8, 20.7] | [7.3, 33.6] | [9.5, 28.5] | |
| Any related medically attended AE | n (%) Obs | 1 (3.2) 2 | 0 (0.0) 0 | 0 (0.0) 0 | 0.5083 |
| | [95% CI] | [0.6, 16.2] | [0.0, 11.4] | [0.0, 6.1] | |
| Any solicited AE | n (%) Obs | 11 (35.5) 23 | 12 (40.0) 41 | 40 (67.8) 107 | 0.0038 |
| | [95% CI] | [21.1, 53.1] | [24.6, 57.7] | [55.1, 78.3] | |
| Pairwise test | vs. M | 0.7946 | . . . | . . . | |
| | vs. H | 0.0040 | 0.0220 | . . . | |
| Any related solicited AE | n (%) Obs | 10 (32.3) 20 | 10 (33.3) 34 | 40 (67.8) 106 | 0.0007 |
| | [95% CI] | [18.6, 49.9] | [19.2, 51.2] | [55.1, 78.3] | |
| Pairwise test | vs. M | 1.0000 | . . . | . . . | |
| | vs. H | 0.0017 | 0.0031 | . . . | |
| Any severe solicited AE | n (%) Obs | 1 (3.2) 1 | 1 (3.3) 1 | 5 (8.5) 6 | 0.6796 |
| | [95% CI] | [0.6, 16.2] | [0.6, 16.7] | [3.7, 18.4] | |
| Any solicited local AE | n (%) Obs | 1 (3.2) 1 | 2 (6.7) 3 | 4 (6.8) 4 | 0.7827 |
| | [95% CI] | [0.6, 16.2] | [1.8, 21.3] | [2.7, 16.2] | |
| Any solicited systemic AE | n (%) Obs | 11 (35.5) 22 | 12 (40.0) 38 | 40 (67.8) 103 | 0.0038 |
| | [95% CI] | [21.1, 53.1] | [24.6, 57.7] | [55.1, 78.3] | |
| Pairwise test | vs. M | 0.7946 | . . . | . . . | |
| | vs. H | 0.0040 | 0.0220 | . . . | |
| Any severe solicited systemic AE | n (%) Obs | 1 (3.2) 1 | 1 (3.3) 1 | 5 (8.5) 6 | 0.6796 |
| | [95% CI] | [0.6, 16.2] | [0.6, 16.7] | [3.7, 18.4] | |
| Any unsolicited AE | n (%) Obs | 17 (54.8) 34 | 15 (50.0) 28 | 36 (61.0) 102 | 0.5849 |
| | [95% CI] | [37.8, 70.8] | [33.2, 66.8] | [48.3, 72.4] | |
| Any related unsolicited AE | n (%) Obs | 13 (41.9) 23 | 8 (26.7) 15 | 29 (49.2) 61 | 0.1310 |
| | [95% CI] | [26.4, 59.2] | [14.2, 44.4] | [36.8, 61.6] | |
| Any severe unsolicited AE | n (%) Obs | 3 (9.7) 3 | 2 (6.7) 2 | 2 (3.4) 2 | 0.4588 |
| | [95% CI] | [3.3, 24.9] | [1.8, 21.3] | [0.9, 11.5] | |
| Any related severe unsolicited AE | n (%) Obs | 3 (9.7) 3 | 1 (3.3) 1 | 2 (3.4) 2 | 0.5452 |
| | [95% CI] | [3.3, 24.9] | [0.6, 16.7] | [0.9, 11.5] | |
| Any AESI | n (%) Obs | 0 (0.0) 0 | 0 (0.0) 0 | 0 (0.0) 0 | NC |
| | [95% CI] | [0.0, 11.0] | [0.0, 11.4] | [0.0, 6.1] | | n . . . number of participants with AE, percentages are based on N, Obs . . . number of events
p-value (Overall): Fisher-Freeman-Halton test between Groups L, M, H
NC . . . not calculable

TABLE 10

Summary of Adverse Events after Challenge at M6 (H2) or M12 (L, M, H1)

| | Statistic | Group L (N = 24) | Group M (N = 23) | Group H1 (N = 21) | Group H2 (N = 26) |
|---|---|---|---|---|---|
| Any AE | n (%) Obs | 3 (12.5) 4 | 0 (0.0) 0 | 4 (19.0) 6 | 5 (19.2) 13 |
| | [95% CI] | [4.3, 31.0] | [0.0, 14.3] | [7.7, 40.0] | [8.5, 37.9] |
| Any related AE | n (%) Obs | 1 (4.2) 1 | 0 (0.0) 0 | 3 (14.3) 4 | 2 (7.7) 3 |
| | [95% CI] | [0.7, 20.2] | [0.0, 14.3] | [5.0, 34.6] | [2.1, 24.1] |
| Any severe AE | n (%) Obs | 0 (0.0) 0 | 0 (0.0) 0 | 0 (0.0) 0 | 2 (7.7) 2 |
| | [95% CI] | [0.0, 13.8] | [0.0, 14.3] | [0.0, 15.5] | [2.1, 24. 1] |
| Any related severe AE | n (%) Obs | 0 (0.0) 0 | 0 (0.0) 0 | 0 (0.0) 0 | 2 (7.7) 2 |
| | [95% CI] | [0.0, 13.8] | [0.0, 14.3] | [0.0, 15.5] | [2.1, 24. 1] |
| Any SAE | n (%) Obs | 0 (0.0) 0 | 0 (0.0) 0 | 0 (0.0) 0 | 0 (0.0) 0 |
| | [95% CI] | [0.0, 13.8] | [0.0, 14.3] | [0.0, 15.5] | [0.0, 12.9] |
| Any related SAE | n (%) Obs | 0 (0.0) 0 | 0 (0.0) 0 | 0 (0.0) 0 | 0 (0.0) 0 |
| | [95% CI] | [0.0, 13.8] | [0.0, 14.3] | [0.0, 15.5] | [0.0, 12.9] |
| Any medically attended AE | n (%) Obs | 0 (0.0) 0 | 0 (0.0) 0 | 1 (4.8) 1 | 2 (7.7) 3 |
| | [95% CI] | [0.0, 13.8] | [0.0, 14.3] | [0.8, 22.7] | [2.1, 24.1] |

TABLE 10-continued

| | | Group L (N = 24) | Group M (N = 23) | Group H1 (N = 21) | Group H2 (N = 26) |
|---|---|---|---|---|---|
| | Statistic | | | | |
| Any related medically attended AE | n (%) Obs | 0 (0.0) 0 | 0 (0.0) 0 | 0 (0.0) 0 | 1 (3.8) 1 |
| | [95% CI] | [0.0, 13.8] | [0.0, 14.3] | [0.0, 15.5] | [0.7, 18.9] |
| Any solicited AE | n (%) Obs | 1 (4.2) 1 | 0 (0.0) 0 | 3 (14.3) 4 | 2 (7.7) 3 |
| | [95% CI] | [0.7, 20.2] | [0.0, 14.3] | [5.0, 34.6] | [2.1, 24.1] |
| Any related solicited AE | n (%) Obs | 1 (4.2) 1 | 0 (0.0) 0 | 3 (14.3) 4 | 2 (7.7) 3 |
| | [95% CI] | [0.7, 20.2] | [0.0, 14.3] | [5.0, 34.6] | [2.1, 24.1] |
| Any severe solicited AE | n (%) Obs | 0 (0.0) 0 | 0 (0.0) 0 | 0 (0.0) 0 | 2 (7.7) 2 |
| | [95% CI] | [0.0, 13.8] | [0.0, 14.3] | [0.0, 15.5] | [2.1, 24.1] |
| Any solicited local AE | n (%) Obs | 1 (4.2) 1 | 0 (0.0) 0 | 2 (9.5) 2 | 0 (0.0) 0 |
| | [95% CI] | [0.7, 20.2] | [0.0, 14.3] | [2.7, 28.9] | [0.0, 12.9] |
| Any solicited systemic AE | n (%) Obs | 0 (0.0) 0 | 0 (0.0) 0 | 1 (4.8) 2 | 2 (7.7) 3 |
| | [95% CI] | [0.0, 13.8] | [0.0, 14.3] | [0.8, 22.7] | [2.1, 24.1] |
| Any severe solicited systemic AE | n (%) Obs | 0 (0.0) 0 | 0 (0.0) 0 | 0 (0.0) 0 | 2 (7.7) 2 |
| | [95% CI] | [0.0, 13.8] | [0.0, 14.3] | [0.0, 15.5] | [2.1, 24.1] |
| Any unsolicited AE | n (%) Obs | 2 (8.3) 3 | 0 (0.0) 0 | 2 (9.5) 2 | 4 (15.4) 10 |
| | [95% CI] | [2.3, 25.8] | [0.0, 14.3] | [2.7, 28.9] | [6.2, 33.5] |
| Any related unsolicited AE | n (%) Obs | 0 (0.0) 0 | 0 (0.0) 0 | 0 (0.0) 0 | 0 (0.0) 0 |
| | [95% CI] | [0.0, 13.8] | [0.0, 14.3] | [0.0, 15.5] | [0.0, 12.9] |
| Any severe unsolicited AE | n (%) Obs | 0 (0.0) 0 | 0 (0.0) 0 | 0 (0.0) 0 | 0 (0.0) 0 |
| | [95% CI] | [0.0, 13.8] | [0.0, 14.3] | [0.0, 15.5] | [0.0, 12.9] |
| Any AESI | n (%) Obs | 0 (0.0) 0 | 0 (0.0) 0 | 0 (0.0) 0 | 0 (0.0) 0 |
| | [95% CI] | [0.0, 13.8] | [0.0, 14.3] | [0.0, 15.5] | [0.0, 12.9] |

Figure 16:
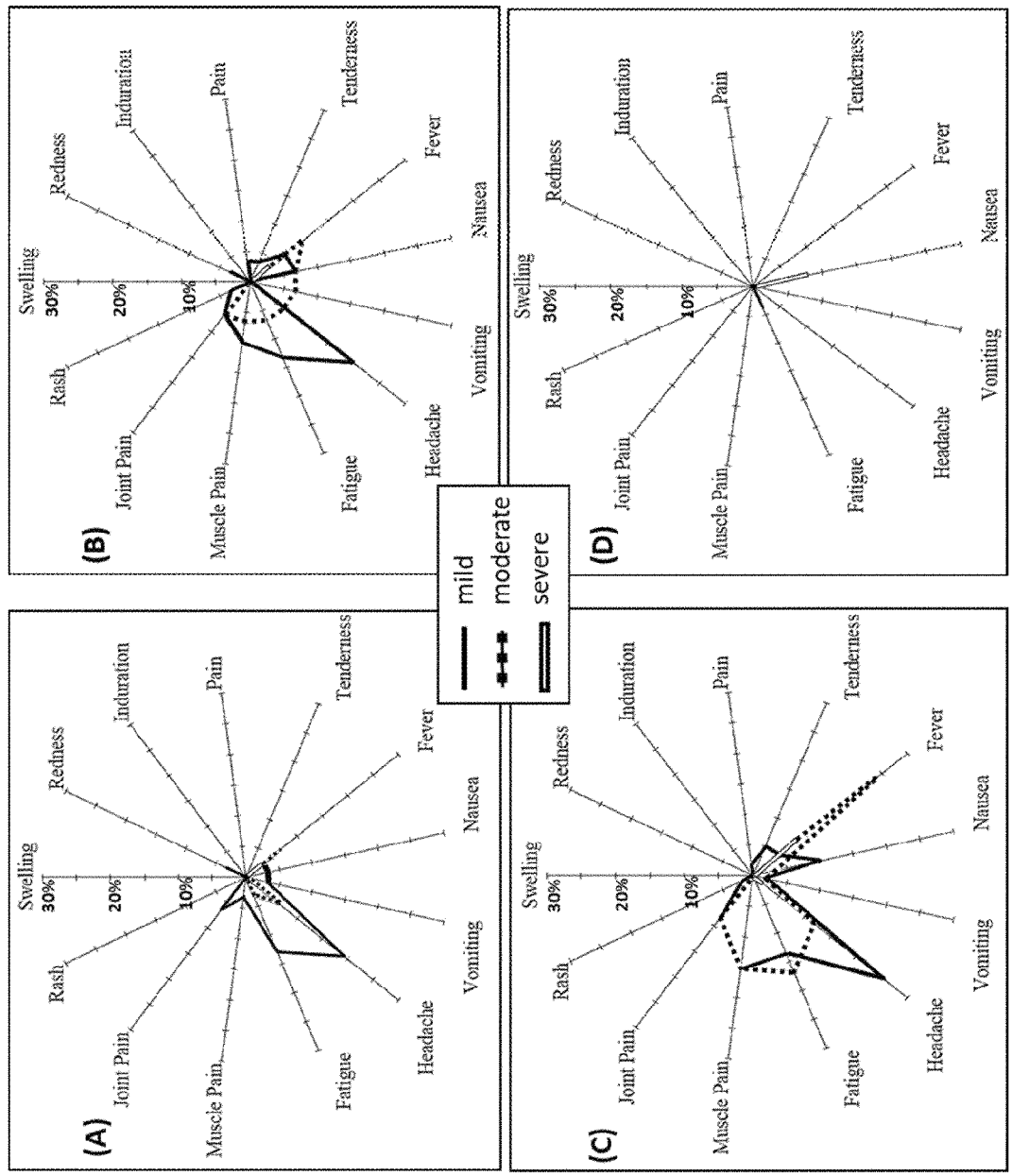
FIG. 16 Radar plot of solicited local and systemic symptoms after single vaccination and revaccination (challenge) including severity grading (Safety Population). Participants with solicited AEs within 14 days after single vaccination with (A) Low dose (Group L; $3.2 \times 10^3$ $TCID_{50}$/0.1 ml) (B) Medium dose (Group M; $3.2 \times 10^4$ $TCID_{50}$/1 ml) and (C) High dose (Groups H1 and H2; $3.2 \times 10^5$ $TCID_{50}$/1 ml); or after high dose revaccination at 6 months (D) group H2 at M6; or 12 months (E) group L at M12; (F) group M at M12; (G) group H1 at M12, by maximum severity. Solicited AEs were graded as mild (Grade 1), moderate (Grade 2) or severe (Grade 3).
Figure 16:
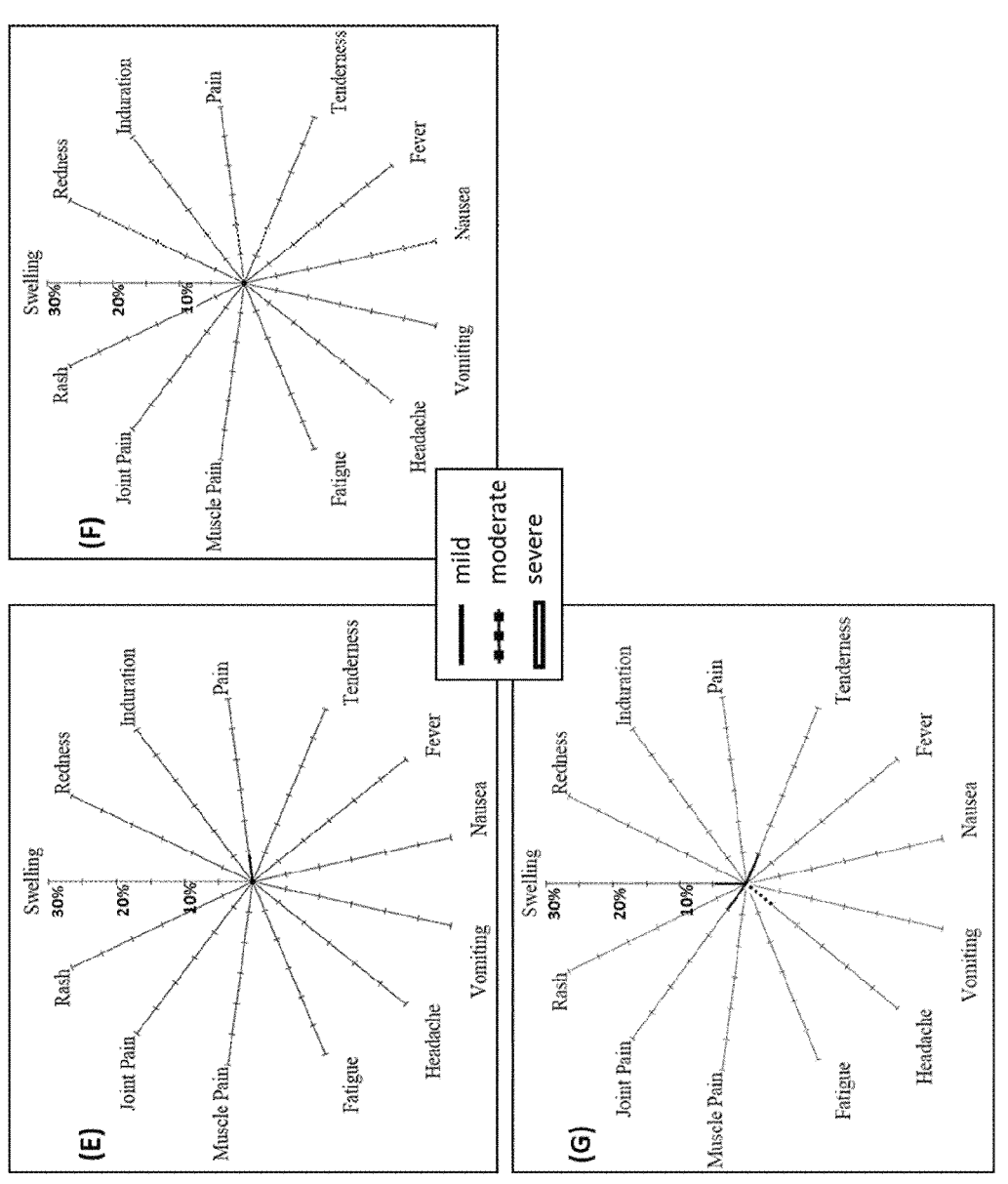

Summary of Adverse Events after Challenge at M6 (H2) or M12 (L, M, H1)

n . . . number of participants with AE, percentages are based on N, Obs . . . number of events The local tolerability profile within 14 days after the single vaccination was considered excellent at all dose levels, with less than 7% of vaccinees (4/59 in Group H) reporting any local AE (p-value overall 0.7827). Tenderness was the most common injection site reaction after the single vaccination, affecting more than 5% of subjects (3/59 in Group H) (FIG. 16A-C). No injection site reactions were observed after challenge at Month 6 (FIG. 16D). One mild case each of pain, tenderness and swelling was reported after challenge at Month 12 (FIG. 16 E-G). Notable systemic adverse events included short-term fever, headache, fatigue and muscle pain. Rates of related systemic AEs were significantly lower in the Low and Medium dosage groups compared to the High dosage group (p-value overall 0.0007; pairwise test L vs. H 0.0017; M vs. H 0.0031). Nine individuals experienced ten related severe solicited systemic AEs (Tables 3 and 4), predominantly fever, occurring within two to four days after the single vaccination: one fever case each in the Low and Medium dosage groups and five cases in the High dosage group; and one severe case of headache (H) (Table 11). Following challenge at Month 6 or 12, none of the vaccinees experienced fever; two individuals in dose group H2 reported severe nausea after 6 months challenge, one case each of moderate headache and mild joint pain were reported in dose group H1 after 12 months challenge (Table 12).

TABLE 11

Related Solicited Systemic AEs by Symptom within 14 Days after Single Vaccination

| | Statistic | Group L (N = 31) | Group M (N = 30) | Group H (N = 59) | p-value (Overall) |
|---|---|---|---|---|---|
| Fever | | | | | |
| severe (Grade 3) | n (%) Obs [95% CI] | 1 (3.2) 1 [0.6, 16.2] | 1 (3.3) 1 [0.6, 16.7] | 5 (8.5) 5 [3.7, 18.4] | 0.6796 |
| moderate (Grade 2) | n (%) Obs [95% CI] | 2 (6.5) 2 [1.8, 20.7] | 3 (10.0) 4 [3.5, 25.6] | 14 (23.7) 14 [14.7, 36.0] | 0.0894 |

TABLE 11-continued

Related Solicited Systemic AEs by Symptom within 14 Days after Single Vaccination

| | Statistic | Group L (N = 31) | Group M (N = 30) | Group H (N = 59) | p-value (Overall) |
|---|---|---|---|---|---|
| mild (Grade 1) Nausea | n (%) Obs [95% CI] | 0 (0.0) 0 [0.6, 16.2] | 2 (6.7) 3 [1.8, 21.3] | 3 (5.1) 3 [1.7, 13.9] | 0.5157 |
| severe (Grade 3) | n (%) Obs [95% CI] | 0 (0.0) 0 [0.0, 11.0] | 0 (0.0) 0 [0.0, 11.4] | 0 (0.0) 0 [0.0, 6.1] | NC |
| moderate (Grade 2) | n (%) Obs [95% CI] | 0 (0.0) 0 [0.0, 11.0] | 1 (3.3) 1 [0.6, 16.7] | 2 (3.4) 2 [0.9, 11.5] | 0.6158 |
| mild (Grade 1) Vomiting | n (%) Obs [95% CI] | 1 (3.2) 1 [0.6, 16.2] | 2 (6.7) 2 [1.8, 21.3] | 6 (10.2) 6 [4.7, 20.5] | 0.5509 |
| severe (Grade 3) | n (%) Obs [95% CI] | 0 (0.0) 0 [0.0, 11.0] | 0 (0.0) 0 [0.0, 11.4] | 0 (0.0) 0 [0.0, 6.1] | NC |
| moderate (Grade 2) | n (%) Obs [95% CI] | 0 (0.0) 0 [0.0, 11.0] | 1 (3.3) 1 [0.6, 16.7] | 1 (1.7) 1 [0.3, 9.0] | 0.7438 |
| mild (Grade 1) Headache | n (%) Obs [95% CI] | 1 (3.2) 1 [0.6, 16.2] | 0 (0.0) 0 [0.0, 11.4] | 1 (1.7) 1 [0.3, 9.0] | 1.0000 |
| severe (Grade 3) | n (%) Obs [95% CI] | 0 (0.0) 0 [0.0, 11.0] | 0 (0.0) 0 [0.0, 11.4] | 1 (1.7) 1 [0.3, 9.0] | 1.0000 |
| moderate (Grade 2) | n (%) Obs [95% CI] | 2 (6.5) 2 [1.8, 20.7] | 1 (3.3) 1 [0.6, 16.7] | 7 (11.9) 7 [5.9, 22.5] | 0.4793 |
| mild (Grade 1) Fatigue | n (%) Obs [95% CI] | 5 (16.1) 5 [7.1, 32.6] | 6 (20.0) 6 [9.5, 37.3] | 14 (23.7) 15 [14.7, 36.0] | 0.7364 |
| severe (Grade 3) | n (%) Obs [95% CI] | 0 (0.0) 0 [0.0, 11.0] | 0 (0.0) 0 [0.0, 11.4] | 0 (0.0) 0 [0.0, 6.1] | NC |
| moderate (Grade 2) | n (%) Obs [95% CI] | 1 (3.2) 1 [0.6, 16.2] | 1 (3.3) 1 [0.6, 16.7] | 10 (16.9) 10 [9.5, 28.5] | 0.0725 |
| mild (Grade 1) Muscle Pain | n (%) Obs [95% CI] | 4 (12.9) 4 [5.1, 28.9] | 4 (13.3) 4 [5.3, 29.7] | 8 (13.6) 8 [7.0, 24.5] | 1.0000 |
| severe (Grade 3) | n (%) Obs [95% CI] | 0 (0.0) 0 [0.0, 11.0] | 0 (0.0) 0 [0.0, 11.4] | 0 (0.0) 0 [0.0, 6.1] | NC |
| moderate (Grade 2) | n (%) Obs [95% CI] | 0 (0.0) 0 [0.0, 11.0] | 1 (3.3) 1 [0.6, 16.7] | 9 (15.3) 9 [8.2, 26.5] | 0.0222 |
| Pairwise | vs. M | 0.4918 | . . . | . . . | |

TABLE 11-continued

| | | | | | |
|---|---|---|---|---|---|
| Related Solicited Systemic AEs by Symptom within 14 Days after Single Vaccination | | | | | |
| | Statistic | Group L (N = 31) | Group M (N = 30) | Group H (N = 59) | p-value (Overall) |
| tests | vs. H | 0.0249 | 0.1548 | . . . | |
| mild | n (%) Obs | 1 (3.2) 1 | 3 (10.0) 3 | 9 (15.3) 9 | 0.2227 |
| (Grade 1) | [95% CI] | [0.6, 16.2] | [3.5, 25.6] | [8.2, 26.5] | |
| Joint Pain | | | | | |
| severe | n (%) Obs | 0 (0.0) 0 | 0 (0.0) 0 | 0 (0.0) 0 | NC |
| (Grade 3) | [95% CI] | [0.0, 11.0] | [0.0, 11.4] | [0.0, 6.1] | |
| moderate | n (%) Obs | 0 (0.0) 0 | 1 (3.3) 1 | 5 (8.5) 5 | 0.2685 |
| (Grade 2) | [95% CI] | [0.0, 11.0] | [0.6, 16.7] | [3.7, 18.4] | |

TABLE 11-continued

| | | | | | |
|---|---|---|---|---|---|
| Related Solicited Systemic AEs by Symptom within 14 Days after Single Vaccination | | | | | |
| | Statistic | Group L (N = 31) | Group M (N = 30) | Group H (N = 59) | p-value (Overall) |
| mild (Grade 1) Rash | n (%) Obs [95% CI] | 1 (3.2) 1 [0.6, 16.2] | 2 (6.7) 2 [1.8, 21.3] | 5 (8.5) 5 [3.7, 18.4] | 0.8073 |
| severe (Grade 3) | n (%) Obs [95% CI] | 0 (0.0) 0 [0.0, 11.0] | 0 (0.0) 0 [0.0, 11.4] | 0 (0.0) 0 [0.0, 6.1] | NC |
| moderate (Grade 2) | n (%) Obs [95% CI] | 0 (0.0) 0 [0.0, 11.0] | 0 (0.0) 0 [0.0, 11.4] | 0 (0.0) 0 [0.0, 6.1] | NC |
| mild (Grade 1) | n (%) Obs [95% CI] | 0 (0.0) 0 [0.0, 11.0] | 0 (0.0) 0 [0.0, 11.4] | 1 (1.7) 1 [0.3, 9.0] | 1.0000 | n . . . number of participants with AE, percentages are based on N, Obs . . . number of events
p-value (Overall): Fisher's exact test for overall differences between groups
NC . . . not calculable

TABLE 12

| | | | | | | |
|---|---|---|---|---|---|---|
| Related Solicited Systemic AEs by Symptom within 14 Days after Challenge at M6 (H2) or M12 (L, M, H1) | | | | | | |
| | Statistic | Group L (N = 24) | Group M (N = 23) | Group H1 (N = 21) | Group H2 (N = 26) | p-value (L vs. M vs. H1) |
| Fever | | | | | | |
| severe (Grade 3) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| moderate (Grade 2) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| mild (Grade 1) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| Nausea | | | | | | |
| severe (Grade 3) | n (%) Obs [95% CI] | 0 (0.0) 0 [0.0, 13.8] | 0 (0.0) 0 [0.0, 14.3] | 0 (0.0) 0 [0.0, 15.5] | 2 (7.7) 2 [2.1, 24.1] | NC |
| moderate (Grade 2) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| mild (Grade 1) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| Vomiting | | | | | | |
| severe (Grade 3) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| moderate (Grade 2) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| mild (Grade 1) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| Headache | | | | | | |
| severe (Grade 3) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| moderate (Grade 2) | n (%) Obs [95% CI] | 0 (0.0) 0 [0.0, 13.8] | 0 (0.0) 0 [0.0, 14.3] | 1 (4.8) 1 [0.8, 22.7] | 0 (0.0) 0 [0.0, 12.9] | 0.3088 |
| mild (Grade 1) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| Fatigue | | | | | | |
| severe (Grade 3) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| moderate (Grade 2) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| mild (Grade 1) | n (%) Obs [95% CI] | 0 (0.0) 0 [0.0, 13.8] | 0 (0.0) 0 [0.0, 14.3] | 0 (0.0) 0 [0.0, 15.5] | 1 (3.8) 1 [0.7, 18.9] | NC |
| Muscle Pain | | | | | | |
| severe (Grade 3) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |
| moderate (Grade 2) | n (%) Obs [95% CI] | 0 (0.0) 0 [0.0, 13.8] | 0 (0.0) 0 [0.0, 14.3] | 0 (0.0) 0 [0.0, 15.5] | 0 (0.0) 0 [0.0, 12.9] | NC |

TABLE 12-continued

Related Solicited Systemic AEs by Symptom within 14
Days after Challenge at M6 (H2) or M12 (L, M, H1)

| | Statistic | Group L (N = 24) | Group M (N = 23) | Group H1 (N = 21) | Group H2 (N = 26) | p-value (L vs. M vs. H1) |
|---|---|---|---|---|---|---|
| mild (Grade 1) | n (%) Obs | 0 (0.0) 0 | 0 (0.0) 0 | 0 (0.0) 0 | 0 (0.0) 0 | NC |
| | [95% CI] | [0.0, 13.8] | [0.0, 14.3] | [0.0, 15.5] | [0.0, 12.9] | |
| Joint Pain | | | | | | |
| severe (Grade 3) | n (%) Obs | 0 (0.0) 0 | 0 (0.0) 0 | 0 (0.0) 0 | 0 (0.0) 0 | NC |
| | [95% CI] | [0.0, 13.8] | [0.0, 14.3] | [0.0, 15.5] | [0.0, 12.9] | |
| moderate (Grade 2) | n (%) Obs | 0 (0.0) 0 | 0 (0.0) 0 | 0 (0.0) 0 | 0 (0.0) 0 | NC |
| | [95% CI] | [0.0, 13.8] | [0.0, 14.3] | [0.0, 15.5] | [0.0, 12.9] | |
| mild (Grade 1) | n (%) Obs | 0 (0.0) 0 | 0 (0.0) 0 | 1 (4.8) 1 | 0 (0.0) 0 | 0.3088 |
| | [95% CI] | [0.0, 13.8] | [0.0, 14.3] | [0.8, 22.7] | [0.0, 12.9] | |
| Rash | | | | | | |
| severe (Grade 3) | n (%) Obs | 0 (0.0) 0 | 0 (0.0) 0 | 0 (0.0) 0 | 0 (0.0) 0 | NC |
| | [95% CI] | [0.0, 13.8] | [0.0, 14.3] | [0.0, 15.5] | [0.0, 12.9] | |
| moderate (Grade 2) | n (%) Obs | 0 (0.0) 0 | 0 (0.0) 0 | 0 (0.0) 0 | 0 (0.0) 0 | NC |
| | [95% CI] | [0.0, 13.8] | [0.0, 14.3] | [0.0, 15.5] | [0.0, 12.9] | |
| mild (Grade 1) | n (%) Obs | 0 (0.0) 0 | 0 (0.0) 0 | 0 (0.0) 0 | 0 (0.0) 0 | NC |
| | [95% CI] | [0.0, 13.8] | [0.0, 14.3] | [0.0, 15.5] | [0.0, 12.9] | | n . . . number of participants with AE, percentages are based on N, Obs . . . number of events Changes in blood cell counts were observed in one third of participants after the single vaccination; most commonly Leukopenia, Neutropenia and Lymphopenia (Table 13). Severe cases were observed across all groups: two cases of neutropenia in the Low and one case in the Medium dose group; two cases of lymphocytopenia in the High dose group. After challenge, no severe cases were reported and a significant reduction in the occurrence of these values in comparison to post single vaccination (paired signed rank test difference at Day 7 after single vs after challenge, p-value <0.0001, Table 13) was observed.

Figures 17, 18:
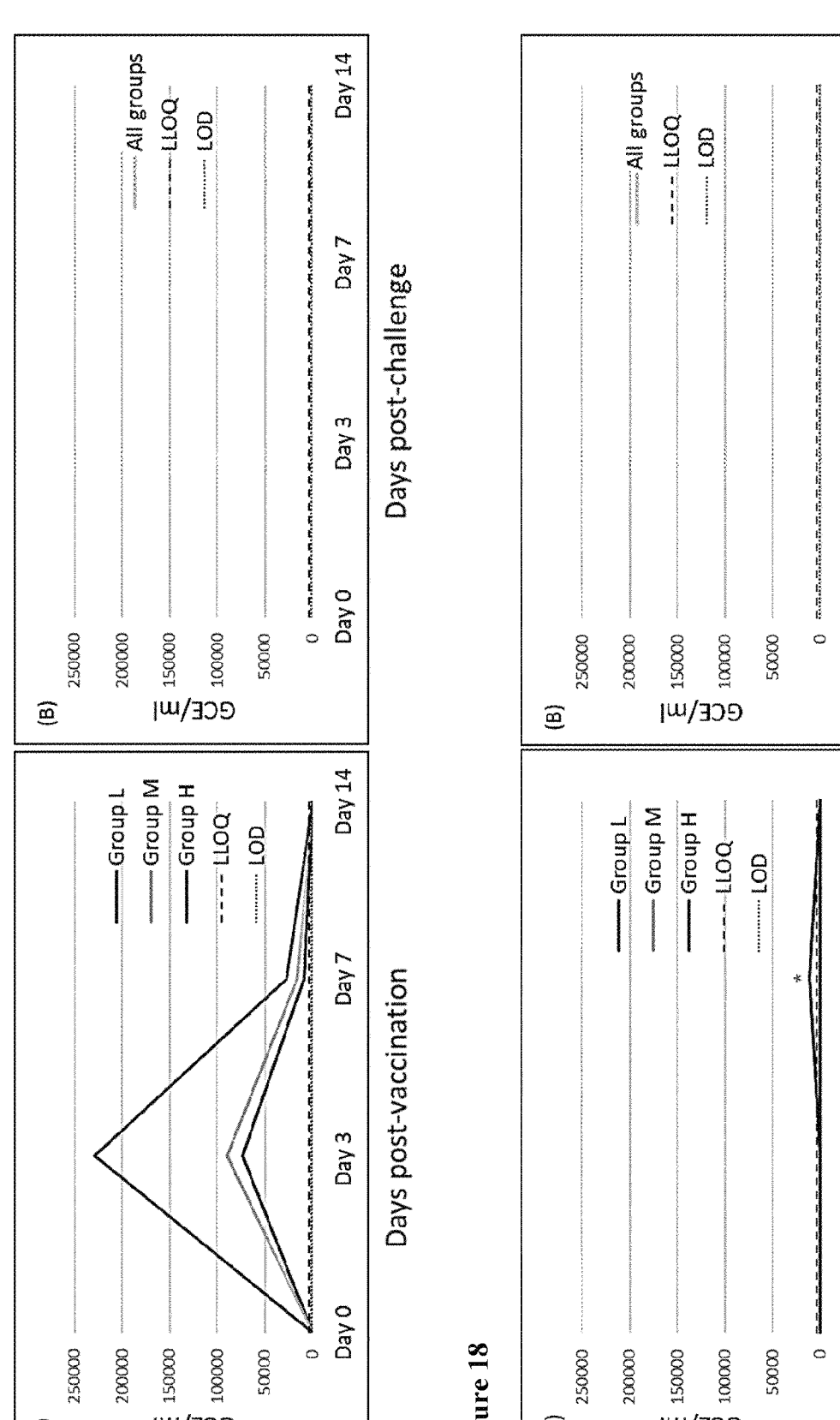
FIG. 17 Viremia in plasma at Days 0, 3, 7 and 14 after immunization (A) and any challenge (B). Limit of Detection (LOD)=1087 GCE/mL, Lower Limit of Quantification (LLOQ)=3261 GCE/mL. Time points with no available results in the treatment group were graphed as 500. GCE/mL—Genome copy equivalents per mL determined by quantitative real-time PCR.
FIG. 18 Shedding of viral particles in urine at Days 0, 3, 7 and 14 after vaccination (A) and any challenge (B). Limit of Detection (LOD)=1087 GCE/mL, Lower Limit of Quantification (LLOQ)=3261 GCE/mL. Time points with no available results in the treatment group were graphed as 500 GCE/mL—Genome copy equivalents per mL determined by quantitative real-time PCR; * Single subject in Group L.

$8.9 \times 10^4$ GCE/mL, respectively. Seven days after a single vaccination, the numbers of subjects who showed reportable viremia results were notably decreased in all study arms, with mean values of plasma viral RNA ranging from 8814.0 GCE/mL (Group L) to 27,028.0 GCE/mL (Group H). No subject in any dose arm showed a reportable viremia result on Day 14 (FIG. 17A). No viremia was detected after challenge at Day 180 or Month 12 (FIG. 17B). Urinary shedding was detected in a single subject from Group L at

TABLE 13

Related unsolicited AE up to 28 days after vaccination (Groups L, M and H) and re-vaccination (challenge) (Groups L, M, H1 and H2)

| | | After Vaccination | | | After Re-vaccination | Paired Signed rank test | |
|---|---|---|---|---|---|---|---|
| | | | | | Group H2 (N = 26) Group L (N = 22) | Day 7 after vaccination vs. | Day 28 after vaccination vs. |
| | Statistics | Group L (N = 31) | Group M (N = 30) | Group H (N = 59) | Group M (N = 22) Group H1 (N = 18) | Day 7 after re-vaccination | Day 28 after re-vaccination |
| Blood and lymphatic system disorders | n (%) Obs | 6 (19.4) 12 | 4 (13.3) 7 | 17 (28.8) 32 | 0 (0) 0 | | |
| Leukopenia | n (%) Obs | 6 (19.4) 6 | 2 (6.7) 2 | 14 (23.7) 14 | 0 (0) 0 | Group H2 <.0001 <br> Group L <.0001 <br> Group M <.0001 <br> Group H1 <.0001 | 0.1751 <br> 0.9296 <br> 0.7215 <br> 0.5218 |
| Neutropenia | n (%) Obs | 5 (16.1) 5 | 1 (3.3) 3 | 10 (16.9) 10 | 0 (0) 0 | Group H2 <.0001 <br> Group L <.0001 <br> Group M 0.0003 <br> Group H1 <.0001 | 0.1708 <br> 0.9765 <br> 0.7656 <br> 0.8801 |
| Lymphopenia | n (%) Obs | 1 (3.2) 1 | 2 (6.7) 2 | 4 (6.8) 5 | 0 (0) 0 | Group H2 <.0001 <br> Group L 0.0002 <br> Group M <.0001 <br> Group H1 <.0001 | 0.8339 <br> 0.8831 <br> 0.2870 <br> 0.6995 | n . . . number of participants with AE, percentages are based on N, Obs . . . number of events Plasma and urine samples were screened for viremia and viral shedding by PCR as described above. Viremia peaked at Day 3 post immunization in all groups, with the highest mean genome copy equivalent (GCE) value in Group H ($2.3 \times 10^5$ GCE/mL). GCE values in Groups L and M were considerably lower, reaching mean titers of $7.4 \times 10^4$ and Day 7 following vaccination ($1.1 \times 10^4$ GCE/mL) (FIG. 18A) and was not detected at all after challenge at Day 180 or Month 12 (FIG. 18B).

Post-hoc analyses on solicited AEs were performed in order to separate AEs arising before and after re-vaccination. In addition, a statistical comparison of rates of abnormal lymphocyte, neutrophil, and leukocyte counts between 7 and 28 days after single and any re-vaccination was performed.

Example 4. Immunogenicity Studies

Figure 20:
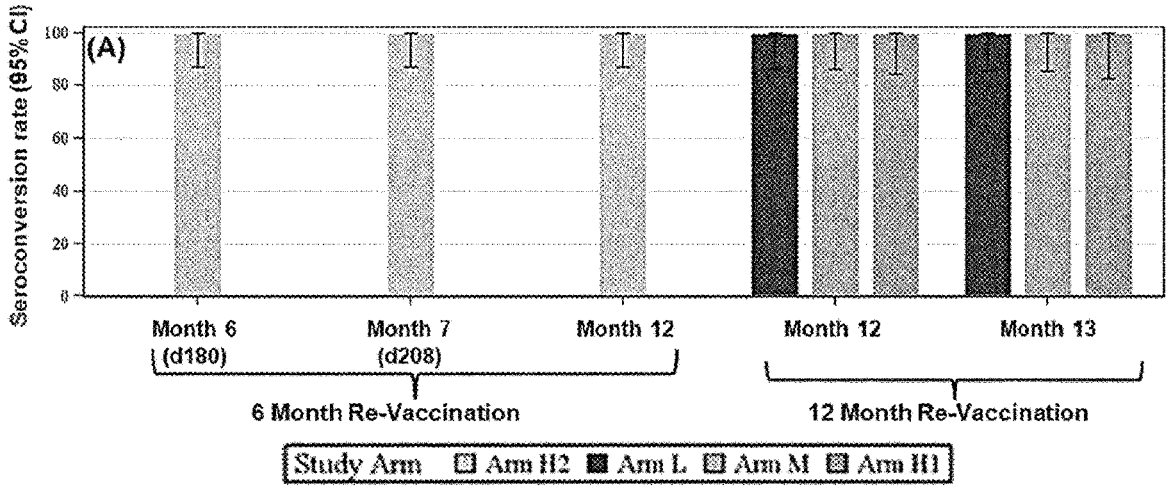
FIG. 20 Assessment of neutralizing antibodies after challenge at Day 180 (M6) or Month 12 (M12). Seroconversion rates (A) and Geometric Mean Titer (B) in Groups L, M, H1 and H2 before and after re-vaccination with the highest dose at Month 6 or Month 12. Seroconversion was defined for the purposes of the trial as the percentage of subjects reaching a CHIKV-specific antibody titer of at least 20 ($\mu NT_{50} \geq 20$).
Figure 20:
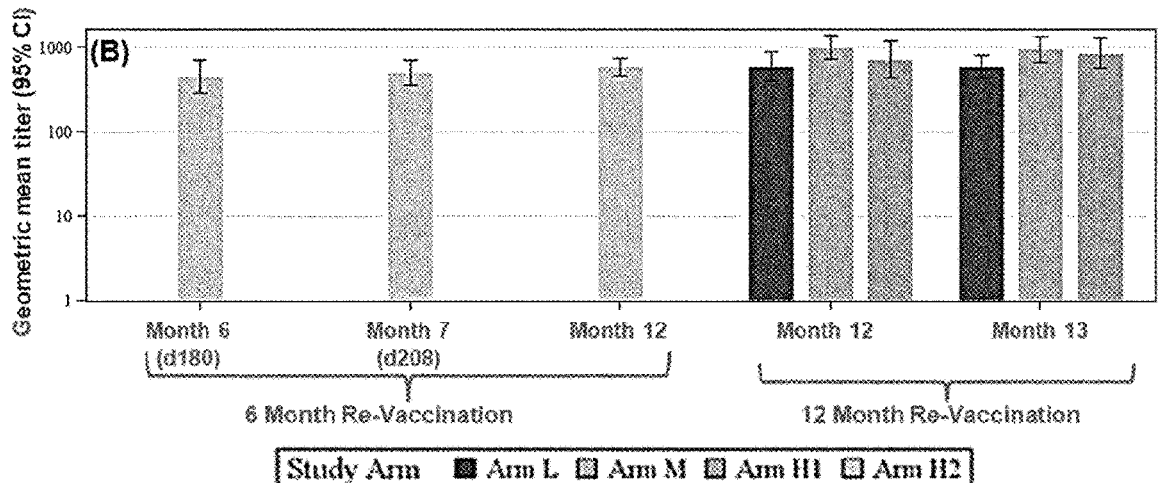

A. Neutralizing Antibody Titers and Seroprotection Conferred by the Single-Shot CHIKV-Δ5nsP3 Vaccine Secondary objectives of the clinical trial included the immune response after the single vaccination, measured by CHIKV-specific neutralizing antibodies, identification of the optimal dose level of the live-attenuated vaccine candidate, subjects, in Groups L, M, H1 and H2, respectively, was observed following challenge, indicating sterilizing immunity as characterized by a less than or equal to a four-fold rise in antibody titers as compared to pre-challenge titers (FIG. 20A and Table 14). Prior to challenge, the Group H2 GMT persisted at 452.5 (range 40-2560) and remained unchanged 28 days post challenge at 490.2 (range 80-2560) (FIG. 20B). Similarly, 28 days after challenge at Month 12 (Month 13), antibody levels in Groups L, M and H1 remained the same as prior to challenge (FIG. 20B).

TABLE 14

Rates of participants within ≤4-Fold Increase in Neutralizing Antibody Titer 28 days after Challenge at Month 6 and Month 12.

|  | Statistics | Group L (N = 23) | Group M (N = 23) | Group H1 (N = 20) | Group H2 (N = 26) |
|---|---|---|---|---|---|
| Reaching <= 4-fold increase | n/N (%) [95% CI] | 22/22 (100) [85.1, 100] | 22/22 (100) [85.1, 100] | 17/18 (94.4) [74.2, 99.0] | 25/26 (96.2) [81.1, 99.3] | n . . . number of participants assessment of immunogenicity of CHIKV-Δ5nsP3 after challenge and assessment of antibody persistence up to Month 12 after a single vaccination. Neutralizing antibodies to the vaccine were evaluated using a microneutralization assay ($\mu$NT), which is based on a colorimetric CPE readout. Briefly, equal volumes of serial two-fold dilutions of serum samples were mixed with CHIKV-Δ5nsP3 (at a concentration resulting in 100% CPE) and incubated for 1-2 h at 37° C., prior to transfer onto Vero cells plated in 96 well plates. After several days, inhibition of Vero cell infection was observed by assessing cell viability. The neutralizing titer is defined as the reciprocal serum dilution which induces 50% protection from cell death ($\mu NT_{50}$) compared with the virus control lacking neutralizing antibody. Titers below the quantification limit ($\mu NT_{50} < 20$) were given the value of 10. Seroconversion was defined as reaching a CHIKV-specific neutralizing antibody titer of at least 20 for baseline seronegative subjects; i.e., $\mu NT_{50} \geq 20$.

The immunogenicity analyses were a comparison of the Geometric Mean Titers (GMTs) and Seroconversion Rates (SCRs) in the per-protocol (PP) population between the dose Groups L, M and H, at Day 28 (i.e. 28 days after vaccination) by ANOVA (factors dose group covariate study site). In addition, GMTs and Geometric Mean Fold Increases (GMFIs) were compared overall and pair-wise (Tukey's HSD test) between dose groups at all time points. All analyses were done in SAS (Version 9.3).

Figure 19:
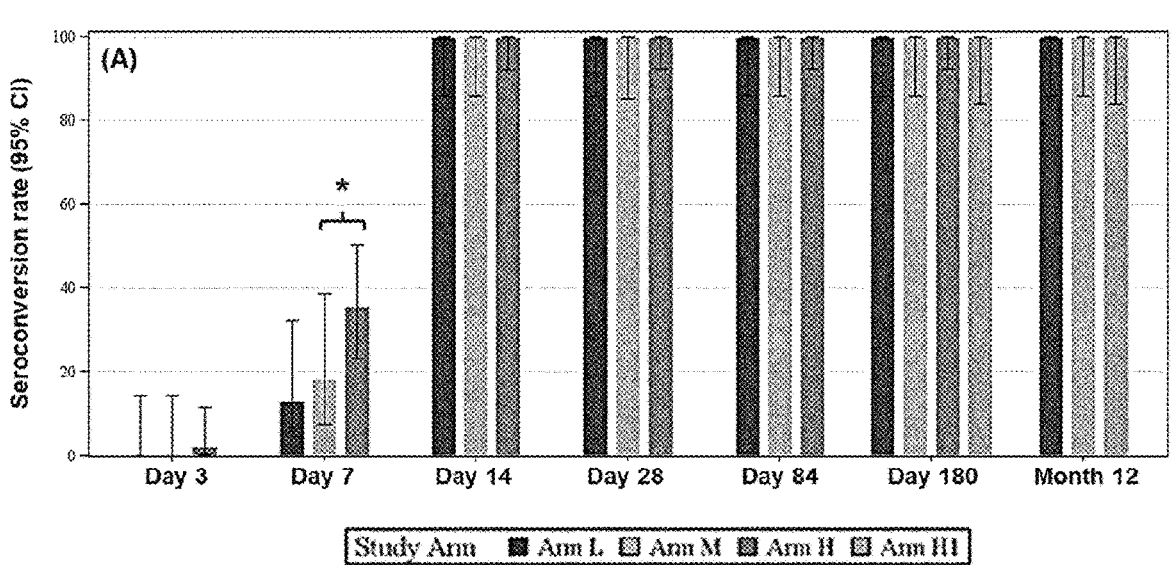
FIG. 19 Assessment of neutralizing antibodies after single vaccination. Seroconversion rates (A) and Geometric Mean Titer (B) after single vaccination by study group. The seroconversion rate was defined for the purposes of the trial as the percentage of subjects reaching a CHIKV-specific antibody titer of at least 20 ($\mu NT_{50} \geq 20$). * Pairwise test p=0.0092.
Figure 19:
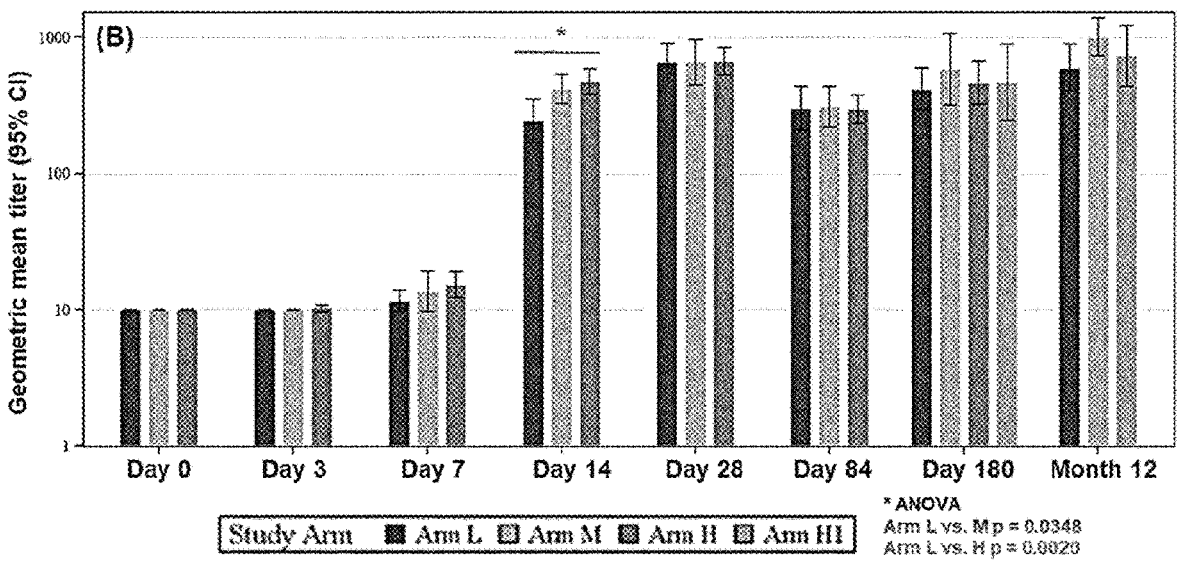

All three vaccine dosages were highly immunogenic after a single vaccination. At 14 days after the single vaccination, 100% of subjects in all dosage groups seroconverted. (Seroconversion was defined as subjects achieving a CHIKV-specific neutralizing antibody titer of at least 20 [$\mu NT_{50} \geq 20$]). Furthermore, seroconversion rates in all dosage groups were sustained until Month 12 (FIG. 19A). At least a 16-fold increase in antibody titers at Day 28 was observed in 96.3% or more subjects in all dosage groups. By Day 28, the highest CHIKV-specific neutralizing GMTs ranged from 592.6 to 686.9, representing a more than 60-fold increase in titers over baseline (FIG. 19B). Peak measured titers of individuals reached up to 10,240 (Groups M and H).

Figure 21:
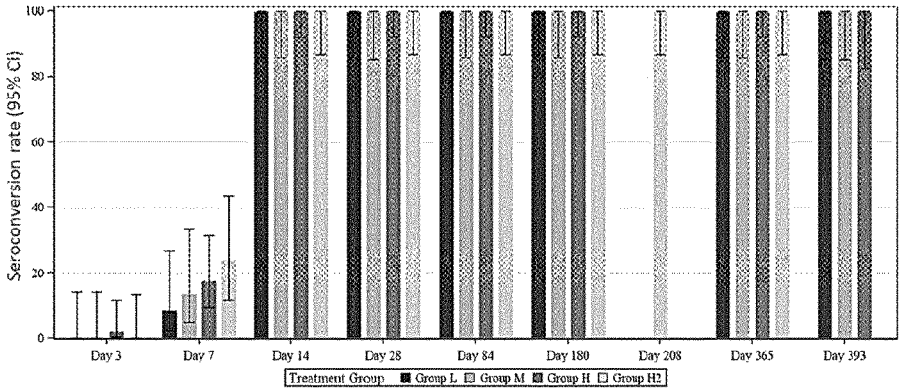
FIG. 21 Assessment of seroconversion rates using increasingly stringent cutoff values. Seroconversion rate defined as percentage of subjects reaching a CHIKV-specific antibody titer of at least (A) 40 ($\mu NT_{50}$ 1:40), (B) 80 ($\mu NT_{50}$ 1:80) and (C) 160 ($\mu NT_{50}$ 1:160) after single and re-vaccination by study day and treatment groups.
Figure 21:
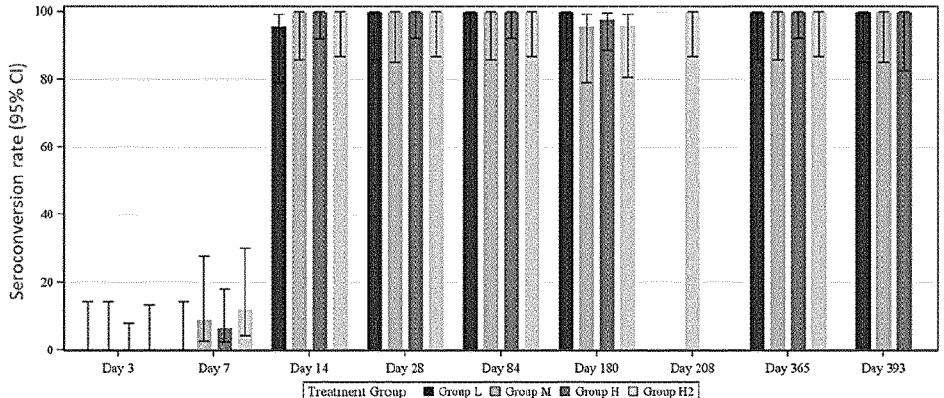
Figure 21:
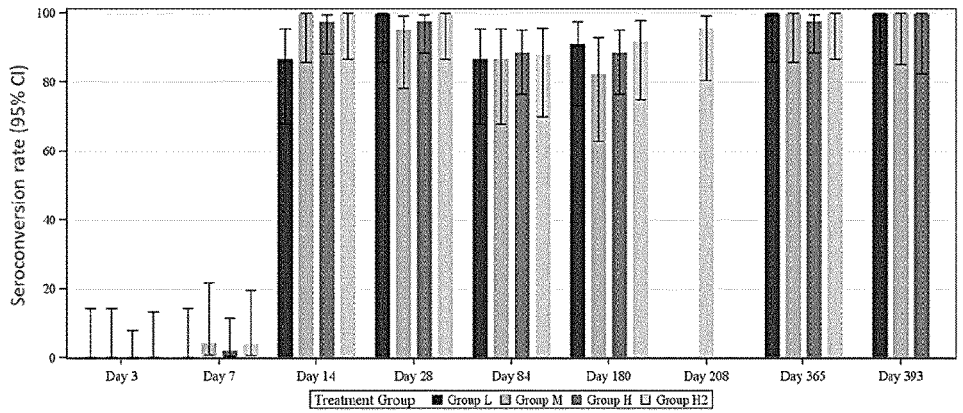
Figure 22:
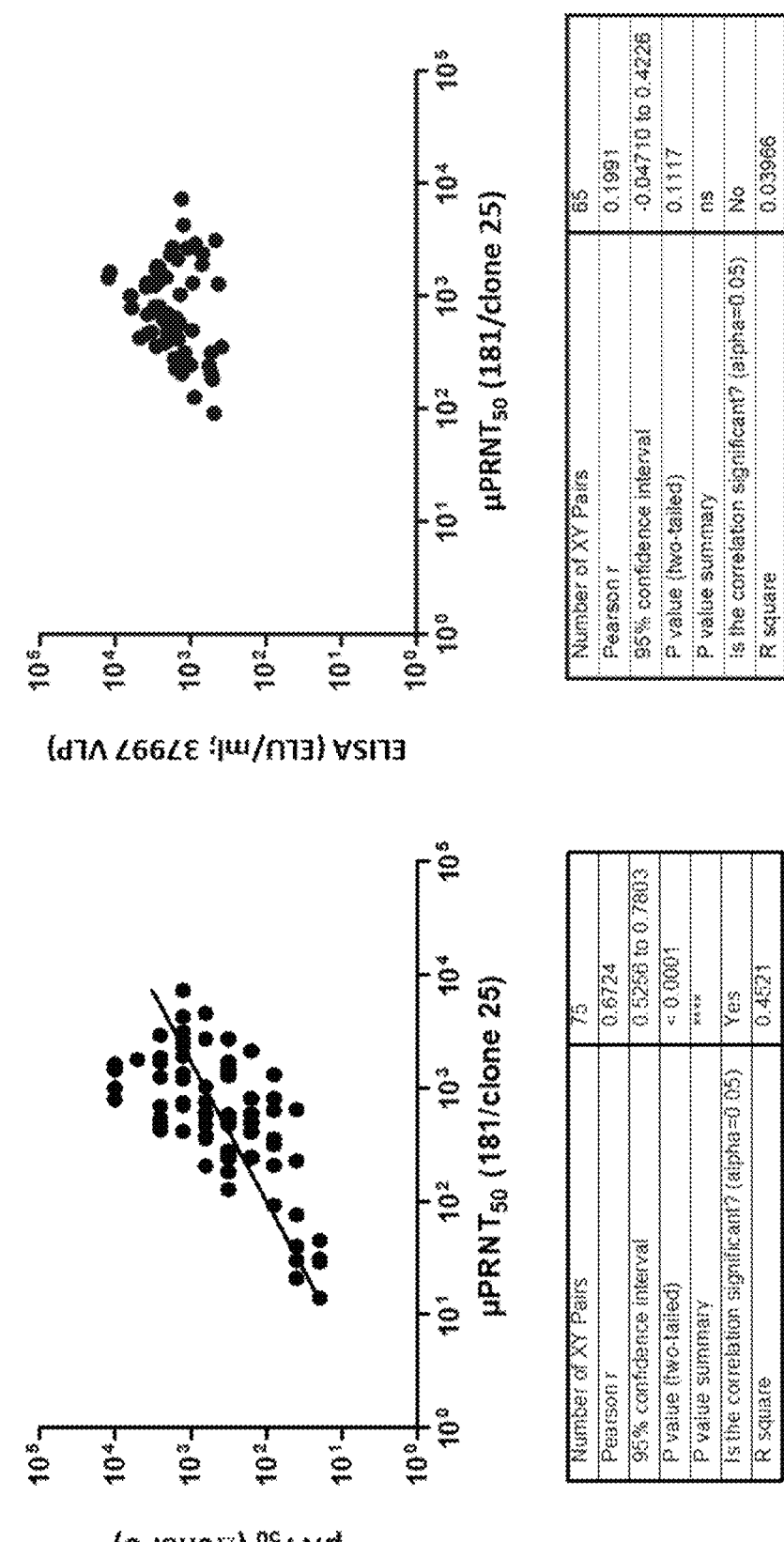
FIG. 22 (A) Correlation of neutralization titers of a panel of 111 CHIKV-Δ5nsP3 phase 1 sera from different time points tested in μNT against the vaccine strain CHIKV-Δ5nsP3 (based on the La Reunion strain (LR2006-OPY1) of the East Central South African (ECSA) genotype) and in μPRNT against the attenuated CHIKV strain 181/clone 25 of the Asian genotype. Correlation of titers was calculated by Pearson correlation coefficient using all samples with titers ≥LLOQ in both assays (n=75) (Only samples with positive titers were shown.) (B) Correlation of neutralization titer of CHIKV-Δ5nsP3 sera tested in pPRNT against CHIKV strain 181/clone 25 of the Asian genotype and CHIKV total IgG ELISA titer (based on viral proteins C, E1 and E2 from West African strain 37997). Correlation of titers was calculated by Pearson correlation coefficient using all samples with titers ≥LLOQ in both assays (n=65) (Only positive titers were shown in the analysis.)

A lack of an anamnestic response, i.e., a booster effect of the challenge dose, in 100%, 100%, 94.4% and 96.2% of Setting the seroprotective threshold When transposing the seroprotective threshold established by Yoon et al. 2015 (supra) to the results of the current study, a titer of >1:10 is achieved by Day 14 in 100% of the subjects. Since the PRNT assay used by Yoon et al. and the microneutralization assay used within our study are based on the same principle, albeit in a different format and tested against different viruses, results are not directly comparable. As discussed herein, the PRNT determines virus neutralization by reduction of plaques using the attenuated CHIKV strain 181/clone 25, whereas the $\mu$NT determines neutralization of the attenuated CHIKV-Δ5nsP3 by reduction of virus-induced cytopathic effect. But even using the conservative seroprotective threshold of $\mu NT_{50} \geq 20$ as applied in the current Phase 1 study, all subjects developed neutralizing antibody titers by Day 14, which were sustained throughout Month 12 following a single vaccination (FIG. 19A). Stressing this even further by using an unlikely seroprotection threshold titer of $\mu NT_{50} \geq 40$ to $\geq 80$, still nearly 100% of subjects across the different doses would be protected after a single vaccination with CHIKV-Δ5nsP3 by Day 14 (FIGS. 21A and 21B). When applying even an unreasonably high threshold titer of $\mu NT_{50} \geq 160$, greater than 90% of subjects across all doses would be protected after a single vaccination with CHIKV-Δ5nsP3 at least until Month 12 (FIG. 21C). Based on the high and persisting geometric mean antibody titers elicited by the single-shot live-attenuated CHIKV vaccine CHIKV-Δ5nsP3, neutralizing antibody levels obtained should be well above the surrogate endpoint indicative of protection. Microneutralization PRNT Titers Against Asian CHIKV Strain Suggest Robust Cross-Neutralization Elicited by the CHIKV-Δ5nsP3 Vaccine For assessment of cross-neutralizing activity of antibodies elicited by the CHIKV-Δ5nsP3 vaccine, a panel of sera from the clinical study from different time points were also tested in a $\mu$PRNT assay for neutralizing capacity against the attenuated heterologous CHIKV strain 181/clone 25 of the Asian genotype. A total of 111 single sera (including 37 pre-vaccination samples) and 5 human serum pools associated with VLA1553-101 study were tested. One pPRNT result was invalid due to the sample crossing the 50% neutralization threshold twice. The correlation between positive titers (n=75) measured by $\mu$NT and $\mu$PRNT was calculated using the Pearson correlation coefficient. As shown in FIG. 22, there was a highly statistically significant correlation of the neutralization titers of sera tested against the vaccine strain CHIKV-Δ5nsP3 (del5nsP3), based on LR2006-OPY1 of the East Central South African (ECSA) genotype and CHIKV strain 181/clone 25 of the Asian genotype. It was observed that antibodies induced by the CHIKV-Δ5nsP3 vaccine also efficiently neutralized the 181/clone 25 Asian CHIKV strain. Furthermore, neutralizing antibody titer values against both strains were highly similar in spite of being obtained using different assay formats (µNT v. µPRNT). This data strongly suggests that the CHIKV-Δ5nsP3 vaccine may confer protection against more than one strain of CHIKV.

While cross-neutralization between different CHIKV genotypes has already been shown in the literature, the results obtained during the feasibility study provided further insight into the cross-neutralizing ability of the CHIKV-Δ5nsP3-induced antibodies. Due to differences in assay systems, slight differences in the reported results were nevertheless expected. To support the results obtained from the µPRNT, anti-CHIKV total IgG antibodies were quantified by ELISA, using a CHIKV virus-like particle (E1, E2 and C1 proteins from West African strain 37997) and results were compared.

Methodology

In the course of clinical development, serum samples selected from the current study were tested using a micro-neutralization test (µNT) which measured the neutralization of CHIKV-Δ5nsP3, a micro-plaque reduction neutralization test (µPRNT) which measured neutralization of 181/clone 25 CHIKV and a Chikungunya virus-like particle (VLP)-based IgG ELISA based on the 37997 West African 37997 CHIKV strain. The purified CHIKV virus-like particles (VLPs) for ELISA comprised viral proteins C, E1 and E2 from the West African strain. Serum samples were selected based on neutralization titer obtained during clinical testing to span the titer range and dependent on sample availability. A panel of 111 CHIKV-Δ5nsP3 human serum samples were included in this comparability study. All three assays were compared in terms of correlation of results and assay characteristics.

Comparison of CHIKV µNT, µPRNT and IgG ELISA

A sub-set of the 111 clinical serum samples were analyzed in µNT, µPRNT and ELISA assays. The correlation between log-transformed titers measured with µNT, µPRNT and ELISA was calculated using the Pearson correlation coefficient (Pearson r), where a value of "1" indicates total positive linear correlation and a value of "0" indicates no linear correlation. Samples with titers below the lower limit of quantification (LLOQ) as well as positive controls were excluded from the correlation analysis. As shown in FIG. 22A, the value obtained for Pearson r with regard to µNT and µPRNT was 0.6724, indicating a moderately strong positive correlation. Moreover, the fact that titers obtained with µPRNT and µNT were comparable indicates a cross-protective ability of CHIKV-Δ5nsP3 against the Asian lineage of CHIKV (181/clone 25).

By contrast, the Pearson r value obtained for µPRNT and ELISA results was 0.1991, indicating only a weak positive correlation (see FIG. 22B). This finding is also reflected in the narrower distribution of titers measured by ELISA compared to titers measured with µPRNT. Presumably, functional differences of CHIKV antibodies, which become apparent in neutralization assays, are not detectable by ELISA. While ELISA measures only total CHIKV-specific IgG antibodies, µPRNT detects CHIKV-neutralizing antibodies of all isotypes. Nevertheless, all samples with positive ELISA titers also showed positive µPRNT titers, an observation supporting a predictive value of ELISA in anti-CHIKV immune responses. All post-vaccination samples from day 14 and later tested positive in ELISA. As CHIKV strains derived from different CHIKV lineages than the vaccine strain CHIKV-Δ5nsP3 (ECSA) were employed in both µPRNT (strain 181/clone 25 Asian) and ELISA (West African strain 37997), the ability of CHIKV-Δ5nsP3 to induce to cross-neutralizing antibodies is further supported.

Early seroconversion A total of ten Visit 1B samples (Day 7±1 day post vaccination) from all groups were included in a study to analyze test performance with samples collected during the early phase of the immune response (see Table A1). All of the samples tested had IgG levels below the LOD in the CHIKV IgG ELISA, indicating the absence of CHIKV-specific IgG antibodies at this early time point after vaccination. However, all except for two Visit 1B samples tested positive in µPRNT and all tested positive in µNT assays, due to the presence of CHIKV-neutralizing IgM antibodies at this early time point.

TABLE A1

| ELISA, µPRNT and µNT results for CHIKV-Δ5nsP3 trial sera from visit 1B (day 7 ± 1 post vaccination). | | |
|---|---|---|
| ELISA (ELU/mL) (VLP 37997 WA) | $\mu PRNT_{50}$ (CHIKV 181/ clone 25 Asian) | $\mu NT_{50}$ (CHIKV-Δ5nsP3 ECSA) |
| <14.7 | <10 | 20 |
| <14.7 | 21 | 40 |
| <14.7 | 29 | 20 |
| <14.7 | 14 | 20 |
| <14.7 | 40 | 40 |
| <14.7 | <10 | 20 |
| <14.7 | 30 | 40 |
| <14.7 | 45 | 20 |
| <14.7 | 76 | 40 |
| <14.7 | 31 | 20 |

Figure 23:
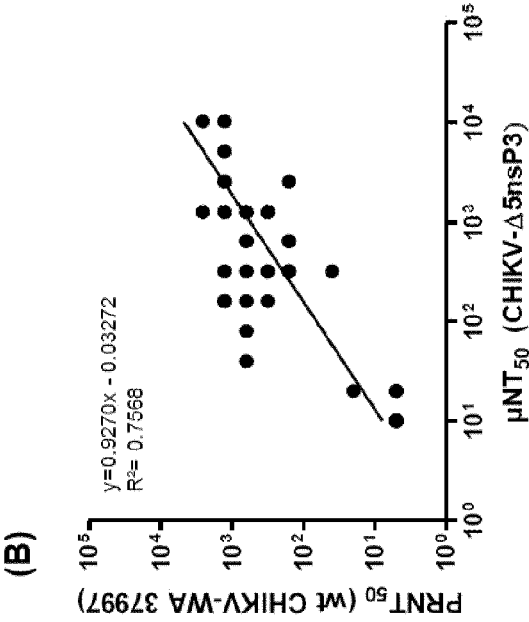
FIG. 23 Pair-wise comparison of neutralization titers of CHIKV-Δ5nsP3 trial sera collected at different visits of individual subjects measured against the vaccine strain CHIKV-Δ5nsP3 ($\mu NT_{50}$) and (A) the wild-type La Reunion strain ($PRNT_{50}$ wt CHIKV-LR) and (B) the wild type West African strain 37997 ($PRNT_{50}$ wt CHIKV-WA 37997). Three samples having a titer >5,120 in the $PRNT_{50}$ wt CHIKV-LR assay are plotted as 5,120. Negative samples were imputed with half the LLOQ for each method ($\mu NT_{50}$=10, $PRNT_{50}$=5).
Figure 23:
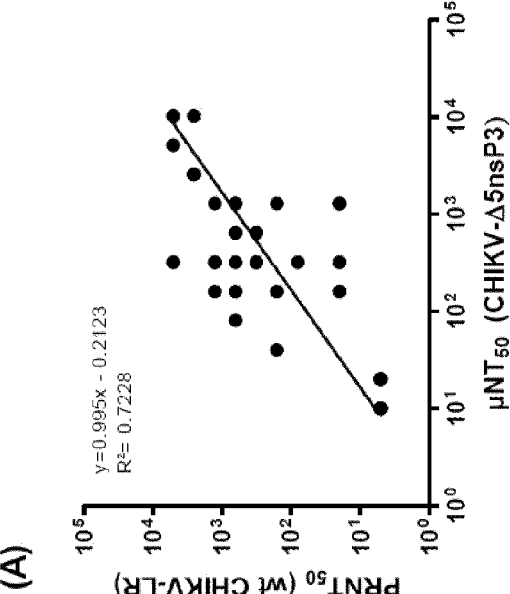

Patient sera from CHIKV-Δ5nsP3 trial neutralized wild-type CHIKV Serum samples from the clinical trial (n=47 single sera) were analyzed to quantify wild-type chikungunya virus (Indian Ocean/ECSA lineage [La Reunion strain; wt CHIKV-LR] and West African strain; wt CHIKV-WA 3797) neutralizing antibodies. Sera collected at different visits of individual subjects were analyzed by PRNT (see FIG. 23). All post VLA1553-101 vaccination samples obtained at Day 14 or later demonstrated substantial neutralizing activity against both wild-type La Reunion CHIKV and a heterologous strain of the West African lineage.

Overall, the neutralization capacity of a particular serum for the attenuated CHIKV-Δ5nsP3 strain as assessed by µNT correlated well with its neutralization capacity for two wild-type CHIKV strains as assessed by PRNT. The results not only demonstrated the cross-neutralizing capacity of the CHIKV-Δ5nsP3 vaccine, but also showed the comparability of titer values obtained using the µNT assay and the PRNT assay.

B. GMT Values from CHIKV-Δ5nsP3 Clinical Trial Sera and Convalescent Human Sera Comparable GMTs conferred by natural exposure to CHIKV Antibodies conferred by natural infection are hypothesized to provide life-long protection against CHIKV fever (Galatas, et al. and Nitatpattana, et al.; supra); therefore, the µNT titers observed in the present clinical samples were compared with neutralizing antibody titers in individuals convalescing from natural infection. Fourteen serum samples from individuals recovered from Chikungunya infection (kindly provided by World Reference Center for Emerging Viruses and Arboviruses (WRCEVA) through the University of Texas Medical Branch (UTMB) or purchased from SeraCare and Biomex) were tested in the CHIKV-Δ5nsP3 NT assay as used in the current clinical study. The neutralization titers of convalescent sera from all three sources were comparable (see Table A2). Furthermore, titers were similar to those observed after a single vaccination with CHIKV-Δ5nsP3, which reached GMT values up to 2560 at Day 28 in all dose groups.

TABLE A2

| Neutralization titers from convalescent serum samples from naturally-infected patients. | |
| --- | --- |
| Sample | $\mu NT_{50}$ |
| Sera Care #2 | 640 |
| Sera Care #8 | 1,280 |

TABLE A2-continued

| Neutralization titers from convalescent serum samples from naturally-infected patients. | |
| --- | --- |
| Sample | $\mu NT_{50}$ |
| Sera Care #10 | 2,560 |
| Biomex | 1,280 |
| UTMB #1 | 1,280 |
| UTMB #2 | 2,560 |
| UTMB #3 | 2,560 |
| UTMB #4 | 1,280 |
| UTMB #5 | 2,560 |
| UTMB #6 | 5,120 |
| UTMB #7 | 1,280 |
| UTMB #8 | 1,280 |
| UTMB #9 | 1,280 |
| UTMB #10 | 5,120 |

SEQUENCES

```
Nucleotide sequence of the CHIKV-Δ5nsP3
                                                          SEQ ID NO: 1
GATGGCTGCGTGAGACACACGTAGCCTACCAGTTTCTTACTGCTCTACTCTGCAAAGCAAGAGAT

TAATAACCCATCATGGATCCTGTGTACGTGGACATAGACGCTGACAGCGCCTTTTTGAAGGCCCT

GCAACGTGCGTACCCCATGTTTGAGGTGGAACCAAGGCAGGTCACACCGAATGACCATGCTAAT

GCTAGAGCGTTCTCGCATCTAGCTATAAAACTAATAGAGCAGGAAATTGACCCCGACTCAACCAT

CCTGGATATCGGCAGTGCGCCAGCAAGGAGGATGATGTCGGACAGGAAGTACCACTGCGTCTG

CCCGATGCGCAGTGCGGAAGATCCCGAGAGACTCGCCAATTATGCGAGAAAGCTAGCATCTGCC

GCAGGAAAAGTCCTGGACAGAAACATCTCTGGAAAGATCGGGGACTTACAAGCAGTAATGGCCG

TGCCAGACACGGAGACGCCAACATTCTGCTTACACACAGACGTCTCATGTAGACAGAGAGCAGA

CGTCGCTATATACCAAGACGTCTATGCTGTACACGCACCCACGTCGCTATACCACCAGGCGATTA

AAGGGGTCCGAGTGGCGTACTGGGTTGGGTTCGACACAACCCCGTTCATGTACAATGCCATGGC

GGGTGCCTACCCCTCATACTCGACAAACTGGGCAGATGAGCAGGTACTGAAGGCTAAGAACATA

GGATTATGTTCAACAGACCTGACGGAAGGTAGACGAGGCAAGTTGTCTATTATGAGAGGGAAAAA

GCTAAAACCGTGCGACCGTGTGCTGTTCTCAGTAGGGTCAACGCTCTACCCGGAAAGCCGCAAG

CTACTTAAGAGCTGGCACCTGCCATCGGTGTTCCATTTAAAGGGCAAACTCAGCTTCACATGCCG

CTGTGATACAGTGGTTTCGTGTGAGGGCTACGTCGTTAAGAGAATAACGATGAGCCCAGGCCTTT

ATGGAAAAACCACAGGGTATGCGGTAACCCACCACGCAGACGGATTCCTGATGTGCAAGACTAC

CGACACGGTTGACGGCGAAAGAATGTCATTCTCGGTGTGCACATACGTGCCGGCGACCATTTGT

GATCAAATGACCGGCATCCTTGCTACAGAAGTCACGCCGGAGGATGCACAGAAGCTGTTGGTGG

GGCTGAACCAGAGAATAGTGGTTAACGGCAGAACGCAACGGAATACGAACACCATGAAAAATTAT

CTGCTTCCCGTGGTCGCCCAAGCCTTCAGTAAGTGGGCAAAGGAGTGCCGGAAAGACATGGAAG

ATGAAAAACTCCTGGGGGTCAGAGAAAGAACACTGACCTGCTGCTGTCTATGGGCATTCAAGAAG

CAGAAAACACACACGGTCTACAAGAGGCCTGATACCCAGTCAATTCAGAAGGTTCAGGCCGAGTT

TGACAGCTTTGTGGTACCGAGTCTGTGGTCGTCCGGGTTGTCAATCCCTTTGAGGACTAGAATCA

AATGGTTGTTAAGCAAGGTGCCAAAAACCGACCTGATCCCATACAGCGGAGACGCCCGAGAAGC

CCGGGACGCAGAAAAAGAAGCAGAGGAAGAACGAGAAGCAGAACTGACTCGCGAAGCCCTACC

ACCTCTACAGGCAGCACAGGAAGATGTTCAGGTCGAAATCGACGTGGAACAGCTTGAGGACAGA

GCGGGCGCAGGAATAATAGAGACTCCGAGAGGAGCTATCAAAGTTACTGCCCAACCAACAGACC
```

ACGTCGTGGGAGAGTACCTGGTACTCTCCCCGCAGACCGTACTACGTAGCCAGAAGCTCAGTCT

GATTCACGCTTTGGCGGAGCAAGTGAAGACGTGCACGCACAACGGACGAGCAGGGAGGTATGC

GGTCGAAGCGTACGACGGCCGAGTCCTAGTGCCCTCAGGCTATGCAATCTCGCCTGAAGACTTC

CAGAGTCTAAGCGAAAGCGCAACGATGGTGTATAACGAAAGAGAGTTCGTAAACAGAAAGCTACA

CCATATTGCGATGCACGGACCAGCCCTGAACACCGACGAAGAGTCGTATGAGCTGGTGAGGGCA

GAGAGGACAGAACACGAGTACGTCTACGACGTGGATCAGAGAAGATGCTGTAAGAAGGAAGAAG

CCGCAGGACTGGTACTGGTGGGCGACTTGACTAATCCGCCCTACCACGAATTCGCATATGAAGG

GCTAAAAATCCGCCCTGCCTGCCCATACAAAATTGCAGTCATAGGAGTCTTCGGAGTACCGGGAT

CTGGCAAGTCAGCTATTATCAAGAACCTAGTTACCAGGCAGGACCTGGTGACTAGCGGAAAGAAA

GAAAACTGCCAAGAAATCACCACCGACGTGATGAGACAGAGAGGTCTAGAGATATCTGCACGTA

CGGTTGACTCGCTGCTCTTGAATGGATGCAACAGACCAGTCGACGTGTTGTACGTAGACGAGGC

GTTTGCGTGCCACTCTGGAACGCTACTTGCTTTGATCGCCTTGGTGAGACCAAGGCAGAAAGTTG

TACTTTGTGGTGACCCGAAGCAGTGCGGCTTCTTCAATATGATGCAGATGAAAGTCAACTATAATC

ACAACATCTGCACCCAAGTGTACCACAAAAGTATCTCCAGGCGGTGTACACTGCCTGTGACCGCC

ATTGTGTCATCGTTGCATTACGAAGGCAAAATGCGCACTACGAATGAGTACAACAAGCCGATTGT

AGTGGACACTACAGGCTCAACAAAACCTGACCCTGGAGACCTCGTGTTAACGTGCTTCAGAGGG

TGGGTTAAACAACTGCAAATTGACTATCGTGGATACGAGGTCATGACAGCAGCCGCATCCCAAGG

GTTAACCAGAAAAGGAGTTTACGCAGTTAGACAAAAAGTTAATGAAAACCCGCTCTATGCATCAAC

GTCAGAGCACGTCAACGTACTCCTAACGCGTACGGAAGGTAAACTGGTATGGAAGACACTTTCC

GGCGACCCGTGGATAAAGACGCTGCAGAACCCACCGAAAGGAAACTTCAAAGCAACTATTAAGG

AGTGGGAGGTGGAGCATGCATCAATAATGGCGGGCATCTGCAGTCACCAAATGACCTTCGATAC

ATTCCAAAATAAAGCCAACGTTTGTTGGGCTAAGAGCTTGGTCCCTATCCTCGAAACAGCGGGGA

TAAAACTAAATGATAGGCAGTGGTCTCAGATAATTCAAGCCTTCAAAGAAGACAAAGCATACTCAC

CTGAAGTAGCCCTGAATGAAATATGTACGCGCATGTATGGGGTGGATCTAGACAGCGGGCTATTT

TCTAAACCGTTGGTGTCTGTGTATTACGCGGATAACCACTGGGATAATAGGCCTGGAGGGAAAT

GTTCGGATTTAACCCCGAGGCAGCATCCATTCTAGAAAGAAAGTATCCATTCACAAAAGGGAAGT

GGAACATCAACAAGCAGATCTGCGTGACTACCAGGAGGATAGAAGACTTTAACCCTACCACCAAC

ATCATACCGGCCAACAGGAGACTACCACACTCATTAGTGGCCGAACACCGCCCAGTAAAAGGGG

AAAGAATGGAATGGCTGGTTAACAAGATAAACGGCCACCACGTGCTCCTGGTCAGTGGCTATAAC

CTTGCACTGCCTACTAAGAGAGTCACTTGGGTAGCGCCGTTAGGTGTCCGCGGAGCGGACTACA

CATACAACCTAGAGTTGGGTCTGCCAGCAACGCTTGGTAGGTATGACCTAGTGGTCATAAACATC

CACACACCTTTTCGCATACACCATTACCAACAGTGCGTCGACCACGCAATGAAACTGCAAATGCT

CGGGGGTGACTCATTGAGACTGCTCAAACCGGGCGGCTCTCTATTGATCAGAGCATATGGTTAC

GCAGATAGAACCAGTGAACGAGTCATCTGCGTATTGGGACGCAAGTTTAGATCGTCTAGAGCGTT

GAAACCACCATGTGTCACCAGCAACACTGAGATGTTTTTCCTATTCAGCAACTTTGACAATGGCAG

AAGGAATTTCACAACTCATGTCATGAACAATCAACTGAATGCAGCCTTCGTAGGACAGGTCACCC

GAGCAGGATGTGCACCGTCGTACCGGGTAAAACGCATGGACATCGCGAAGAACGATGAAGAGTG

CGTAGTCAACGCCGCTAACCCTCGCGGGTTACCGGGTGGCGGTGTTTGCAAGGCAGTATACAAA

AAATGGCCGGAGTCCTTTAAGAACAGTGCAACACCAGTGGGAACCGCAAAAACAGTTATGTGCG

GTACGTATCCAGTAATCCACGCTGTTGGACCAAACTTCTCTAATTATTCGGAGTCTGAAGGGGAC

-continued

```
CGGGAATTGGCAGCTGCCTATCGAGAAGTCGCAAAGGAAGTAACTAGGCTGGGAGTAAATAGTG

TAGCTATACCTCTCCTCTCCACAGGTGTATACTCAGGAGGGAAAGACAGGCTGACCCAGTCACTG

AACCACCTCTTTACAGCCATGGACTCGACGGATGCAGACGTGGTCATCTACTGCCGCGACAAAG

AATGGGAGAAGAAAATATCTGAGGCCATACAGATGCGGACCCAAGTAGAGCTGCTGGATGAGCA

CATCTCCATAGACTGCGATATTGTTCGCGTGCACCCTGACAGCAGCTTGGCAGGCAGAAAAGGA

TACAGCACCACGGAAGGCGCACTGTACTCATATCTAGAAGGGACCCGTTTTCATCAGACGGCTGT

GGATATGGCGGAGATACATACTATGTGGCCAAAGCAAACAGAGGCCAATGAGCAAGTCTGCCTA

TATGCCCTGGGGGAAAGTATTGAATCGATCAGGCAGAAATGCCCGGTGGATGATGCAGACGCAT

CATCTCCCCCCAAAACTGTCCCGTGCCTTTGCCGTTACGCTATGACTCCAGAACGCGTCACCCG

GCTTCGCATGAACCACGTCACAAGCATAATTGTGTGTTCTTCGTTTCCCCTCCCAAAGTACAAAT

AGAAGGAGTGCAAAAAGTCAAATGCTCTAAGGTAATGCTATTTGACCACAACGTGCCATCGCGCG

TAAGTCCAAGGGCTTATAGAGGTGCCGCTGCCGGTAACCTTGCGGCCGTGTCTGATTGGGTAAT

GAGCACCGTACCTGTCGCGCCGCCCAGAAGAAGGCGAGGGAGAAACCTGACTGTGACATGTGA

CGAGAGAGAAGGGAATATAACACCCATGGCTAGCGTCCGATTCTTTAGGGCAGAGCTGTGTCCG

GTCGTACAAGAAACAGCGGAGACGCGTGACACAGCAATGTCTCTTCAGGCACCACCGAGTACCG

CCACGGAACCGAATCATCCGCCGATCTCCTTCGGAGCATCAAGCGAGACGTTCCCCATTACATTT

GGGGACTTCAACGAAGGAGAAATCGAAAGCTTGTCTTCTGAGCTACTAACTTTCGGAGACTTCTT

ACCAGGAGAAGTGGATGACTTGACAGACAGCGACTGGTCCACGTGCTCAGACACGGACGACGA

GTTAAGACTAGACAGGGCAGGTGGGTATATATTCTCGTCGGACACCGGTCCAGGTCATTTACAAC

AGAAGTCAGTACGCCAGTCAGTGCTGCCGGTGAACACCCTGGAGGAAGTCCACGAGGAGAAGT

GTTACCCACCTAAGCTGGATGAAGCAAAGGAGCAACTATTACTTAAGAAACTCCAGGAGAGTGCA

TCCATGGCCAACAGAAGCAGGTATCAGTCGCGCAAAGTAGAAAACATGAAAGCAGCAATCATCCA

GAGACTAAAGAGAGGCTGTAGACTATACTTAATGTCAGAGACCCCAAAAGTCCCTACTTACCGGA

CTACATATCCGGCGCCTGTGTACTCGCCTCCGATCAACGTCCGATTGTCCAATCCCGAGTCCGCA

GTGGCAGCATGCAATGAGTTCTTAGCTAGAAACTATCCAACTGTCTCATCATACCAAATTACCGAC

GAGTATGATGCATATCTAGACATGGTGGACGGGTCGGAGAGTTGCCTGGACCGAGCGACATTCA

ATCCGTCAAAACTCAGGAGCTACCCGAAACAGCACGCTTACCACGCGCCCTCCATCAGAAGCGC

TGTACCGTCCCCATTCCAGAACACACTACAGAATGTACTGGCAGCAGCCACGAAAAGAAACTGCA

ACGTCACACAGATGAGGGAATTACCCACTTTGGACTCAGCAGTATTCAACGTGGAGTGTTTCAAA

AAATTCGCATGCAACCAAGAATACTGGGAAGAATTTGCTGCCAGCCCTATTAGGATAACAACTGA

GAATTTAGCAACCTATGTTACTAAACTAAAAGGGCCAAAAGCAGCAGCGCTATTCGCAAAAACCC

ATAATCTACTGCCACTACAGGAAGTACCAATGGATAGGTTCACAGTAGATATGAAAAGGGACGTA

AAGGTGACTCCTGGTACAAAGCATACAGAGGAAAGACCTAAGGTGCAGGTTATACAGGCGGCTG

AACCCTTGGCGACAGCATACCTATGTGGGATTCACAGAGAGCTGGTTAGGAGGCTGAACGCCGT

CCTCCTACCCAATGTACATACACTATTTGACATGTCTGCCGAGGATTTCGATGCCATCATAGCCG

CACACTTTAAGCCAGGAGACACTGTTTTGGAAACGGACATAGCCTCCTTTGATAAGAGCCAAGAT

GATTCACTTGCGCTTACTGCTTTGATGCTGTTAGAGGATTTAGGGGTGGATCACTCCCTGCTGGA

CTTGATAGAGGCTGCTTTCGGAGAGATTTCCAGCTGTCACCTACCGACAGGTACGCGCTTCAAGT

TCGGCGCCATGATGAAATCAGGTATGTTCCTAACTCTGTTCGTCAACACATTGTTAAACATCACCA

TCGCCAGCCGAGTGCTGGAAGATCGTCTGACAAAATCCGCGTGCGCGGCCTTCATCGGCGACG

ACAACATAATACATGGAGTCGTCTCCGATGAATTGATGGCAGCCAGATGTGCCACTTGGATGAAC
```

-continued

```
ATGGAAGTGAAGATCATAGATGCAGTTGTATCCTTGAAAGCCCCTTACTTTTGTGGAGGGTTTATA

CTGCACGATACTGTGACAGGAACAGCTTGCAGAGTGGCAGACCCGCTAAAAAGGCTTTTTAAACT

GGGCAAACCGCTAGCGGCAGGTGACGAACAAGATGAAGATAGAAGACGAGCGCTGGCTGACGA

AGTGATCAGATGGCAACGAACAGGGCTAATTGATGAGCTGGAGAAAGCGGTATACTCTAGGTAC

GAAGTGCAGGGTATATCAGTTGTGGTAATGTCCATGGCCACCTTTGCAAGCTCCAGATCCAACTT

CGAGAAGCTCAGAGGACCCGTCATAACTTTGTACGGCGGTCCTAAATAGGTACGCACTACAGCTA

CCTATTTTGCAGAAGCCGACAGCAAGTATCTAAACACTAATCAGCTACAATGGAGTTCATCCCAAC

CCAAACTTTTTACAATAGGAGGTACCAGCCTCGACCCTGGACTCCGCGCCCTACTATCCAAGTCA

TCAGGCCCAGACCGCGCCCTCAGAGGCAAGCTGGGCAACTTGCCCAGCTGATCTCAGCAGTTAA

TAAACTGACAATGCGCGCGGTACCACAACAGAAGCCACGCAGGAATCGGAAGAATAAGAAGCAA

AAGCAAAAACAACAGGCGCCACAAAACAACACAAATCAAAAGAAGCAGCCACCTAAAAAGAAACC

GGCTCAAAAGAAAAAGAAGCCGGGCCGCAGAGAGAGGATGTGCATGAAAATCGAAAATGATTGT

ATTTTCGAAGTCAAGCACGAAGGTAAGGTAACAGGTTACGCGTGCCTGGTGGGGGACAAAGTAA

TGAAACCAGCACACGTAAAGGGGACCATCGATAACGCGGACCTGGCCAAACTGGCCTTTAAGCG

GTCATCTAAGTATGACCTTGAATGCGCGCAGATACCCGTGCACATGAAGTCCGACGCTTCGAAGT

TCACCCATGAGAAACCGGAGGGGTACTACAACTGGCACCACGGAGCAGTACAGTACTCAGGAGG

CCGGTTCACCATCCCTACAGGTGCTGGCAAACCAGGGGACAGCGGCAGACCGATCTTCGACAAC

AAGGGACGCGTGGTGGCCATAGTCTTAGGAGGAGCTAATGAAGGAGCCCGTACAGCCCTCTCG

GTGGTGACCTGGAATAAAGACATTGTCACTAAAATCACCCCCGAGGGGGCCGAAGAGTGGAGTC

TTGCCATCCCAGTTATGTGCCTGTTGGCAAACACCACGTTCCCCTGCTCCCAGCCCCCTTGCACG

CCCTGCTGCTACGAAAAGGAACCGGAGGAAACCCTACGCATGCTTGAGGACAACGTCATGAGAC

CTGGGTACTATCAGCTGCTACAAGCATCCTTAACATGTTCTCCCCACCGCCAGCGACGCAGCACC

AAGGACAACTTCAATGTCTATAAAGCCACAAGACCATACTTAGCTCACTGTCCCGACTGTGGAGA

AGGGCACTCGTGCCATAGTCCCGTAGCACTAGAACGCATCAGAAATGAAGCGACAGACGGGACG

CTGAAAATCCAGGTCTCCTTGCAAATCGGAATAAAGACGGATGACAGCCACGATTGGACCAAGCT

GCGTTATATGGACAACCACATGCCAGCAGACGCAGAGAGGGCGGGGCTATTTGTAAGAACATCA

GCACCGTGTACGATTACTGGAACAATGGGACACTTCATCCTGGCCCGATGTCCAAAAGGGGAAA

CTCTGACGGTGGGATTCACTGACAGTAGGAAGATTAGTCACTCATGTACGCACCCATTTCACCAC

GACCCTCCTGTGATAGGTCGGGAAAAATTCCATTCCCGACCGCAGCACGGTAAAGAGCTACCTT

GCAGCACGTACGTGCAGAGCACCGCCGCAACTACCGAGGAGATAGAGGTACACATGCCCCCAG

ACACCCCTGATCGCACATTAATGTCACAACAGTCCGGCAACGTAAAGATCACAGTCAATGGCCAG

ACGGTGCGGTACAAGTGTAATTGCGGTGGCTCAAATGAAGGACTAACAACTACAGACAAAGTGAT

TAATAACTGCAAGGTTGATCAATGTCATGCCGCGGTCACCAATCACAAAAAGTGGCAGTATAACT

CCCCTCTGGTCCCGCGTAATGCTGAACTTGGGGACCGAAAAGGAAAAATTCACATCCCGTTTCCG

CTGGCAAATGTAACATGCAGGGTGCCTAAAGCAAGGAACCCCACCGTGACGTACGGGAAAAACC

AAGTCATCATGCTACTGTATCCTGACCACCCAACACTCCTGTCCTACCGGAATATGGGAGAAGAA

CCAAACTATCAAGAAGAGTGGGGTGATGCATAAGAAGGAAGTCGTGCTAACCGTGCCGACTGAAG

GGCTCGAGGTCACGTGGGGCAACAACGAGCCGTATAAGTATTGGCCGCAGTTATCTACAAACGG

TACAGCCCATGGCCACCCGCATGAGATAATTCTGTATTATTATGAGCTGTACCCCACTATGACTGT

AGTAGTTGTGTCAGTGGCCACGTTCATACTCCTGTCGATGGTGGGTATGGCAGCGGGGATGTGC
```

-continued

ATGTGTGCACGACGCAGATGCATCACACCGTATGAACTGACACCAGGAGCTACCGTCCCTTTCCT

GCTTAGCCTAATATGCTGCATCAGAACAGCTAAAGCGGCCACATACCAAGAGGCTGCGATATACC

TGTGGAACGAGCAGCAACCTTTGTTTTGGCTACAAGCCCTTATTCCGCTGGCAGCCCTGATTGTT

CTATGCAACTGTCTGAGACTCTTACCATGCTGCTGTAAAACGTTGGCTTTTTTAGCCGTAATGAGC

GTCGGTGCCCACACTGTGAGCGCGTACGAACACGTAACAGTGATCCCGAACACGGTGGGAGTAC

CGTATAAGACTCTAGTCAATAGACCTGGCTACAGCCCCATGGTATTGGAGATGGAACTACTGTCA

GTCACTTTGGAGCCAACACTATCGCTTGATTACATCACGTGCGAGTACAAAACCGTCATCCCGTC

TCCGTACGTGAAGTGCTGCGGTACAGCAGAGTGCAAGGACAAAAACCTACCTGACTACAGCTGT

AAGGTCTTCACCGGCGTCTACCCATTTATGTGGGGCGGCGCCTACTGCTTCTGCGACGCTGAAA

ACACGCAGTTGAGCGAAGCACACGTGGAGAAGTCCGAATCATGCAAAACAGAATTTGCATCAGC

ATACAGGGCTCATACCGCATCTGCATCAGCTAAGCTCCGCGTCCTTTACCAAGGAAATAACATCA

CTGTAACTGCCTATGCAAACGGCGACCATGCCGTCACAGTTAAGGACGCCAAATTCATTGTGGG

GCCAATGTCTTCAGCCTGGACACCTTTCGACAACAAAATTGTGGTGTACAAAGGTGACGTCTATA

ACATGGACTACCCGCCCTTTGGCGCAGGAAGACCAGGACAATTTGGCGATATCCAAAGTCGCAC

ACCTGAGAGTAAAGACGTCTATGCTAATACACAACTGGTACTGCAGAGACCGGCTGTGGGTACG

GTACACGTGCCATACTCTCAGGCACCATCTGGCTTTAAGTATTGGCTAAAAGAACGCGGGGCGTC

GCTGCAGCACACAGCACCATTTGGCTGCCAAATAGCAACAAACCCGGTAAGAGCGGTGAACTGC

GCCGTAGGGAACATGCCCATCTCCATCGACATACCGGAAGCGGCCTTCACTAGGGTCGTCGACG

CGCCCTCTTTAACGGACATGTCGTGCGAGGTACCAGCCTGCACCCATTCCTCAGACTTTGGGGG

CGTCGCCATTATTAAATATGCAGCCAGCAAGAAAGGCAAGTGTGCGGTGCATTCGATGACTAACG

CCGTCACTATTCGGGAAGCTGAGATAGAAGTTGAAGGGAATTCTCAGCTGCAAATCTCTTTCTCG

ACGGCCTTAGCCAGCGCCGAATTCCGCGTACAAGTCTGTTCTACACAAGTACACTGTGCAGCCG

AGTGCCACCCCCCGAAGGACCACATAGTCAACTACCCGGCGTCACATACCACCCTCGGGGTCCA

GGACATCTCCGCTACGGCGATGTCATGGGTGCAGAAGATCACGGGAGGTGTGGGACTGGTTGTT

GCTGTTGCCGCACTGATTCTAATCGTGGTGCTATGCGTGTCGTTCAGCAGGCACTAACTTGACAA

TTAAGTATGAAGGTATATGTGTCCCCTAAGAGACACACTGTACATAGCAAATAATCTATAGATCAA

AGGGCTACGCAACCCCTGAATAGTAACAAAATACAAAATCACTAAAAATTATAAAAACAGAAAAAT

ACATAAATAGGTATACGTGTCCCCTAAGAGACACATTGTATGTAGGTGATAAGTATAGATCAAAGG

GCCGAATAACCCCTGAATAGTAACAAAATATGAAAATCAATAAAAATCATAAAATAGAAAAACCATA

AACAGAAGTAGTTCAAAGGGCTATAAAACCCCTGAATAGTAACAAAACATAAAATTAATAAAAATC

AAATGAATACCATAATTGGCAAACGGAAGAGATGTAGGTACTTAAGCTTCCTAAAAGCAGCCGAA

CTCACTTTGAGAAGTAGGCATAGCATACCGAACTCTTCCACGATTCTCCGAACCCACAGGGACGT

AGGAGATGTTATTTTGTTTTTAATATTTCAAAAAAAAAAAAAAAAAAAAAAAAAAA

Amino acid sequence of E2 protein from LR2006_OPY1 Chikungunya
virus strain-amino acids 339-742 from structural polyprotein
GenBank Accession: ABD95938.1 (1-1248 aa)

SEQ ID NO: 2

STKDNFNVYKATRPYLAHCPDCGEGHSCHSPVALERIRNEATDGTLKIQVSLQIGIKTDDSHDWTKLR

YMDNHMPADAERAGLFVRTSAPCTITGTMGHFILARCPKGETLTVGFTDSRKISHSCTHPFHHDPPVI

GREKFHSRPQHGKELPCSTYVQSTAATTEEIEVHMPPDTPDHTLMSQQSGNVKITVNGQTVRYKCNC

GGSNEGLTTTDKVINNCKVDQCHAAVTNHKKWQYNSPLVPRNAELGDRKGKIHIPFPLANVTCRVPK

ARNPTVTYGKNQVIMLLYPDHPTLLSYRNMGEEPNYQEEVVVMHKKEVVLTVPTEGLEVTWGNNEPY

KYVVPQLSTNGTAHGHPHEIILYYYELYPTMTVVVVSVATFILLSMVGMAAGMCMCARRRCITPYELTP

-continued

GATVPFLLSLICCIRTAKA

Some E2 variants identified herein
E168K variant of E2 protein from Chikungunya virus
```
                                                     SEQ ID NO: 3
STKDNFNVYKATRPYLAHCPDCGEGHSCHSPVALERIRNEATDGTLKIQVSLQIGIKTDDSHDWTKLR

YMDNHMPADAERAGLFVRTSAPCTITGTMGHFILARCPKGETLTVGFTDSRKISHSCTHPFHHDPPVI

GREKFHSRPQHGKELPCSTYVQSTAATTEEIKVHMPPDTPDHTLMSQQSGNVKITVNGQTVRYKCNC

GGSNEGLTTTDKVINNCKVDQCHAAVTNHKKWQYNSPLVPRNAELGDRKGKIHIPFPLANVTCRVPK

ARNPTVTYGKNQVIMLLYPDHPTLLSYRNMGEEPNYQEEWVMHKKEVVLTVPTEGLEVTWGNNEPY

KYVVPQLSTNGTAHGHPHEIILYYYELYPTMTVVVVSVATFILLSMVGMAAGMCMCARRRCITPYELTP

GATVPFLLSLICCIRTAKA
```

G55R variant of E2 protein from Chikungunya virus
```
                                                     SEQ ID NO: 4
STKDNFNVYKATRPYLAHCPDCGEGHSCHSPVALERIRNEATDGTLKIQVSLQIRIKTDDSHDWTKLR

YMDNHMPADAERAGLFVRTSAPCTITGTMGHFILARCPKGETLTVGFTDSRKISHSCTHPFHHDPPVI

GREKFHSRPQHGKELPCSTYVQSTAATTEEIEVHMPPDTPDHTLMSQQSGNVKITVNGQTVRYKCNC

GGSNEGLTTTDKVINNCKVDQCHAAVTNHKKWQYNSPLVPRNAELGDRKGKIHIPFPLANVTCRVPK

ARNPTVTYGKNQVIMLLYPDHPTLLSYRNMGEEPNYQEEWVMHKKEVVLTVPTEGLEVTWGNNEPY

KYVVPQLSTNGTAHGHPHEIILYYYELYPTMTVVVVSVATFILLSMVGMAAGMCMCARRRCITPYELTP

GATVPFLLSLICCIRTAKA
```

E247K variant of E2 protein from Chikungunya virus
```
                                                     SEQ ID NO: 5
STKDNFNVYKATRPYLAHCPDCGEGHSCHSPVALERIRNEATDGTLKIQVSLQIGIKTDDSHDWTKLR

YMDNHMPADAERAGLFVRTSAPCTITGTMGHFILARCPKGETLTVGFTDSRKISHSCTHPFHHDPPVI

GREKFHSRPQHGKELPCSTYVQSTAATTEEIEVHMPPDTPDHTLMSQQSGNVKITVNGQTVRYKCNC

GGSNEGLTTTDKVINNCKVDQCHAAVTNHKKWQYNSPLVPRNAKLGDRKGKIHIPFPLANVTCRVPK

ARNPTVTYGKNQVIMLLYPDHPTLLSYRNMGEEPNYQEEWVMHKKEVVLTVPTEGLEVTWGNNEPY

KYVVPQLSTNGTAHGHPHEIILYYYELYPTMTVVVVSVATFILLSMVGMAAGMCMCARRRCITPYELTP

GATVPFLLSLICCIRTAKA
```

G82R variant of E2 protein from Chikungunya virus
```
                                                     SEQ ID NO: 6
STKDNFNVYKATRPYLAHCPDCGEGHSCHSPVALERIRNEATDGTLKIQVSLQIGIKTDDSHDWTKLR

YMDNHMPADAERARLFVRTSAPCTITGTMGHFILARCPKGETLTVGFTDSRKISHSCTHPFHHDPPVI

GREKFHSRPQHGKELPCSTYVQSTAATTEEIEVHMPPDTPDHTLMSQQSGNVKITVNGQTVRYKCNC

GGSNEGLTTTDKVINNCKVDQCHAAVTNHKKWQYNSPLVPRNAELGDRKGKIHIPFPLANVTCRVPK

ARNPTVTYGKNQVIMLLYPDHPTLLSYRNMGEEPNYQEEWVMHKKEVVLTVPTEGLEVTWGNNEPY

KYVVPQLSTNGTAHGHPHEIILYYYELYPTMTVVVVSVATFILLSMVGMAAGMCMCARRRCITPYELTP

GATVPFLLSLICCIRTAKA
```

H232Y variant of E2 protein from Chikungunya virus
```
                                                     SEQ ID NO: 7
STKDNFNVYKATRPYLAHCPDCGEGHSCHSPVALERIRNEATDGTLKIQVSLQIGIKTDDSHDWTKLR

YMDNHMPADAERAGLFVRTSAPCTITGTMGHFILARCPKGETLTVGFTDSRKISHSCTHPFHHDPPVI

GREKFHSRPQHGKELPCSTYVQSTAATTEEIEVHMPPDTPDHTLMSQQSGNVKITVNGQTVRYKCNC
```

-continued

```
GGSNEGLTTTDKVINNCKVDQCHAAVTNYKKWQYNSPLVPRNAELGDRKGKIHIPFPLANVTCRVPK

ARNPTVTYGKNQVIMLLYPDHPTLLSYRNMGEEPNYQEEWVMHKKEVVLTVPTEGLEVTWGNNEPY

KYVVPQLSTNGTAHGHPHEIILYYYELYPTMTVVVVSVATFILLSMVGMAAGMCMCARRRCITPYELTP

GATVPFLLSLICCIRTAKA
```

Further preferred aspects:

1. A pharmaceutical composition comprising i) a combination of an attenuated chikungunya virus as defined by the nucleic acid sequence of SEQ ID NO: 1 and variants thereof, wherein said variants have a nucleic acid sequence that is at least 99% identical to SEQ ID NO: 1 and comprises the entire deletion mutation of nsP3 as in SEQ ID NO: 1; and ii) pharmaceutically acceptable excipients, characterized in that said pharmaceutical composition is substantially safe and is able to induce a sustained protective immune response against a chikungunya virus in a human after a single dosage, wherein said dosage is about $10^3$ to $5\times10^4$ $TCID_{50}$/dose, preferably about $10^3$ to $2\times10^4$ $TCID_{50}$/dose.

2. The pharmaceutical composition of aspect 1, wherein said dosage is about $5\times10^3$ $TCID_{50}$/dose.

3. The pharmaceutical composition according to aspect 1 or 2, wherein said attenuated chikungunya virus variant expresses an E2 protein with at least one mutation, particularly an E protein as defined by SEQ ID Nos: 3-7.

4. The pharmaceutical composition of any one of aspects 1 to 3, wherein said attenuated chikungunya virus variant expresses an E2 protein with an E168K mutation as defined by SEQ ID NO: 3.

5. A pharmaceutical composition which is a one-shot vaccine essentially consisting of i) a mixture of CHIKV-Δ5nsP3 which expresses an E2 protein as defined by SEQ ID NO: 2 and a CHIKV-Δ5nsP3 which expresses an E2 protein as defined by SEQ ID NO: 3; and ii) pharmaceutically acceptable excipients, wherein said mixture is delivered at a dose of about $10^3$ to $5\times10^4$ $TCID_{50}$/dose, preferably about $10^3$ to $2\times10^4$ $TCID_{50}$/dose.

6. The pharmaceutical composition of any one of aspects 1 to 5, wherein said composition is a liquid frozen composition.

7. The pharmaceutical composition of any one of aspects 1 to 5, wherein said composition is a lyophilized composition.

8. The pharmaceutical composition of any of aspects 1 to 7, wherein the pharmaceutically acceptable excipients essentially consist of sucrose, potassium phosphate and sodium citrate and, optionally, magnesium chloride, D-sorbitol, L-methionine and recombinant human serum albumin rHSA.

9. The pharmaceutical composition according to any one of aspects 1 to 8, wherein said pharmaceutically acceptable excipients essentially consist of about 5% (w/v) sucrose, about 10 mM potassium phosphate, about 25 mM sodium citrate and about 0.01% (w/v) recombinant human serum albumin (rHSA).

10. The pharmaceutical composition according to any one of aspects 1 to 8, wherein said pharmaceutically acceptable excipients essentially consist of about 5% (w/v) sucrose; about 5 mM potassium phosphate; about 25 mM sodium citrate; about 5 mM MgCl2; about 0.5%

(w/v) D-sorbitol; about 10 mM L-methionine; and about 0.01% (w/v) recombinant human serum albumin (rHSA).

11. The pharmaceutical composition of any one of aspects 1 to 10, wherein said composition is able to increase serum antibody titers to said virus in a human by at least 1 log relative to a control within about 14 days from primary immunization.

12. The pharmaceutical composition of any one of aspects 1 to 10, wherein said composition is able to increase serum antibody titers to said virus in a human by at least 1 log relative to a control within about 7 days from primary immunization.

13. The pharmaceutical composition of any one of aspects 1 to 12, wherein said composition is able to stimulate seroconversion in at least 25%, at least 30%, at least 40%, at least 50%, at least 60%, at least 70%, at least 80%, at least 90%, at least 91%, 92%, 93%, 94%, 95%, 96%, 97%, 98%, 99%, up to 100% of vaccinated subjects within 7 days of vaccination, wherein seroconversion is defined as reaching a CHIKV-specific antibody titer of at least 10.

14. The pharmaceutical composition of any one of aspects 1 to 12, wherein said composition is able to stimulate seroconversion in at least 25%, at least 30%, at least 40%, at least 50%, at least 60%, at least 70%, at least 80%, at least 90%, at least 91%, 92%, 93%, 94%, 95%, 96%, 97%, 98%, 99%, up to 100% of vaccinated subjects within 14 days of vaccination, wherein seroconversion is defined as reaching a CHIKV-specific antibody titer of at least 10.

15. The pharmaceutical composition of any one of aspects 1 to 14, wherein the protective immune response lasts for at least 6 months.

16. The pharmaceutical composition of any one of aspects 1 to 14, wherein the protective immune response lasts for at least 12 months.

17. The pharmaceutical composition of any one of aspects 1 to 14, wherein the protective immune response lasts for at least 24 months.

18. The pharmaceutical composition of any one of aspects 1 to 17, for use in a method of treating or preventing a Chikungunya virus infection.

19. A method of treating or preventing a Chikungunya virus infection in a subject in need thereof, comprising administering an effective amount of the pharmaceutical composition according to any one of aspects 1 to 17.

1A. A liquid frozen or lyophilized life chikungunya vaccine formulation comprising: a) an effective amount of at least one strain of life chikungunya virus; b) about 1 to 50% (w/v) sugar; c) about 1 mM to about 20 mM phosphate; d) about 1 mM to about 50 mM of at least one carboxylate; e) optionally about 1 mM to about 10 mM $MgCl_2$; f) optionally about 0.1% to about 5% (w/v) D-sorbitol; g) optionally about 1 mM to 20 mM L-methionine; and h) optionally about 0.001% to about 0.1% (w/v) human serum albumin.

2A. The formulation of aspect 1A, wherein the human serum albumin is a recombinant human serum albumin.

3A. The formulation according to any preceding aspects wherein said at least one carboxylate is selected from the group consisting of succinate, citrate, fumarate, tartarate, maleate and lactate.

4A. The formulation according to any preceding aspects wherein said sugar is selected from the group consisting of sucrose, mannitol, lactose, sorbitol, dextrose, fucose and trehalose.

5A. The formulation according to any preceding aspects wherein the concentration of sugar is between about 1 to about 10%; the concentration of phosphate is between about 1 to about 10 mM; and said at least one carboxylic acid is citrate or succinate at a concentration between about 10 to about 30 mM.

6A. The formulation according to any preceding aspects further comprising: k) at least one diluent selected from the group consisting of tissue culture medium, saline and water to volume.

7A. The formulation according to any preceding aspects wherein the pH is between about pH 5.0 to about pH 8.0, preferably between pH 7.0 and pH 7.5, most preferred pH 7.3.

8A. The formulation according to any preceding aspects wherein said phosphate is selected from the group consisting of monophosphates, polyphosphates and phosphorylated compounds.

9A. The formulation according to aspect 8A wherein said monophosphate is potassium phosphate.

10A. The formulation according to any preceding aspects wherein formulation comprises an effective amount of at least one strain of chikungunya virus; b) sucrose at a concentration of about 5% (w/v); c) potassium phosphate at a concentration of about 5 mM to about 10 mM; d) sodium citrate at a concentration of about 25 mM; e) MgCl2 at a concentration of about 10 mM; f) D-sorbitol at a concentration of about 0.5% (w/v), g) L-methionine at a concentration of about 10 mM; and h) recombinant human serum albumin at a concentration of about 0.01% (w/v).

11A. The formulation according to any preceding aspects wherein formulation comprises an effective amount of at least one strain of chikungunya virus; b) about 5% (w/v) sucrose; c) about 5 mM potassium phosphate; d) about 25 mM sodium citrate; e) about 10 mM MgCl2; f) about 0.5% (w/v) D-sorbitol, g) about 10 mM L-methionine; and h) about 0.01% (w/v) recombinant human serum albumin.

12A. The formulation according to any preceding aspects wherein said chikungunya virus is selected from an attenuated chikungunya virus of SEQ ID NO: 1; variants with 99% sequence identity to SEQ ID NO: 1 of which have the 60aa deletion as in SEQ ID NO: 1; and/or combinations thereof.

13A. The formulation according to any preceding aspects wherein said chikungunya virus comprises essentially an attenuated chikungunya virus of SEQ ID NO: 1 and a variant with 99% sequence identity to SEQ ID NO: 1 and having the 60aa deletion as in SEQ ID NO: 1.

14A. The formulation according to any preceding aspects wherein said at least one strain of chikungunya virus is selected from an attenuated chikungunya virus population that comprises substantially 2 variants, said variants expressing the E1 wild type amino acid sequence as encoded in the relevant part of nucleic acid sequence SEQ ID NO: 1 and wherein one variant expressing the wild type E2 structural protein as defined in SEQ ID NO:2 and wherein the other variant expressing the E168K mutation in the E2 structural protein as defined in SEQ ID NO:3.

15A. The lyophilized chikungunya vaccine formulation according to any preceding aspects wherein said chikungunya virus is an attenuated chikungunya virus population that comprises substantially 2 variants, said variants expressing E2 structural proteins as defined by the amino acid sequences of SEQ ID NO: 2 and SED ID NO: 3 (with E168K) and wherein said 2 variants have a combined dose between about $10^3$ and $2 \times 10^4$ $TCID_{50}$/dose and a target potency of about $5 \times 10^3$ $TCID_{50}$/dose.

16A. The lyophilized chikungunya vaccine formulation according to any preceding aspects wherein said chikungunya virus is an attenuated chikungunya virus population that comprises one or more variants and wherein the variant has one or more mutations in E2 which mutations are shown in the group of variants encoding for an E2 amino acid sequence with E168K (SEQ ID NO: 3), G55R (SEQ ID NO: 4), E247K (SEQ ID NO: 5), G82R (SEQ ID NO: 6) and/or H232Y (SEQ ID NO: 7).

17A. A method of preparing chikungunya virus vaccine formulations, comprising:

(a) cultivating a chikungunya virus and mixing the chikungunya virus with a concentrated stabilizing solution to form a virus bulk; and, optionally, (b) dialyzing the virus bulk to form a chikungunya virus vaccine solution; wherein the vaccine solution comprises a) about 1 to 50% (w/v) sugar; b) about 1 mM to about 20 mM phosphate; c) about 1 mM to about 50 mM of at least one carboxylate; d) about 1 mM to about 10 mM MgCl2; e) about 0.1% to about 5% (w/v) D-sorbitol; g) about 1 mM to 20 mM L-methionine; and f) about 0.001% to about 0.1% (w/v) human serum albumin.

18A. The method of aspect 17A, wherein the stabilizing solution comprises a) about 5% (w/v) sugar; b) about 20 mM phosphate; c) about 25 mM citrate; d) about 10 mM MgCl2; e) about 0.5% (w/v) D-sorbitol; f) about 10 mM L-methionine; and g) about 0.01% (w/v) human serum albumin.

19A. The method of aspect 17A or 18A, wherein the dialyzing is done to form a formulation of any of aspects 1A to 16A.

20A. The method of aspects 17A-19A further comprising the step of lyophilizing the vaccine solution.

1B. A pharmaceutical unit dosage composition comprising i) an attenuated chikungunya virus; and ii) one or more pharmaceutically acceptable excipients, characterized in that said pharmaceutical composition is able to induce a sustained protective immune response against a chikungunya virus in a human after a single dosage, wherein said unit dosage composition comprises about $10^3$ to $5 \times 10^4$ $TCID_{50}$/dose, preferably about $10^3$ to $2 \times 10^4$ $TCID_{50}$/dose.

2B. The pharmaceutical composition according to aspect 1B, wherein said attenuated chikungunya virus comprises an RNA genome corresponding to the DNA sequence as defined by SEQ ID NO: 1 (CHIKV-Δ5nsP3) and/or one or more variants thereof, wherein said variant has a nucleic acid sequence that is at least 99% identical to SEQ ID NO: 1 and comprises the entire 60 amino acid deletion in nsP3 as in SEQ ID NO: 1.

3B. The pharmaceutical composition of aspect 1B or 2B, wherein said dosage is about $5 \times 10^3$ TCID$_{50}$/dose.

4B. The pharmaceutical composition according to aspect 2B or 3B, wherein said attenuated chikungunya virus variant expresses an E2 protein with at least one mutation compared with the wild-type E2 protein as defined by SEQ ID NO: 2, particularly an E2 protein as defined by any of SEQ ID Nos: 3-7.

5B. The pharmaceutical composition of any one of aspects 2B to 4B, wherein said attenuated chikungunya virus variant expresses an E2 protein with an E168K mutation as defined by SEQ ID NO: 3.

6B. A pharmaceutical composition for use as a one-shot vaccine for the prevention or treatment of chikungunya virus infection, wherein the composition comprises or consists of i) CHIKV-Δ5nsP3 which expresses an E2 protein as defined by SEQ ID NO: 2, a CHIKV-Δ5nsP3 which expresses an E2 protein as defined by SEQ ID NO: 3 or a mixture thereof; and ii) one or more pharmaceutically acceptable excipients, wherein said composition is administered to a subject at a dose of about $10^3$ to $5 \times 10^4$ TCID$_{50}$/dose, preferably about $10^3$ to $2 \times 10^4$ TCID$_{50}$/dose.

7B. The pharmaceutical composition of any one of aspects 1B to 6B, wherein said composition is a liquid frozen composition.

8B. The pharmaceutical composition of any one of aspects 1B to 6B, wherein said composition is a lyophilized composition.

9B. The pharmaceutical composition of any one of aspects 1B to 8B, wherein the pharmaceutically acceptable excipients essentially consist of sucrose, potassium phosphate and sodium citrate and, optionally, magnesium chloride, D-sorbitol, L-methionine and recombinant human serum albumin rHSA.

10B. The pharmaceutical composition according to any one of aspects 1B to 9B, wherein said pharmaceutically acceptable excipients essentially consist of about 5% (w/v) sucrose, about 10 mM potassium phosphate, about 25 mM sodium citrate and about 0.01% (w/v) recombinant human serum albumin (rHSA).

11B. The pharmaceutical composition according to any one of aspects 1B to 9B, wherein said pharmaceutically acceptable excipients essentially consist of about 5% (w/v) sucrose; about 5 mM potassium phosphate; about 25 mM sodium citrate; about 5 mM MgCl$_2$; about 0.5% (w/v) D-sorbitol; about 10 mM L-methionine; and about 0.01% (w/v) recombinant human serum albumin (rHSA).

12B. The pharmaceutical composition of any one of aspects 1B to 11B, wherein said composition is able to increase serum antibody titers to said virus in a human by at least 1 log relative to a control within about 14 days from primary immunization.

13B. The pharmaceutical composition of any one of aspects 1B to 11B, wherein said composition is able to increase serum antibody titers to said virus in a human by at least 1 log relative to a control within about 7 days from primary immunization.

14B. The pharmaceutical composition of any one of aspects 1B to 13B, wherein said composition is able to stimulate seroconversion in at least 25%, at least 30%, at least 40%, at least 50%, at least 60%, at least 70%, at least 80%, at least 90%, at least 91%, 92%, 93%, 94%, 95%, 96%, 97%, 98%, 99%, up to 100% of vaccinated subjects within 7 days of vaccination, wherein seroconversion is defined as reaching a neutralizing CHIKV antibody titer of at least 10, preferably at least 20.

15B. The pharmaceutical composition of any one of aspects 1B to 13B, wherein said composition is able to stimulate seroconversion in at least 25%, at least 30%, at least 40%, at least 50%, at least 60%, at least 70%, at least 80%, at least 90%, at least 91%, 92%, 93%, 94%, 95%, 96%, 97%, 98%, 99%, up to 100% of vaccinated subjects within 14 days of vaccination, wherein seroconversion is defined as reaching a neutralizing CHIKV antibody titer of at least 10, preferably at least 20.

16B. The pharmaceutical composition of any one of aspects 1B to 15B, wherein the protective immune response lasts for at least 6 months.

17B. The pharmaceutical composition of any one of aspects 1B to 15B, wherein the protective immune response lasts for at least 12 months.

18B. The pharmaceutical composition of any one of aspects 1B to 15B, wherein the protective immune response lasts for at least 24 months.

19B. The pharmaceutical composition of any one of aspects 1B to 15B, wherein the protective immune response confers life-long protection against CHIK virus disease.

20B. The pharmaceutical composition of any one of aspects 1B to 19B, for use in a method of treating or preventing a Chikungunya virus infection.

21B. A method of treating or preventing a Chikungunya virus infection in a subject in need thereof, comprising administering an effective amount of the pharmaceutical composition according to any one of aspects 1B to 17B.

---

What is claimed is:

1. A lyophilized live chikungunya vaccine formulation lyophilized from a composition comprising: a) an effective amount of at least one strain of live chikungunya virus; b) 1% to 20% (w/v) sugar; c) 1 mM to 20 mM phosphate; d) 1 mM to 50 mM of at least one carboxylate buffering agent; e) 1 mM to 10 mM MgCl$_2$; f) 0.1% to 5% (w/v) D-sorbitol; g) 1 mM to 20 mM L-methionine; and h) 0.001% to 0.1% (w/v) human serum albumin (HSA), wherein said at least one strain of live chikungunya virus is selected from an attenuated chikungunya virus of SEQ ID NO: 1; variants with 99% sequence identity to SEQ ID NO: 1, wherein said variant also has the 60 aa deletion as in SEQ ID NO: 1; and/or combinations thereof.

2. The formulation according to claim 1, wherein the human serum albumin is a recombinant human serum albumin (rHSA).

3. The formulation according to claim 1 wherein said at least one carboxylate buffering agent is selected from the group consisting of succinate, citrate, fumarate, tartrate, maleate and lactate.

4. The formulation according to claim 1 wherein said sugar is selected from the group consisting of sucrose, mannitol, lactose, sorbitol, dextrose, fucose and trehalose.

5. The formulation according to claim 1 wherein the concentration of sugar is between 1% to 10%; the concentration of phosphate is between 1 mM to 10 mM; and said at least one carboxylate buffering agent is citrate or succinate at a concentration between 10 mM to 30 mM.

6. The formulation according to claim 1 further comprising: i) at least one diluent selected from the group consisting of tissue culture medium, saline and water to volume.

7. The formulation according to claim 1 wherein the pH is between pH 5.0 and pH 8.0.

8. The formulation according to claim 1 wherein said phosphate is selected from the group consisting of mono-phosphates, polyphosphates and phosphorylated compounds.

9. The formulation according to claim 8 wherein said monophosphate is potassium phosphate.

10. The formulation according to claim 1 wherein said formulation comprises an effective amount of at least one strain of chikungunya virus; b) sucrose at a concentration of 5% (w/v); c) potassium phosphate at a concentration of 5 mM; d) sodium citrate at a concentration of 25 mM; e) $MgCl_2$ at a concentration of 5 mM; f) D-sorbitol at a concentration of 0.5% (w/v), g) L-methionine at a concentration of 10 mM; and h) recombinant human serum albumin at a concentration of 0.01% (w/v).

11. The formulation according to claim 1 wherein said at least one strain of live chikungunya virus comprises essentially an attenuated chikungunya virus of SEQ ID NO: 1 and a variant with 99% sequence identity to SEQ ID NO: 1, wherein the variant also has the 60aa deletion in the nsP3 protein as in SEQ ID NO: 1.

12. The formulation according to claim 1 wherein said at least one strain of live chikungunya virus is selected from an attenuated chikungunya virus population that comprises substantially two variants, said two variants both expressing the E1 wild type amino acid sequence as encoded in the relevant part of nucleic acid sequence SEQ ID NO: 1 and wherein one variant expresses the wild type E2 structural protein as defined in SEQ ID NO: 2 and wherein the other variant expresses the E168K mutation in the E2 structural protein as defined in SEQ ID NO: 3.

13. The formulation according to claim 1 wherein said at least one strain of live chikungunya virus is an attenuated chikungunya virus population that comprises substantially two variants, said two variants expressing E2 structural proteins as defined by the amino acid sequences of SEQ ID NO: 2 and SED ID NO: 3 with E168K, respectively, and wherein said two variants have a combined dose of between about $10^3$ and $2 \times 10^4$ $TCID_{50}$/dose and a target potency of about $5 \times 10^3$ $TCID_{50}$/dose.

14. The formulation according to claim 1 wherein said at least one strain of live chikungunya virus is an attenuated chikungunya virus population that comprises one or more variants and wherein the variant has one or more mutations in E2 which mutations are shown in the group of variants encoding for an E2 amino acid sequence with E168K (SEQ ID NO: 3), G55R (SEQ ID NO: 4), E247K (SEQ ID NO: 5), G82R (SEQ ID NO: 6) and/or H232Y (SEQ ID NO: 7).

15. A method of preparing a lyophilized chikungunya formulation, comprising:
    (i) cultivating a chikungunya virus and mixing the chikungunya virus with a concentrated stabilizing solution to form a virus bulk (i); and, optionally,
    (ii) dialyzing the virus bulk (i) to form a composition (ii); wherein said composition (ii) comprises a) 1% to 20% (w/v) sugar; b) 1 mM to 20 mM phosphate; c) 1 mM to 50 mM of at least one carboxylate; d) 1 mM to 10 mM $MgCl_2$; e) 0.1% to 5% (w/v) D-sorbitol; g) 1 mM to 20 mM L-methionine; and f) 0.001% to 0.1% (w/v) human serum albumin (HSA); and
    (iii) lyophilizing said virus bulk (i) or composition (ii).

16. The method according to claim 15, wherein the stabilizing solution comprises a) 5% (w/v) sucrose; b) 5 mM phosphate; c) 25 mM citrate; d) 5 mM $MgCl_2$; e) 0.5% (w/v) D-sorbitol; f) 10 mM L-methionine; and g) 0.01% (w/v) recombinant human serum albumin.

17. The method according to claim 15, wherein said dialyzing step (ii) results in the formulation according to claim 1.

18. The formulation according to claim 1 for use in a method of vaccinating a human subject to stimulate a protective immune response against Chikungunya virus in said subject.

19. The formulation according to claim 4 wherein said sugar is sucrose.

20. The formulation according to claim 7 wherein the pH is 7.3.

\* \* \* \* \*